United States Patent [19]
Silverman et al.

[11] Patent Number: 5,972,678
[45] Date of Patent: *Oct. 26, 1999

[54] ANIMAL 2-5A DEPENDENT RNASES

[75] Inventors: Robert H. Silverman, Shaker Heights; Bret A. Hassel, Chagrin Falls; Aimin Zhou, Solon, all of Ohio

[73] Assignee: Cleveland Clinic Foundation, Cleveland, Ohio

[*] Notice: This patent is subject to a terminal disclaimer.

[21] Appl. No.: 08/479,895

[22] Filed: Jun. 7, 1995

Related U.S. Application Data

[63] Continuation of application No. 08/028,086, Mar. 8, 1993, abandoned.

[51] Int. Cl.$^6$ .................................................. C12N 9/22
[52] U.S. Cl. ............... 435/199; 435/252.33; 435/320.1; 536/23.2; 536/23.5
[58] Field of Search ............................ 435/199, 240.2, 435/252.33, 320.1; 536/23.2, 23.5

[56] References Cited

U.S. PATENT DOCUMENTS 5,063,159  11/1991  Revel et al. .................... 435/252.3

FOREIGN PATENT DOCUMENTS

WO 93/19187   9/1993   WIPO.

OTHER PUBLICATIONS

Silverman et al.: *J. Cell Biol. Supplement 16B,* See Abstract G 520, p. 163 (1992).
Meurs, E. et al.: *Cell,* 62:379–390 (Jul. 27, 1990).
Meurs, E. et al.: *J. Virology,* 66(10):5805–5814 (1992).
Lee, S.B. et al.: *Virology,* 193:1037–1041 (1993).
Lomonossoff, G.P.: Virus Resistance Mediated by a Non-structural Viral Gene Sequence, Chapter 5, pp. 79–91 (1993). In: *Transgenic Plants,* ed. Hiatt, A. Marcel Dekker, Inc. NY, NY.
Herrera–Estrella, L. et al.: Agrobacterium as a Vector System for the Introduction of Genes into Plants, Chapter 5 pp. 61–92, In: *Plant Genetic Engineering,* ed. Dodds, J.H., Cambridge University Press, NY, NY (1985).
Mukherjee, A.B. et al.: *Biochemical Pharmacology,* 48(1):1–10 (1994).
Yang, N.S.: *Critical Reviews in Biotechnology,* 12(4):335–356 (1992).
Deng, T. et al.: *Gene,* 93:229–234 (1990).
Seilhamer, J.J. et al.: *J. Cell Biochem.,* 39:327–337 (1989).
Bekkers, A.C.A.P.A. et al.: *Biochimica et Biophysica Acta,* 1089:345–351 (1991).
Luckow et al.: *Biotechnology,* 6:47–55 (1988).
Seidah et al.: *DNA Cell Biol.*
Nolan–Sorden, N.L.: *Anal. Biochem.,* 184–298–304 (1990).
Kerr, I.M. et al.: *Proc. Natl. Acad. Sci USA,* 75(1):256–260 (Jan. 1978).
Slattery, E. et al.: *Pro. Natl. Acad. Sci USA.*
Clemens, M.J. et al. *Cell,* 13:565–572 (Mar. 1978).

Knight, M. et al.: *Nature,* 288(5787):189–192 (Nov. 13, 1980).
Wreschner, D.H. et al.: *Eur. J. Biochem.,* 124,261–268(1982).
Jacobsen, H. et al.: *Virology,* 125:496–501 (1983).
Feng, G., et al.: *Proc. Natl. Acad. Sci. USA* 89, pp. 5447–5451 (1992).
Saunders, M. et al.: *The 2–5A System, Molecular and Clinical Aspects of the Interferon–Regulated Pathway,* A.R. Liss, Inc. pp. 163–174 (1985).
Aebi, M. et al.: *Mol. Cell. Biol.,* 9:5062 (1989).
Jacobsen, H. et al.: *Proc. Natl. Acad. Sci. USA,* 80:4954–4958 (Aug. 1983).
Silverman, R.H. et al.: Local Organ. Comm. of 5th Ann. Meeting of Interf. Res. ( *The Biol. of Interf. Syst. 1988*), 183–186 (1989).
Ferbus, D. et al.: *Mol. & Cell. Biochem.,* 62:51–55 (1984).
Eppstein D.A. et al.: *J. Biol. Chem.,* 257(22):13390–13397 (1982).
Hovanessian, A.G. et al.: *J. Biol. Chem.,* 263(10):4945–4949 (1988).
Hovanessian, A.G. et al.: *EMBO J.,* 6(5):1273–1280 (1987).
Hearl, W.G. et al.: *J. Virol.,* 61(5):1586–1592 (1987).
Wreschner, D.H. et al.: *Nature,* 289(5796):414–417 (Jan. 29, 1981).
Debois, M.F. et al.: *Ann. Inst. Pasteur/Virol.,* 1987.
Yang–Feng, T.L. et al.: *Genomics,* 19:173–176 (1994).
Dong, B. et al.: *J. Biol. Chem.,* 269(19):14153–14158 (May 13, 1994).
Hassel, H.A. et al.: *EMBO J.,* 12(8):3297–3304 (1993).
Zhou, A. et al.: *Cell,* 72:753–765 (Mar. 12, 1993).
William, B.R.G. et al.: Local Org. Comm. of 5th Ann. Meet. of Interf. Res. (*The Biol. of Interf. Syst.*), 159–162 (1988).
Sawai, H. et al.: *J. Biol. Chem.,* 288(3):1671–1677 (Feb. 10, 1983).

(List continued on next page.)

*Primary Examiner*—Rebecca E. Prouty
*Assistant Examiner*—Nashaat T. Nashed
*Attorney, Agent, or Firm*—Rothwell, Figg, Ernst & Kurz

[57] ABSTRACT

Isolated 2-5A-dependent RNases, an interferon-induced enzyme which is activated by 5'-phosphorylated, 2',5'-linked oligoadenylates (2-5A) and implicated in both the molecular mechanisms of interferon action and in the fundamental control of RNA stability in mammalian cells, and encoding sequences therefor are disclosed. The expression cloning and analysis of murine and human 2-5A-dependent RNases is also disclosed. Recombinant human 2-5A-dependent RNase produced in vitro bound an activating affinity matrix, 2-5A-cellulose, resulting in ribonuclease activity. The 2-5A binding properties of the recombinant and naturally occurring forms of 2-5A-dependent RNase are basically identical. Interferon induction of 2-5A-dependent RNase expression is demonstrated by measuring the mRNA levels in cells treated with interferon and cycloheximide. Analysis of aligned murine and human 2-5A-dependent RNase sequences revealed several features, including similarity to RNase E which is implicated in the control of mRNA stability in *E. coli*. A duplicated phosphate-binding loop motif is determined by deletion analysis and site-directed mutagenesis to function in the binding of 2-5A.

7 Claims, 17 Drawing Sheets

OTHER PUBLICATIONS

Torrence, P.F. et al.: *J. Biol. Chem.,* 263(3):1131–1139 (Jan. 25, 1988).
Lesiak, K. et al.: *J. Biol. Chem.,* 258(21):13082–13088 (Nov. 10, 1983).
Black, R.J. et al.: *FEBS Letters,* 191(1):154–158 (Oct. 1985).
Gura: Science, 270:575–577 (Oct. 27, 1995).
Nejidat et al.: Physiologia Plantarum, 80:662–668 (1990).
Gergerich et al.: Phytopathology, 78(3):270–272 (1988).
Cuozzo et al.: Bio/Technology, 6:549–557 (May 1988).
Sawai, H. et al.: *J. Biol. Chem.,* 258(3):1671–1677 (Feb. 1, 1983).
Torrence, P.F. et al.: *Proc. Natl. Acad. Sci. USA,* 78(1):5993–5997 (Oct. 1981).
Lesiak, K. et al.: *J. Biol. Chem.,* 262(5):1961–1965 (Feb. 15, 1987).
Lesiak, K. et al.: *Bioconjugate Chem.,* 467–472 (Nov./Dec. 1993).
Jacobsen, H.J. et al.: *Virology,* 125:496–501 (1983).
SenGupta, D.N. et al.: *Proc. Natl. Acad. Sic. USA,* 87:7492–7496 (Oct. 1990).
Silverman, R.H.: *Anal. Biochem.,* 144:450–460 (1985).
Krause, D. et al.: *J. Interf. Res.,* 13:13–16 (1993).
Krause, D. et al.: *J. Biol. Chem.,* 260(16):9501–9507 (Aug. 5, 1985).
Kraus, D. et al.: *J. Biol. Chem.,* 261(15):6836–6839 (May 25, 1986).
Maheshwari, R.K. et al.: *Science,* 219:1339–1341 (Mar. 18, 1983).
SenGupta, D.N.: *Proc. Natl. Acad. Sci. USA,* 87:7492–7496 (Oct. 1990).
Silverman, R.H.: *Eur. J. Biochem.,* 126:333–341 (1982).
Ryseicki, G.: *J. Interf. Res.,* 9:649–657 (1989).
Wreschner, D.H. et al.: *Nucleic Acids Res.,* 9(7):1571–1581 (1981).
Cayley, P.J. et al.: *Cell. Resp. to Mol. Modul.,* 347–360.
Torrence, P.F. et al.: *Proc. Natl. Acad. Sci. USA,* 90:1300–1304 (Feb. 1993).
Silverman, R.H. et al.: *Biol. of Interf. System,* 189–200 (1983).
Silverman, R.H. et al.: *J. Virology,* 46(3):1051–1055 (Jun. 1983).
Grimley, P.M. et al.: *Cancer Res.,* 144:3480–3488 (Aug. 1984).
Sen Gupta, D.N. et al.: *Nucleic Acids Res.,* 17(3):969–978 (1989).
Silverman, R.H.: *J. Interf. Res.,* 14:101–104 (1994).
Kerr, I.M.: *Phil. Trans. R. Soc. Lond.,* B299:59–67 (1982).
Meurs, E. et al.: *Ann. Inst. Pasteur/Virol.,* 137E:251–272 (1986).
Schmidt, A. et al.: *Nat. Immun. Cell Growth Regul.,* 6:19–27 (1987).
Dieffenbach, C.W. et al.: *J. Biol. Chem.,* 264(22):13281–13288 (1989).
Suhadolnik, R.J. et al.: *Biochem.,* 27:8846–8851 (1988).
Wells, J.A. et al.: *J. Biol. Chem.,* 259(2):1363–1370 (Jan. 25, 1984).
Reid, T.R. et al.: *Anal. Biochem.,* 135:000–000 (1983).
Hersh, C.L. et al.: *J. Biol. Chem.,* 259(3):1727–1730 (Feb. 10, 1984).
Iwata, A. et al.: *J. Biochem.,* 104:247–250 (1988).
Shimizu, N. et al.: *J. Biochem.,* 94:1421–1428 (1983).
Orlic, D. et al.: *Exp. Hematol.,* 13:821–826 (1985).
Orlic, D. et al.: *Blood Cells,* 10:193–210 (1984).
Lewis, J.A. et al.: *Viology,* 133:464–469 (1984).
Mengheri, E. et al.: *FEBS,* 157(2):301–305 (Jul. 1983).
Lewis, J.A. et al.: *Eur. J. Biochem.,* 86:497–509 (1978).
Lewis, J.A. et al.: *Proc. Natl. Acad. Sci. USA,* 80:26–30 (Jan. 1983).
Schnatter, A. et al.: *J. Interf. Res.,* 1(4):587–594 (1981).
Weissenbach, J. et al.: *Proc. natl. Acad. Sci. USA,* (77)(12):7152–7156 (Dec. 1980).
Revel, M. et al.: *Texas Reports on Biology and Medicine,* 41:452–462 (1981–82).
Revel, M.: "Molecular Mechanisms Involved in the Intiviral Effects of Interferon," 101–163.
Revel, M. et al.: *Cell. Resp. Mol. Modul.,* 361–384.
Wallach, D. et al.: *Nature,* 287:68–90 (Sep. 1989).
Revel, M. et al.: *Ann. Rev. Biochem.,* 47:1079–1126 (1978).
Chernajovsky, Y. et al.: *Eur. J. Biochem.,* 96:35–41 (1979).
Wallach, D. et al.: *Interferons,* 449–463 (1982).
Kimchi, A. et al.: *Proc. Natl. Acad. Sci. USA,* 76(7):3208–3212 (Jul. 1979).
Kimchi, A. et al.: *Anti–Mitogenic Func. of Interf.–Induced (2'–5')Oligo(adenylate . . . ,* 5–10 (1980).
Zilberstein, A. et al.: *Proc. natl. Acad. Sci. USA,* 75(1):4734–4738 (Oct. 1978).
Kimchi, A. et al.: *FEBS,* 134(2):212–216 (Nov. 1981).
Chebath, J. et al.: *J. Biol. Chem.,* 262(8)3852–3857 (Mar. 15, 1987).
Rappoport, S. et al.: *FEBS,* 149(1):47–50 (Nov. 1982).
Panet, A. et al.: *Virology,* 114:567–572 (1981).
Epstein, D.A. et al.: *Eur. J. Biochem.,* 118:9–15 (1981).
Sen, G.C.: *Pharmac. Ther.,* 24:235–257 (1984).
Kumar, R. et al.: *J. Virol.,* 62(2)641–643 (Feb. 1988).
Salzberg, S. et al.: *Mol. Cell. Biol.,* 3(10):1759–1765 (Oct. 1983).
Panet, A.: *Mol. Cell. Ciochem.,* 52:153–160 (1983).
Lewis, J.A.: *Virology,* 162:118–127 (1988).
Neth, R. et al.: Reprint from *Modern Trends in Human Leukemia III* (Springer–Verlag Berlin Heidelberg Ny 1979).
Kemchi, A. et al.: *Nature,* 282:20–27 (Dec. 1979).
Sen, G.C. et al.: *J. Biol. Chem.,* 253(17):5915–5921 (Sep. 10, 1978).
Shimizu, N. et al.: *J. Biol. Chem.,* 254(23):12034–12037 (Dec. 10, 1979).
Schmidt, A. et al.: *Proc. natl. Acad. Sci. USA,* 76(10):4788–4792 (Oct. 1979).
Revel, M. et al.: "Studies on Interef. Action: Synth., Degrad. & Biol. Act. of (2'–5')Oligo–Isoadenylate," 1–18.
Lengyel, P. et al.: *J. Interf. Res.,* 7:511–519 (1987).
Floyd–Smith, G. et al.: *J. Interf. Res.,* 8:517–525 (1988).
Salehzada, T. et al.: *J. Biol. Chem.,* 266(9):5808–5813 (Mar. 25, 1991).
Hovanessian, A.G. et al.: *Nature,* 268:537–538 (Aug. 1977).
Salehzda, T. et al.: *Anal. Biochem.,* 196:410–414 (1991).
Williams, B.R.G. et al.: *Nature,* 276:88–90 (Nov. 1978).
Roberts, W.K. et al.: *Proc. Natl. Acad. Sci. USA,* 73(9):3136–3140 (Sep. 1976).
Kerr, I.M. et al.: *Nature,* 268:537–542.
Salehzada, T. et al.: *J. Biol. Chem.,* 268(11):7733–7740 (Apr. 15, 1993).
Lengyel, P.: *Proc. Natl. Acad. Sci. USA,* 90:5893–5895 (Jul. 1993).
Cayley, P.J. et al.: *Piochem. Biophys. Res. Comm.,* 108(3):1243–1250 (Oct. 15, 1982).
Kerr, I.M. et al.: *Eur. J. Biochem.,* 69:551–561 (1976).
Kumar, R. et al.: *J. Virol.,* 62(9):3175–3181 (Sep. 1988).

Shaila, S. et al.: *gen. Virol.*, 37:535–546 (1977).
Brown, G.E. et al.: *Biochem. Biophys. Res. Commun.*, 69(1):114–122 (1976).
Sen, G.C. et al. *Nature*, 264:370–373 (Nov. 25, 1976).
Hanks, S.K. et al.: *Science*, 241:42–52 (Jul. 1988).
Singh, H. et al.: *Cell*, 52:415–423 (Feb. 12, 1988).
Singh, H. et al.: *BioTech.*, 7(3):252–261 (1989).
Baglioni, C. et al.: *Nature*, 273:684–687 (Jun. 1978).
Apirion, D.: "Isolation, Genetic Mappern and Some Characerization of a Mutation in Escherichia Coli . . . ," 659–671 (Dec. 1978).
Goldblum, K. et al.: *J. Bacteriology*, 146:128–132 (Apr. 1981).
Slattery, E. et al.: *Proc. natl. Acad. Sci. USA*, 76(10):4778–4782 (Oct. 1979).
Nilsen, T.W. et al.: *J. Biol. Chem.*, 256(21):10751–10754 (Nov. 10, 1981).
Williams, B.R.G. et al.: *FEBS*, 105(1):47–52 (Sep. 1979).
Floyd–Smith, G.: *J. Cell. Biochem.*, 38:13–21 (1988).
Schmidt, A. et al.: *FEBS*, 95(2):257–264 (Nov. 1978).
Hovanessian, A.G. et al.: *Eur. J. Biochem.*, 84:149–159 (1978).
Clemens, M.J. et al. *Cell*, 13:565–572 (Mar. 1978).
Sen, G.C. et al.: *J. Biol. Chem.*, 267(8):5017–5020 (Mar. 15, 1992).
Nilsen, T.W. et al.: *Proc. Natl. Acad. Sci. USA*, 76(6):2600–2604 (Jun. 1979).
Ratner, L. et al.: *Eur. J. Biochem*, 79:565–577 (1977).
Baglioni, C. et al.: *J. Biol. Chem.*, 255(18):8390–8393 (Sep. 25, 1980).
Williams, B.R.G. et al.: *Nature*, 282(5739):582–586 (Dec. 6, 1979).
Williams, B.R.G. et al.: "The 2–5A (pppA2' p5'A2' p5' A) System in Interferon–treated and Control Cells".
Ratner, L. et al.: *Biochem. Biophys. Res. Commun.*, 81(3):947–954 (Apr. 14, 1978).
Coccia, E.M. et al.: *Virology*, 179:228–233 (1990).
Berg, J.M.: *J. Biol. Chem.*, 265(12):6513–6516 (Apr. 25, 1990).
Evans, R.M. et al.: *Cell*, 52:1–3 (Jan. 15, 1988).
Belasco, J. et al.: *Gene*, 72:15–23 (1988).
Fry, D.C. et al.: *Proc. Natl. Acad. Sci. USA*, 83:907–911 (Feb. 1986).
Walker, J.E. et al.: *EMBO*, 1(8):945–951 (1982).
Krupinski, J. et al.: *Science*, 244:1558–1564 (1989).
Au, D.C. et al.: *Biochem.*, 28:2772–2776 (1989).
Glaser, P. et al.: *EMBO*, 8(3):967–972 (1989).
Imai, J. et al.: *J. Biol. Chem.*, 260(3):1390–1393 (Feb. 10, 1985).
Watling, D. et al.: *EMBO*, 4(2):431–436 (1985).
Pestka, S. et al.: *Ann. Rev. Biochem.*, 56:727–777 (1987).
Lengyel, P.: *Ann. Rev. Biochem.*, 51:251–282 (1982).
Floyd–Smith, G. et al.: *Science*, 212:1030–1032 (May. 1981).
Deutscher, M.P.: *J. Biol. Chem.*, 268(18):13011–13014 (Jun. 25, 1993).
Cedergren, R. et al.: *FEBS*, 226(1)63–66 (Dec. 1987).
Farrell, P.J. et al.: *Proc. Natl. Acad. Sci. USA*, 75(12):5893–5897 (Dec. 1978).
Bisbal, C. et al.: *Eur. J. Biochem.*, 179:595–602 (1989).
Brawerman, G.: *Cell*, 57:9–10 (Apr. 7, 1989).
Mackie, G.A.: *J. Bacteriology*, 178(8)2488–2497 (Apr. 1991).
Xia, Z. et al.: *J. Biol. Chem.*, 265(12):6517–6520 (Apr. 25, 1990).

Saraste, M. et al.: *TIBS*, 15 (Nov. 1990).
Deutscher, M.P. et al.: *Cell*, 40:731–732 (Apr. 1985).
Cormack, R.S. et al.: *Proc. natl. Acad. Sci. USA*, 90:9006–9010 (Oct. 1993).
Bouvet, P. et al: *Nature*, 360:488–491 (Dec. 3, 1992).
Claverie–Martin, F. et al.: *J. Biol. Chem.*, 266(5):2843–2851 (Feb. 15, 1991).
Mudd, E.A. et al.: *EMBO*, 7(11):3601–3607 (1988).
Ehretsmann, C.P. et al.: *Genes & Develop.*, 6:149–159 (1992).
Taraseviciene, L. et al.: *Mol. Microbiol.*, 5(4):851–855 (1991).
Chauhan, A.K. et al.: *Nucleic Acids Res.*, 19(1)125–129 (1991).
Babitzke, P. et al.: *Proc. Natl. Acad. Sci. USA*, 88:1–5 (Jan. 1991).
Mudd, E.A. et al.: *Mol. Microbiol.*, 4(12):2127–2135 (1990).
Bouvet, P. et al. : *Nature*, 360:488–491 (Dec. 3, 1992).
Silverman, R.H. et al.: *Eur. J. Biochem.*, 124:131–138 (1982).
Hovanessian, A.G. et al.: *Meth. Enzymol.*, 79:184–199 (1981).
Goswami, B.B. et al.: *J. Biol. Chem.*, 259(3):1371–1374(Feb. 10, 1984).
Sharma, O.K. et al.: *Proc. Natl. Acad. Sci. USA*, 78(4):2221–2224 (Apr. 1981).
Goswami, B.B. et al.: *J. Biol. Chem.*, 257(12):6867–6870 (Jun. 25, 1982).
Sharma, O.K. et al.: *FEBS 0601*, 158(2):298–300 (Jul. 1983).
Sen, G.C. et al.: *J. Virology*, 45(3):1017–1027 (Mar. 1983).
Sen, G.C.: *J. gen. Virol.*, 64:2213–2220 (1983).
Sawaii, H. et al.: *J. Biochem.*, 101:339–346 (1987).
Taira, H. et al.: *J. Interf. Res.*, 5:583–596 (1985).
Salzberg, S. et al.: *Mol. Cell. Biol.*, 3(10):1759–1765 (Oct. 1983).
David, S. et al.: *J. Virology*, 63(3):1116–1122 (Mar. 1989).
Affabris, E. et al.: *Virology*, 125:508–512 (1983).
Mechti, N. et al.: *J. Biol. Chem.*, 259(5)3261–3265 (Mar. 10, 1984).
Miyamoto, N.G. et al.: *Virology*, 107:461–475 (1980).
Miyamoto, N.G. et al.: *J. Biol. Chem.*, 258(24):15232–15237 (Dec. 25, 1983).
Eppstein, D.A. et al.: *Virology*, 98:9–19 (1979).
Benech, P. et al.: *Mol. Cell. Biol.*, 7(12):4498–4504 (Dec. 1987).
Cohen, B. et al.: *EMBO*, 7(5):1411–1419 (1988).
Mory, Y. et al.: *J. Interf. Res.*, 9:295–304 (1989).
Imai, J. et al.: *J. Biol. Chem.*, 257(21):12739–12745 (Nov. 10, 1982).
Krause, D. et al.: *Eur. J. Biochem.*, 146:611–618 (1985).
Silverman, R.H. et al.: *Eur. J. Biochem.*, 115:79–85 (1981).
Wreschner, D.H. et al. *Eur. J. Biochem.*, 172:333–340 (1988).
Penn, L.J.Z. et al.: *J. Virology*, 49(3):748–753 (Mar. 1984).
Saunders, M.E. et al.: *EMBO*, 4(7):1761–1768 (1985).
Lesiak, K. et al.: *Biochem. Biophys. Res. Commun.*, 126(2):917–921 (Jan. 31, 1985).
Kitade, Y. et al.: *Nucl. Acids Res.*, 19(15):4103–4108 (1991).
Torrence, P.F. et al.: *FEB 04463*, 212(2):267–270 (Feb. 1987).
Alster, D. et al.: *Biochem. Biophys. Res. Commun.*, 141(2):555–561 (Dec. 15, 1986).
Lesiak, K. et al.: *J. Med. Chem.*, 1015–1022 (Jun. 1986).

Ilson, D.H. et al.: *J. Interf. Res.*, 6:05–12 (1986).
Torrence, P.F. et al.: *FEB 04463*, 212(2):267–270 (Feb. 1987).
Jamoulle, J.C. et al.: *Biochem.*, 23:3063–3069 (1984).
Imai, J. et al.: *Biochem.*, 23:766–774 (1984).
Eppstein, D.A. et al.: *J. Biol. Chem.*, 260(6):3666–3671 (Mar. 25, 1985).
Johnston, M.I. et al.: *Biochem. Biophys. Res. Commun.*, 97(2):375–383 (Nov. 28, 1980).
Torrence, P.F. et al.: *J. Med. Chem.*, 27:726–733 (1984).
Imai, J. et al.: *Org. Chem.*, 1418–1420 (May 3, 1985).
Silverman, R.H. et al.: *The Biology of the Interferon System 1984*, Kirchner et al., eds. 1985 Elsevier Science Publishers B.V., pp. 141–145.
Silverman, R. et al: In, *Interferons as cell growth inhibitors & antitumor factors.* (Friedman et al, eds.) A.R. Liss, NY, NY p. 143–150(1986).
Williams BRG, (1983). The Biochemical action of interferon. In: *Interferon and Cancer*, K Sikora ed, Elsevier, Amsterdam, pp. 33–52.
Doetsch, P.W. et al.: *Proc. Natl. Acad. Sci. USA*, 78:1–9 (1981).
Henderson, E.E. et al.: *Virology*, 122:198–201 (1982).
Wu, J.M. et al.: *Biochem. & Biophys. Res. Comm.*, 86(3):648–653 (1979).
Lee, C. et al.: *FEBS.* 157(1):205–209 (Jun. 1983).
Doetsch, P. et al.: *Nature*, 291:355–358 (May 1981).
Suhadolnik, R.J. et al.: *Biochemistry*, 22:4153–4158 (1983).
Kariko, K. et al.: *Biochemistry*, 26:7127–7135 (1987).
Kariko, K. et al.: *Biochemistry*, ; 26:7136–7142 (1987).
Suhadolnik, R.J. et al.: *Biochemistry*, 26:7143–7149 (1987).
Suhadolnik, R.J. et al.: *Biochemistry*, 27:8840–8846 (1988).
Suhadolnik, R.J. et al.: *Biochem. & Biophys. Res. Comm.*, 111(1):205–212 (1983).
Black, P.L. et al.: *J. Immun.*, 135(5):2773–2777(Nov. 1984).
Lee, C. et al.: *Biochemistry*, 24(3):551–555 (Jan. 1985).
Knight, M. et al.: *Meth. Enzymology*, 79:217–227 (1981).
Williams, B.R.G. et al.: *Meth. Enzymology*, 79:199–208 (1981).
Kerr, I.M. et al.: *Adv. Cyclic Nucleo. Res.*, 14:469–478.
Gribaudo, G. et al.: *J. Virol.*, 65(4):1478–1757 (Apr. 1991).
Suhadolnik, R.J. et al.: *Biochemistry*, 22(?):4153–4157 (1983).
Justesen, J. et al.: *Proc. Natl. Acad. Sci. USA*, 77:4618–4622 (1980).
Ono, M. et al.: *J. Mol. Biol.*, 129:343–357 (1979).
LeBleu, B. et al.: *Mechanisms of Interferon Action: Biochem. & Genetic Appr.*, 47–94.
Pai, E.F. et al.: *Nature*, 341:209–214 (Sep. 1989).
St. Laurent, G. et al.: *Cell*, 95–102 (1983).
Saraste, M. et al.: *TIBS*, 15:430–434 (Nov. 1990).
Rozen, F. et al.: *Mol. & Cell. Biol.*, 9(9):4061–4063 (Sep. 1989).
Schroder, H.C. et al.: *FASEB J.*, 4:3124–3130 (Oct. 1990).
Suhadolnik, R.J. et al.: Nucleosides, Nucleotides, and their Biol. Appl., pp. 147–179 (Academic Press 1983).
Torrence, P.F. et al.: *J. Medicinal Chem.*, 27(6):726–733 (1984).
Torrence, P.F. et al.: *Proc. Natl. Acad. Sci. USA*, 78(10):5993–5997 (Oct. 1981).
Torrence, P.F. et al.: *FEBS*, 130(2):291–296 (Aug. 1981).
Imai, J. et al.: *J. Biol. Chem.*, 257(21):12739–12745(Nov. 1982).
Morag, A. et al.: *Lancet*, p. 744 (Mar. 27, 1982).
Shulman, L. et al.: *Nature*, 288:98–100 (Nov. 1980).
Lesiak, K. et al.: *FEBS*, 151(2):291–296 (Jan. 1983).
de Clercq, E. et al.: *IUPHAR 9th Int'l Congress of Pharma.*, London 1984, Paton et al. eds. (vol. 1), pp. 307–317.
Williams, B.R.G. et al.: *Biol. of Interf. Syst.*, 1981 Elsevier, De Mayer et al. eds., pp. 111–114.
Silverman, R.H. et al.: In *Lymphokines & Interf.: A Practical Approach*, Clemens et al. eds., IRL Press, Wash. D.C. 1987, pp. 149–193.
Justensen, J. et al.: *Nucleic Acids Res.*, 8(14):? (1980).
Torrence, P.F. et al.: *Chemica Scripta*, 26:191–197 (1986).
Torrence, P.F. et al.: *Molec. Aspects Med.*, 5:129–171 (1982).
Chousterman, S. et al.: *J. Biol. Chem.*, 262(10):4806–4811 (Apr. 1987).
Chelbi–Alix, M.K. et al.: *J. Biol. Chem.*, 260(13):7960–7964 (Jul. 1985).
Besancon, F. et al.: *Biochem. & Biophys. Res. Comm.*, 103(1):16–24 (Nov. 1981).
Lab, M. et al.: *Biochem. & Biophys. Res. Comm.*, 105(2):412–418 (Mar. 1982).
Dougherty, J.P. et al.: *J. Biol. Chem.*, 255(9):3813–3816 (May 1980).
Mory, Y. et al.: *J. Interf. Res.*, 9:295–304 (1989).
Chebath, J. et al.: *Nature*, 330:587–588 (Dec. 1987).
Ghosh, S.K. et al.: *J. Biol. Chem.*, 266(23):15293–15299 (Aug. 1991).
Minks, M.A. et al.: *J. Biol. Chem.*, 254(20):10180–10183 (Oct. 1979).
Wu, J.M. et al.: *AIDS Res.*, 2(2):127–131 (1986).
Schroder, H.C. et al.: *J. Biol. Chem.*, 264(10):5669–5673 (Apr. 1989).
Schroder, H.C. et al.: *AIDS Res. & Human Retrov.*, 6(5):659–672 (1990).
Schroder, H.C. et al.: *Biol. Chem. Hoppe–Seyler*, 369:985–995 (Sep. 1988).
Agy, M.B. et al.: *Virology*, 177:251–258 (1990).
Suhaldolnik, R.J. et al.: *Photoaffinity*, 27(24):8840–8846 (1988).
Read, S.E. et al.: *J. Infect. Dis.*, 152(3):466–472 (Sep. 1985).
Ghora, B.K. et al.: *Cell*, 15:1055–1066 (Nov. 1978).
Samanta, H. et al.: *J. Biol. Chem.*, 255(20)9807–9813 (Oct. 1980).
Broeze, R.J. et al.: *J. Interf. Res.*, 1(2):191–201 (1981).
Yang, K. et al.: *J. Biol. Chem.*, 256(17):9324–9328 (Sep. 1981).
Cayley, P.J. et al.: *Eur. J. Biochem.*, 143:165–174 (1984).
Brown, R.E. et al.: *Meth. in Enzymlogy*, 79:208–216 (1981).
Hersh, C.L. et al.: *J. Biol. Chem.*, 259(3):1731–1737 (Feb. 1984).
Rice, A.P. et al.: *J. Virol.*, 50(1):220–228 (Apr. 1984).
Rice, A.P. et al: *J. Virol.*, 56(3):1041–1044 (Dec. 1985).
Williams, B.R.G. et al.: *Eur. J. Biochem.*, 92:455–462 (1978).
Cayley, P.J. et al.: *Eur. J. Biochem.*, 122:601–608 (1982).
Reid, T.R. et al.: *Anal. Biochem.*, 136:136–141 (1984).
Williams, B.R.G. et al.: *Nucleic Acids Res.*, 6(4):1335–1350 (Apr. 1979).
Foster, G.R. et al.: *Proc. natl. Acad. Sci. USA*, 88:2888–2892 (Apr. 1991).
Cayley, P.J. et al.: *Eur. J. Biochem.*, 122:601–608 (1982).
Cayley, P.J. et al.: *Interferons*, ??:143–157 (Academic Press 1992).
Lebleu, B. et al.: *Proc. Natl. Acad. Sci. USA*, 73(9):3107–3111 (Sep. 1976).
Bisbal, C. et al.: *Biochemistry*, 26:5172–5178 (1987).

Mechti, N. et al.: *Differentiation*, 29:136–139 (1985).
Bayard, B. et al.: *Biochemistry*, 25:3730–3736 (1986).
Stark, G.R. et al.: *Nature*, 278:471–473 (Mar. 1979).
Hovanessian, A.G. et al.: *Proc. Natl. Acad. Sci. USA*, 76(&):3261–3265 (Jul. 1979).
Buffet–Janvresse, C. et al.: *J. Interf. Res.*, 6:85–96 (1986).
Ogunkolade, W. et al.: *J. Interf. Res.*, 7:245–254 (1987).
Riviere, Y. et al.: *Ann. Immunol. (Inst. Pasteur)*, 135(C):333–343 (1984).
Marcovistz, R. et al.: *J. gen. Virol.*, 65:995–997 (1984).
Hovanessian, A.G. et al.: *Virology*, 104:195–204 (1980).
Laurence, L. et al.: *Virology*, 143:290–299 (1985).
Chapekar, M.S. et al.: *Biochem. & Biophys. Res. Commun.*, 151(3):1180–1187 (Mar. 1988).
Floyd–Smith, G. et al.: *Proc. of Soc. for Exper. Bio. & Medicine*, 189:329–337 (1988).
Esteban, M. et al.: *J. gen. Virol.*, 67:801–808 (1986).
Paez, E. et al.: *J. Virol.*, 56(1):75–84 (Oct. 1985).
Paez, E. et al.: *Virology*, 134:12–28 (1984).
Paez, E. et al.: *Virology*, 134:29–39 (1984).
Esteban, M. et al.: *Virology*, 134:40–51 (1984).
Santoro, M.G. et al.: *Biochem. & Biophys Res. Commun.*, 116(2):442–448 (Oct. 1983).
Benavente, J. et al.: *J. Virol.*, 51(3):866–871 (Sep. 1984).
Eppstein, D.A. et al.: *Nature*, 302:723–724 (Apr. 1983).
Eppstein, D.A. et al.: *Virology*, 131:341–354 (1983).
Eppstein, D.A. et al.: *J. Interf. Res.*, 3(3):305–311 (1983).
Eppstein, D.A. et al.: *J. Biol. Chem.*, 261(13):5999–6003 (May 1986).
Drocourt, J. et al.: *Nucleic Acids Res.*, 10(6):2163–2174 (1982).
Rice, A.P. et al.: *J. Virol.*, 54(3):894–898 (Jun. 1985).
Jamoulle, J.–C. et al.: *Biochemistry*, 26:376–383 (1987).
Torrence, P.F. et al: *Analyt. Biochem.*, 129:103–110 (1983).
Johnston, M.I. et al.: *J. Biol. Chem.*, 262(17):8377–8382 (Jun. 1987).
Mittnacht, S. et al.: *J. gen. Virol.*, 68:2945–2951 (1987).
Defilippi, P. et al.: *FEBS 3525*, 198(2):326–332 (Mar. 1986).
Ankel, H. et al.: *J. gen. Virol.*, 66:2355–2364 (1985).
Hovanessian, A.G.: *J. Interf. Res.*, 11:199–205 (1991).
Marie, I. et al.: *J. Biol. Chem.*, 267(14):9933–9939 (1992).
Hovanessian, A.G. et al.: *Virology*, 101:81–90 (1980).
Hovanessian, A.G. et al.: *EMBO*, 6(5):1273–1280 (1987).
Flenniken, A.M. et al.: *J. Virol.*, 62(9):3077–3083 (Sep. 1988).
Wood, J.N. et al.: *Nature*, 282:74–76 (Nov. 1979).
Hovanessian, A.G. et al.: *J. Interf. Res.*, 1(2):179–190 (1981).
Hovanessian, A.G. et al.: *Proc. Natl. Acad. Sci. USA*, 76(7):3261–3265 (Jul. 1979).
Galabru, J. et al.: *J. gen. Virol.*, 66:711–718 (1985).
Buffet–Janvresse, C. et al.: *Proc. of Soc. for Exp. Biol. & Medicine*, 175:169–175 (1984).
Knight Jr., E. et al.: *Proc. Natl. Acad. Sci. USA*, 82:1151–1154 (Feb. 1985).
Kimchi, A.: *J. Interf. Res.*, 1(4):559–569 (1981).
Cleveland, D.W. et al.: *J. Biol. Chem.*, 252(3):1102–1106 (Feb. 1977).
Bayard, B. et al.: *Eur. J. Biochem.*, 142:291–298 (1984).
Bisbal, C. et al., *Biochemistry*, 26:5172–5178 (1987).
Bayard, B. et al.: *Eur. J. Biochem.*, 151:319–325 (1985).
Bayard, B. et al.: *Biochemistry*, 25:3730–3736 (1986).
Baglioni, C. et al.: *Biochemistry*, 18(9):1765–1770 (1979).
Nilsen, T.W. et al.: *J. Virol.*, 42(3):1039–1045 (Jun. 1982).
Baglioni, C. et al.: *J. Biol. Chem.*, 256(7):3253–3257 (Apr. 1981).
Nilsen, T.W. et al.: *Biochemistry*, 19:5574–5579 (1980).
Baglioni, C. et al.: *Biochemistry*, 20:758–762 (1981).
Nilsen, T.W. et al.: *Virology*, 122:498–502 (1982).
Nilsen, T.W. et al.: *Molecular & Cellular Biol.*, 3(1):64–69 (Jan. 1983).
Baglioni, C. et al.: *Cell*, 17:255–264 (Jun. 1979).
Nilsen, T.W. et al.: *Molecular & Cellular Biol.*, 2(2):154–160 (Feb. 1982).
Baglioni, C. et al.: *J. Virol.*, 52(3):865–871 (Dec. 1984).
Williams, G.J. et al.: *Virology*, 151:233–242 (1986).
Minks, M.A. et al.: *Nucleic Acids Res.*, 6(2):767–780 (Feb. 1979).
Baglioni, C.: Chapter 8, *The Molecular Mediators of Interferon Action*, pp. 153–168.
Nilsen, T.W. et al.: *J. Biol. Chem.*, 256(15):7806–7811 (Aug. 1981).
Nilsen, T. W. et al.: *J. Biol. Chem.*, 257(4):1602–1605 (Feb. 1982).
Verhagen, M. et al.: *Proc. Natl. Acad. Sci. USA*, 77(8):4479–4483 (Aug. 1980).
Verhagen–Lewalle, M. et al.: *Eur. J. Biochem.*, 126:639–643 (1982).
Vandenbussche, P. et al.: *Virology*, 111:11–22 (1981).
Chebath, J. et al.: *Nature*, 330:587–588 (Dec. 1987).
Chebath, J. et al.: *J. Biol. Chem.*, 262(8):3852–3857 (1987).
Sperling, J. et al.: *Proc. Natl. Acad. Sci. USA*, 88:10377–10381 (Dec. 1991).
Alarcon, B. et al.: *J. Virol.*, 52(1):183–187 (Oct. 1984).
Cailla, H. et al.: *Radioimmunoassay and Related Procedures in Medicine 1982*, Int'l Atomic Energy Agency Vienna, 1982.
Cailla, H. et al.: *Proc. Natl. Acad. Sci. USA*, 79:4742–4746 (Aug. 1982).
Marti, J. et al.: *Nucleosides & Nucleotides*, 7(4):479–495 (1988).
Trujillo, M.A. et al.: *Eur. J. Biochem.*, 169:167–173 (1987).
Laurence, L. et al.: *Proc. Natl. Acad. Sci. USA*, 81:2322–2326 (Apr. 1984).
Hovanessian, A.G. et al.: *Eur. J. Biochem.*, 93:515–526 (1979).
Kerr, I.M. et al.: *The Biology of the Interferon System 1983*, Elsevier: De Maeyer et al. eds., pp. 213–222.
Etienne–Smekens, M. et al.: *FEBS L.*, 125(2):146–150 (Mar. 1981).
Smekens–Etienne, M. et al.: *Eur. J. Biochem.*, 130:269–273 (1983).
Wathelet, M. et al.: *FEBS L.*, 196(1):113–120 (Feb. 1986).
Verhaegen–Lewalle, M. et al.: *J. Virol.*, ?:425–434 (1981).
Haugh, M.C. et al.: *Eur. J. Biochem.*, 132:77–84 (1983).
Martin, E.M. et al.: *Eur. J. Biochem.*, 95:295–307 (1979).
Squire, J. et al.: *Genomics*, 19:174–175 (1994).
Fujihara, M. et al.: *J. Interf. Res.*, 9:691–707 (1989).
Squire, J. et al.: *Genomics* (Dec.), pp. 17–19.
Hassel, B.A. et al.: *EMBO*, 12(8):3297–3304 (1993).
Nilsen, T.W. et al.: *Nature*, 286:178–181 (Jul. 1980).
Krishnan, I. et al.: *Nature*, 285:485–488 (Jun. 1980).
Krishnan, I. et al.: *Mol. & Cell. Biol.*, 1(10):932–938 (Oct. 1981).
Krishnan, I. et al.: *Proc. Natl. Acad. Sci. USA*, 77(11):6506–6510 (Nov. 1980).
Krishnan, I. et al.: *Virology*, 111:666–670 (1981).
Minks, M.A. et al.: *J. Biol. Chem.*, 254(12):5058–5064 (Jun. 1979).

Minks, M.A. et al.: *J. Biol. Chem.,* 255(13):6403–6407 (Jul. 1980).
West, D.K. et al.: *Mol. & Cell. Biol.,* 2(11):1436–1443 (Nov. 1982).
Ball, L.A.: *Virology,* 94:282–296 (1979).
Ball, L.A. et al.: *Proc. Natl. Acad. Sci. USA,* 75(3):1167–1171 (Mar. 1978).
Creasey, A.A. et al.: In press, *Molecular and Cellular Biology* (1983), pp. 1–28.
Eds. William, B.R.G. and Silverman, R.H.: *The 2–5A System,* Proc. of 6th Int'l Symp. of Res. Inst. Hosp. for Sick Children, Toronto, Ontario, Canada, Jun. 3–5, 1985.

Young, et al.: *Science,* 222:778–782 (1983).
Gerald, et al.: *Biochem Biophys Acta.,* 866:1–14 (1986).
Murhammer, et al.: *Appl. Biochem. Biotechnol.,* 31:283–310 (1991).
Hassel et al., J. Interferon Res. 12(Suppl. 1):542 (1992).
Zhou et al., J. Interferon Res. 12 (Suppl. 1): 557 (1992).
Zhou et al., Cell 72:753–765 (1993).
Silverman et al., J. Biol. Chem. 263:7336–7341 (1988).
Floyd–Smith et al., Meth. Enzymol. 119:489–499 (1986).
Silverman et al., J. Cell. Biochem., Suppl. 16B:163 (1992).
Hassel et al., J. Cell. Biochem., Suppl. 17C:177 (1993).

THE 2-5A SYSTEM

FIG. 3B1

```
     -103 aatcccaacttacactcaaagctt
cttgattaagtgctaggagataaattgcattctcaaggaaaagctaaaagtggtagcaggtggcatttaccgtc ATG GAG AGC AGG GAT CAT AAC AAC CCC CAG GAG GGA CCC ACG TCC TCC AGC GGT AGA AGG     60
Met Glu Ser Arg Asp His Asn Asn Pro Gln Glu Gly Pro Thr Ser Ser Ser Gly Arg Arg     20

GCT GCA GTG GAA GAC AAT CAC TTG CTG ATT AAA GCT GTT CAA AAC GAA GAT GTT GAC CTG    120
Ala Ala Val Glu Asp Asn His Leu Leu Ile Lys Ala Val Gln Asn Glu Asp Val Asp Leu     40

GTC CAG CAA TTG CTG GAA GGT GGA GCC AAT GTT AAT TTC CAG GAA GAG GAA GGG GGC TGG    180
Val Gln Gln Leu Leu Glu Gly Gly Ala Asn Val Asn Phe Gln Glu Glu Glu Gly Gly Trp     60

ACA CCT CTG CAT AAC GCA GTA CAA ATG AGC AGG GAG GAC ATT GTG GAA CTT CTG CTT CGT    240
Thr Pro Leu His Asn Ala Val Gln Met Ser Arg Glu Asp Ile Val Glu Leu Leu Leu Arg     80

CAT GGT GCT GAC CCT GTT CTG AGG AAG AAT GGG GCC ACG CTT TTT ATC CTC GCA GCG        300
His Gly Ala Asp Pro Val Leu Arg Lys Asn Gly Ala Thr Leu Phe Ile Leu Ala Ala        100

ATT GCG GGG AGC GTG AAG CTG CTG AAA CTT TTC TCT AAA GGA GCA GAT GTC AAT GAG        360
Ile Ala Gly Ser Val Lys Leu Leu Lys Leu Phe Ser Lys Gly Ala Asp Val Asn Glu        120

TGT GAT TTT TAT GGC TTC ACA GCC TTC ATG GAA GCC GCT GTG TAT GGT AAG GTG AAA GCC    420
Cys Asp Phe Tyr Gly Phe Thr Ala Phe Met Glu Ala Ala Val Tyr Gly Lys Val Lys Ala    140

CTA AAA TTC CTT TAT AAG AGA GCA AAT GTG GCA AAT GTG AGG CGA AAG ACA AAG GAG GAT    480
Leu Lys Phe Leu Tyr Lys Arg Ala Asn Val Ala Asn Val Arg Arg Lys Thr Lys Glu Asp    160

CAA GAG CGG CTG AGG AAA GGG CTG GCC ACA GCT CTC ATG GAC GCT GAA AAA GGA CAC        540
Gln Glu Arg Leu Arg Lys Gly Leu Ala Thr Ala Leu Met Asp Ala Glu Ala Glu Lys Gly His    180

GTA GAG GTC TTG AAG ATT CTC CTT GAT GAG ATG GGG GCA GAT GTA AAC GCC TGT GAC AAT    600
Val Glu Val Leu Lys Ile Leu Leu Asp Glu Met Gly Ala Asp Val Asn Ala Cys Asp Asn    200
```

FIG. 3B2

```
ATG GGC AGA AAT GCC TTG ATC CAT GCT CTC CTG AGC TCT GAC GAT AGT GAT GTG GAG GCT    660
Met Gly Arg Asn Ala Leu Ile His Ala Leu Leu Ser Ser Asp Asp Ser Asp Val Glu Ala    220

ATT ACG CAT CTG CTG CTC GAC CAT GGG GCT CAT GTC GAT GTC AAT GTG AGG GAA AGA GGG AAG    720
Ile Thr His Leu Leu Leu Asp His Gly Ala His Val Asp Val Asn Val Arg Glu Arg Gly Lys    240

ACT CCC CTG ATC CTG GCA GTG GAG AAG AAG CAC TTG GGT TTG GTG CAG AGG CTT CTG GAG    780
Thr Pro Leu Ile Leu Ala Val Glu Lys Lys His Leu Gly Leu Val Gln Arg Leu Leu Glu    260

CAA GAG CAC ATA GAG ATT AAT GAC ACA GCA AGT GAT GGC AAA ACA GCA CTG CTG CTT GCT    840
Gln Glu His Ile Glu Ile Asn Asp Thr Ala Ser Asp Gly Lys Thr Ala Leu Leu Leu Ala    280

GTT GAA CTC AAA CTG AAG AAA ATC GCC GAG TTG TGC AAA CGT GGA GCC AGT ACA GAT    900
Val Glu Leu Lys Leu Lys Lys Ile Ala Glu Leu Cys Lys Arg Gly Ala Ser Thr Asp    300

TGT GGG GAT CTT GTT ATG ACA GCG AGG CGG AAT TAT GAC CAT TCC CTT GTG AAG GTT CTT    960
Cys Gly Asp Leu Val Met Thr Ala Arg Arg Asn Tyr Asp His Ser Leu Val Lys Val Leu    320

CTC TCT CAT GGA GCC AAA GAA GAT TTT CAC CCT CCT GCT GCA GAC TGG AAG CCT CAG AGC    1020
Leu Ser His Gly Ala Lys Glu Asp Phe His Pro Pro Ala Glu Asp Trp Lys Pro Gln Ser    340

TCA CAC TGG GGG GCA GCC CTG AAG GAT CTC CAC AGA ATA TAC CGC CCT ATG ATT GGC AAA    1080
Ser His Trp Gly Ala Ala Leu Lys Asp Leu His Arg Ile Tyr Arg Pro Met Ile Gly Lys    360

CTC AAG TTC TTT ATT GAT GAA AAA TAC AAA ATT GCT GAT ACT TCA GAA GGA GGC ATC TAC    1140
Leu Lys Phe Phe Ile Asp Glu Lys Tyr Lys Ile Ala Asp Thr Ser Glu Gly Gly Ile Tyr    380

CTG GGG TTC TAT GAG TTC GAA AAG CAA GAA GTA GCT GTG CAG AAG ACG TTC TGT GAG GGC AGC CCA CGT    1200
Leu Gly Phe Tyr Glu Phe Glu Lys Gln Glu Val Ala Val Lys Thr Phe Cys Glu Gly Ser Pro Arg    400

GCA CAG CGG GAA GTC TCT TGT CTG CAA AGC AGC CGA GAG AAC AGT CAC TTG GTG ACA TTC    1260
Ala Gln Arg Glu Val Ser Cys Leu Gln Ser Ser Arg Glu Asn Ser His Leu Val Thr Phe    420
```

FIG. 3B3

```
TAT GGG AGT GAG AGC CAC AGG GGC CAC TTG TTT GTG TGT ACC CTC TGT GAG CAG ACT    1320
Tyr Gly Ser Glu Ser His Arg Gly His Leu Phe Val Cys Val Thr Leu Cys Glu Gln Thr  440

CTG GAA GCG TGT TTG GAT GTG CAC AGA GGG GAA GAT GTG GAA AAT GAG GAA GAT GAA TTT  1380
Leu Glu Ala Cys Leu Asp Val His Arg Gly Glu Asp Val Glu Asn Glu Glu Asp Glu Phe  460

GCC CGA AAT GTC CTG TCA TCT ATA TTT AAG GCT GTT CAA GAA CTA CAC TTG TCC TGT GGA  1440
Ala Arg Asn Val Leu Ser Ser Ile Phe Lys Ala Val Gln Glu Leu His Leu Ser Cys Gly  480

TAC ACC CAC CAG GAT CTG CAA CCA CAA AAC ATC TTA ATA GAT TCT AAG AAA CGT GCT CAC  1500
Tyr Thr His Gln Asp Leu Gln Pro Gln Asn Ile Leu Ile Asp Ser Lys Lys Arg Ala His  500

CTG GCA GAT TTT GAT AAG AGC ATC AAG TGG GCT GGA GAT CCA AAG GGA GAA GTC AAG AGA GAT  1560
Leu Ala Asp Phe Asp Lys Ser Ile Lys Trp Ala Gly Asp Pro Lys Gly Glu Val Lys Arg Asp  520

CTA GAG GAC CTT GGA CGG CTG GTC TAT GTG GTA AAG CTT TCT CCA GAT GAG GAA ACT AAG  1620
Leu Glu Asp Leu Gly Arg Leu Val Leu Tyr Val Val Lys Leu Ser Pro Asp Glu Glu Thr Lys  540

GAT CTG AAA GCT CAA AGT AAT GAA GAG GTG GTT CAA GTT CAA CTT TCT CCA GAT GAG GAA ACT AAG  1680
Asp Leu Lys Ala Gln Ser Asn Glu Glu Val Val Gln Val Leu Ser Pro Asp Glu Glu Thr Lys  560

GAC CTC ATT CAT CGT CTC TTC CAT CCT GGG GAA CAT GTG AGG GAC TGT CTG AGT GAC CTG  1740
Asp Leu Ile His Arg Leu Phe His Pro Gly Glu His Val Arg Asp Cys Leu Ser Asp Leu  580

CTG GGT CAT CCC TTC TTT TGG ACT CGA TGG GAG AGC CGC TAT AGG ACG CTT CGG AAT GTG GGA  1800
Leu Gly His Pro Phe Phe Trp Thr Arg Trp Glu Ser Arg Tyr Arg Thr Leu Arg Asn Val Gly  600

AAT GAA TCC GAC ATC AAA ACA CGA AAA TCT GAA AGT GAG ATC CTC AGA CTA CTG CAA CCT  1860
Asn Glu Ser Asp Ile Lys Thr Arg Lys Ser Glu Ser Glu Ile Leu Arg Leu Leu Gln Pro  620

GGG CCT TCT GAA CAT TCC AAA AGT TTT GAC AAG TGG ACG ACT AAG ATT AAT GAA TGT GTT  1920
Gly Pro Ser Glu His Ser Lys Ser Phe Asp Lys Trp Thr Thr Lys Ile Asn Glu Cys Val  640
```

FIG. 3B4

| | | |
|---|---|---|
| ATG AAA AAA ATG AAT AAG TTT TAT GAA AAA AGA GGC AAT TTC TAC CAG AAC ACT GTG GGT | 1980 | |
| Met Lys Lys Met Asn Lys Phe Tyr Glu Lys Arg Gly Asn Phe Tyr Gln Asn Thr Val Gly | 660 | |
| GAT CTG CTA AAG TTC ATC CGG AAT TTG GGA GAA CAC ATT GAT GAA AAG CAT AAA AAG | 2040 | |
| Asp Leu Leu Lys Phe Ile Arg Asn Leu Gly Glu His Ile Asp Glu Lys His Lys Lys | 680 | |
| ATG AAA TTA AAA ATT GGA GAC CCT TCC CTG TAT TTT CAG AAG ACA TTT CCA GAT CTG GTG | 2100 | |
| Met Lys Leu Lys Ile Gly Asp Pro Ser Leu Tyr Phe Gln Lys Thr Phe Pro Asp Leu Val | 700 | |
| ATC TAT GTC TAC ACA AAA CTA CAG AAC ACA GAA TAT AGA AAG CAT TTC CCC CAA ACC CAC | 2160 | |
| Ile Tyr Val Tyr Thr Lys Leu Gln Asn Thr Glu Tyr Arg Lys His Phe Pro Gln Thr His | 720 | |
| AGT CCA AAC AAA CCT CAG TGT GAT GGA GCT GGT GGG GCC AGT GGG TTG GCC AGC CCT GGG | 2220 | |
| Ser Pro Asn Lys Pro Gln Cys Asp Gly Ala Gly Gly Ala Ser Gly Leu Ala Ser Pro Gly | 740 | |
| TGC 2223  tgatgactgattgctgagttcaggaactacttattagctgtagagtccttgcaaatcacaacat | 2292 | |
| Cys 741 | | |
| tctgggcctttaactcaccaggttgcttgtgagggatgagttgcatagctgatatgtcagtccctgcatcgtg | 2367 | |
| tattccatatgtctataacaaaagcaatatatatccagactacacagtccataagctttaccactaactggga | 2442 | |
| ggacattctgctaagatcctttgtcaattgcaccaaaagaatgagtgcctgacccctaatgctgcatatgtt | 2517 | |
| acaattctctcacttaatttcccaatgatcttgcccaagattatcaattatatacctagcactttataaatt | 2592 | |
| tgagactcagagagtgtgagctactggcacctaaaactcaatctcttccaggctcttccagatgaggcccaaacat | 2667 | |
| ttattggtacctctcattgggcaccttaaaactcattcattcattcattgagcatctcagtattcattatgtggtg | 2742 | |
| atataggggttccaggaatctcattcattcattcattgagcatctcagtataagtctgggactggatg | 2817 | |
| catgaatt 2825 | | |

FIG. 4A

P-loop cores- ▉   Cys-rich- ▨   PK homology- ▨

```
Human    - MESRDHNNPQ EGPTSSSGRR AAVEDNHLLI KAVQNEDVDL VQQLLEGGAN VNFQEEEGGW  60
           ::  :  ::         :       :           ::       ::            ::
Murine   - METPDYNTPQ GGTPSAGSQR TVVEDDSSLI KAVQKGDVVR VQQLLEKGAD ANACEDTWGW  60

Human    - TPLHNAVQMS REDIVELLLR HGADPVLRKK NGATLFILAA IAGSVKLLKL FLSKGADVNE 120
           :::::::::         :::  ::::: :::  :::: ::::         :: :: ::::::
Murine   - TPLHNAVQAG RVDIVNLLLS HGADPHRRKK NGATPFIIAG IQGDVKLLEI LLSCGADVNE 120

Human    - CDFYGFTAFM EAAVYGKVKA LKFLYKRGAN VNLRRKTKED QERLRKGGAT ALMDAAAEKGH 180
           ::  :::::: ::  ::::     :: ::::  ::: :: :   ::: : ::: ::: ::::::
Murine   - CDENGFTAFM EAAERGNAEA LRFLFAKGAN VNLRRQTTKD KRRLKQGGAT ALMSAAAEKGH 180

Human    - VEVLKILLDE MGADVNACDN MGRNALIHAL LSSDDSDVEA ITHLLLDHGA DVNVRGERGK 240
                 :::    ::::::: :: :::::: :               ::   ::  :::::::::
Murine   - LEVLRILLND MKAEVDARDN MGRNALIRTL LNWDCENVEE ITSILIQHGA DVNVRGERGK 240

Human    - TPLILAVEKK HLGLVQRLLE QEHIEINDTD SDGKTALLLA VELKLKKIAE LLCKRGASTD 300
           :::::: ::: ::::: ::    :         ::::::::   ::: ::  :  ::
Murine   - TPLIAAVERK HTGLVQMLLS REGINIDARD NEGKTALLIA VDKQLKEIVQ LLLEKGA-DK 299

Human    - CGDLVMTARR NYDHSLVKVL LSHGAKEDFH PPAEDWKPQS SHWGAALKDL HRIYRPMIGK 360
           :::::: ::: :  :::::::  ::         :                     :::::::
Murine   - CDDLVWIARR NHDYHLVKLL LPYVANPDTD PPAGDWSPHS SRWGTALKSL HSMTRPMIGK 359

Human    - LKFFIDEKYK IADTSEGGIY LGFYEKQEVA VKTFCEGSPR AQREVSCLQS SRENSHLVTF 420
           ::: :: ::  ::::::  :  ::  : :::  :::: : ::  :::::::
Murine   - LKIFIHDDYK IAGTSEGAVY LGIYDNREVA VKVFRENSPR GCKEVSCLRD CGDHSNLVAF 419
```

FIG. 4B

```
Human   - YGSESHRGHL FVCVTLCEQT LEACLDVHRG EDVENEEDEF ARNVLSSIFK AVQELHLSCG        480
           ::: :::::: ::  ::  ::  ::       ::   ::  ::    ::: :::
Murine  - YGREDDKGCL YVCVSLCEWT LEEFLRLPRE EPVENGEDKF AHSILLSIFE GVQKLHLH-G        478

Human   - YTHQDLQPQN ILIDSKKRAH LADFDKSIKW AGDPQEVKRD LEDLGRLVLY VVKKGSISFE        540
           :: :::::: :::::: ::  ::::  ::     ::   ::  ::::::::::  ::   ::::
Murine  - YSHQDLQPQN ILIDSKKAVR LADFDQSIRW MGESQMVRRD LEDLGRLVLY VVMKGEIPFE        538

Human   - DLKAQSNEEV VQLSPDEETK DLIHRLFHPG EHVRDCLSDL LGHPFFWTWE SRYRTLRNVG        600
           :::  :::: :  ::::::: ::::   ::    ::  :: ::  :::::::::  :::::::::
Murine  - TLKTQNDEVL LTMSPDEETK DLIHCLFSPG ENVKNCLVDL LGHPFFWTWE NRYRTLRNVG        598

Human   - NESDIKTRKS ESEILRLLQP GPSEHSKSFD KWTTKINECV MKKMNKFYEK R-GNFYQNTV        659
           :::::   :  ::  :::::   ::   :::   ::::  :    ::   ::::   :  ::  ::
Murine  - NESDIKVRKC KSDLLRLLQH QTLEPPRSFD QWTSKIDKNV MDEMNHFYEK RKKNPYQDTV        658

Human   - GDLLKFIRNL GEHIDEEKHK KMKLKIGDPS LYFQKTFPDL VIYVYTKLQN TEYRKHFPQT        719
           :::::::::: ::::::  ::
Murine  - GDLLKFIRNI GEHINEEKKR G-----------------------------------------       679

Human   - HSPNKPQCDG AGGASGLASP GC        741
```

*ID SEQ NO:5:

FIG. 10A

| ANKYRIN CONSENSUS: | | -G- TPLHψAA--GH---ψV---LL---GA---D---- |
|---|---|---|
| | | S A A N |
| REPEAT 1 | HUMAN 58 | GG W TPLHNAVQMSREDIVELLLRHGADPVLRKK 90 |
| | MURINE | WG WTPLHNAVQAGRVDIVNLLLSHGADPHRRKK |
| REPEAT 2 | HUMAN 91 | NG ATLFILAAIAGSVKLLLKFLLSKGADVNECDF 123 |
| | MURINE | NG ATIPFIIIAGIQGDVKLLLEILLSCGADVNECDE |
| REPEAT 3 | HUMAN 124 | YG FTAFMEAAYYGKVKALKFLLYKRGANVNLRRK 156 |
| | MURINE | NG FTAFMEAAERGNAEALRFLLFAKGANVNLRRQ |
| REPEAT 4 | HUMAN 238 | RG KTPLILAVEKKHLGLVQRLLEQEHIEINDTD 270 |
| | MURINE | RG KTPLIAAVERKHTGLVQMLLSREGINIDARD |

FIG. 10B

Ankyrin repeats (1, 2, 3, 4) — 2-5A — Cys$_X$ — PK — Required for RNase activity Amino acid number: 0, 100, 200, 300, 400, 500, 600, 700

NH$_2$- ... -COOH

ANIMAL 2-5A DEPENDENT RNASES

This is a continuation of application Ser. No. 08/028,086 filed on Mar. 8, 1983 now abandoned.

FIELD OF THE INVENTION

The present invention relates to isolated 2-5A-dependent RNases having the ability to bind 2-5A and/or cleave single stranded RNA when bound to 2-5A, encoding sequences therefor, recombinant nucleotide molecules, recombinant vectors and recombinant cells.

BACKGROUND

Control of RNA degradation is a critical cell function, and gene expression is often regulated at the level of RNA stability. See, e.g., Shaw, G. and Kamen, R., *Cell*, 46: 659–667 (1986). Nevertheless, relatively little is known about the biochemical pathways that mediate RNA degradation in mammalian systems. For instance, most if not all of the ribonucleases responsible for mRNA turnover in mammalian cells remain unidentified. This was reviewed in Brawerman, G., *Cell*, 57: 9–10 (1989). Presently, the 2-5A system is believed to be the only well-characterized RNA degradation pathway from higher animals including man. See FIG. 1. See also, .e.g., Kerr, I. M. and Brown, R. E., *Prod. Natl. Acad. Sci. U.S.A.*, 75: 256–260 (1978) and Cayley, P. J. et al., *Biochem Biophys Res. Commun.*, 108: 1243–1250 (1982); reviewed in Sen, G. C. and Lengyel, P., *J. Biol. Chem.*, 267: 5017–5020 (1992). The activity of the 2-5A system is believed to be mediated by an endoribonuclease known as 2-5A-dependent RNase. See Clemens, M. J. and Williams, B. R. G., *Cell*, 13: 565–572 (1978). 2-5A-dependent RNase is a unique enzyme in that it requires 2-5A, unusual oligoadenylates with 2',5' phosphodiester linkages, $p_n(A2'p)_nA$, for ribonuclease activity. See Kerr, I. M. and Brown, R. E., *Proc. Natl. Acad. Sci. U.S.A.*, 75: 256–260 (1978). 2-5A is produced from ATP by a family of synthetases in reactions requiring double-stranded RNA (dsRNA). See FIG. 1. See also Hovanessian, A. G. et al., *Nature*, 268: 537–539 (1977); Marie, I. and Hovanessian, A. G., *J. Biol. Chem.*, 267: 9933–9939 (1992). 2-5A is unstable in cells and in cell-free systems due to the combined action of 2',5'-phosphodiesterase and 5'-phosphatase. See Williams, B. R. G. et al.; *Eur. J. Biochem.*, 92: 455–562 (1978); and Johnson, M. I. and Hearl, W. G., *J. Biol. Chem.*, 262: 8377–8382 (1987). The interaction of 2-5A-dependent RNase and 2-5A($K_d$=4×10$^{-11}$M), Silverman, R. H. et al., *J. Biol. Chem.*, 263: 7336–7341 (1988), is highly specific. See Knight, M. et al., *Nature*, 288: 189–192 (1980). 2-5A-dependent RNase is believed to have no detectable RNase activity until it is converted to its active state by binding to 2-5A. See Silverman, R. H., *Anal. Biochem.*, 144: 450–460 (1985). Activated 2-5A-dependent RNase cleaves single-stranded regions of RNA 3' of UpNp, with preference for UU and UA sequences. See Wreschner, D. H. et al., *Nature*, 289: 414–417 (1981a); and Floyd-Smith, G. et al., *Science*, 212: 1020–1032 (1981). Analysis of inactive 2-5A-dependent RNase from mouse liver revealed it to be a single polypeptide of approximately 80 kDa. See Silverman, R. H. et al., *J. Biol. Chem.*, 263: 7336–7341 (1988).

Although the full scope and biological significance of the 2-5A system remains unknown, studies on the molecular mechanisms of interferon action have provided at least some of the functions. Interferons α, β or γ are believed to induce the accumulation of both 2-5A-dependent RNase, Jacobsen, H. et al., *Virology*, 125: 496–501 (1983A) and Floyd-Smith, G., *J. Cellular Biochem.*, 38: 12–21 (1988), and 2-5A synthetases, Hovanessian, A. G. et al., *Nature*, 268: 537–539 (1977), reviewed in Sen, G. C. and Lengyel, P., *J. Biol. Chem.*, 267: 5017–5020 (1992). Furthermore, several investigations have implicated the 2-5A system in the mechanism by which interferon inhibits the replication of picornaviruses. Indeed, 2-5A per se and highly specific 2-5A mediated rRNA cleavage products were induced in interferon-treated, encephalomyocarditis virus (EMCV)-infected cells. See Williams, B. R. G., *Nature*, 282: 582–586 (1979); Wreschner, D. H. et al., *Nucleic Acids Res.*, 9: 1571–1581 (1981b); and Silverman, R. H. et al., *Eur. J. Biochem.*, 124: 131–138 (1982a). In addition, expression of 2-5A synthetase cDNA inhibited the replication of picornaviruses, Chebath, J., *Nature*, 330: 587–588 (1987) and Rysiecki, E. F. et al., *J. Interferon Res.*, 9: 649–657 (1989), and the introduction of a 2-5A analogue inhibitor of 2-5A-dependent RNase into cells reduced the interferon-mediated inhibition of EMCV replication. See Watling, D. et al., *EMBO J.*, 4: 431–436 (1985). Further, 2-5A-dependent RNase levels were correlated with the anti-EMCV activity of interferon, Kumar, R. et al., *J. Virol.*, 62: 3175–3181 (1988), and EMCV-derived dsRNA both bound to and activated 2-5A synthetase in interferon-treated, infected cells. See Gribaudo, G. et al., *J. Virol.*, 65: 1948–1757 (1991).

The 2-5A system, however, almost certainly provides functions beyond the antipicornavirus activity of interferons. For instance, introduction of 2-5A into cells, Hovanessian, A. G. and Wood, J. N., *Virology*, 101: 81–90 (1980), or expression of 2-5A synthetase cDNA, Rysiecki, G. et al., *J. Interferon Res.*, 9: 649–657 (1989), inhibits cell growth rates. Moreover, 2-5A-dependent RNase levels are elevated in growth arrested cells, Jacobsen, H. et al., *Proc. Natl. Acad. Sci. U.S.A.*, 80: 4954–4958 (1983b), and 2-5A synthetase, Stark, G. et al., *Nature*, 278: 471–473 (1979), and 2-5A-dependent RNase levels are induced during cell differentiation. See, e.g., Krause, D. et al., *Eur. J. Biochem.*, 146: 611–618 (1985). Therefore, interesting correlations exist between 2-5A-dependent RNase and the fundamental control of cell growth and differentiation suggesting that the 2-5A system may function in general RNA metabolism. The ubiquitous presence of the 2-5A system in reptiles, avians and mammalians certainly supports a wider role for the pathway. See, for example, Cayley, P. J. et al., *Biochem. Biophy. Res. Commun.*, 108: 1243–1250 (1982).

Notwithstanding the importance of 2-5A-dependent RNase to the 2-5A system, 2-5A-dependent RNase enzymes having ribonuclease function have not been isolated, purified or sequenced heretofore. Consequently, there is a demand for isolated, active 2-5A-dependent RNases and their complete amino acid sequences, as well as a demand for encoding sequences for active 2-5A-dependent RNases.

SUMMARY OF THE INVENTION

In brief, the present invention alleviates and overcomes certain of the above-mentioned problems and shortcomings of the present state of the art through the discovery of novel, isolated 2-5A-dependent RNases and encoding sequences therefor.

Broadly speaking, the novel 2-5A dependent RNases of the instant invention are involved in the fundamental control of single stranded RNA decay in animal cells, such as mammals, and are also present in animal cells, such as avian and reptilian cells. More particularly, the novel 2-5A dependent RNases of the present invention have the ability to degrade single stranded RNA, mainly 3' of UpUp or UpAp sequences, after they are activated by binding to 5'-phosphorylated,2',5'-linked oligoadenylates (hereinafter "2-5A"). As a result, it is believed that the novel 2-5A dependent RNases are useful in connection with inhibition of cell growth rates, viral replication and in connection with interferon treatment of viral infection and cancer. As used herein, the term "2-5A-dependent RNase(s)" is used in a broad sense and is meant to include any amino acid sequence which includes a 2-5A binding domain and/or ribonuclease function when the 2-5A-dependent RNase is activated by 2-5A.

The novel 2-5A dependent RNases of the present invention are protein enzymes having molecular weights on the order of between about 74 KDa (murine) and about 84 KDa (human), as determined by gel electrophoresis migration and/or prediction from their respective encoding nucleotide sequences. For example, a human 2-5A-dependent RNase of the instant invention has a molecular weight of about 83,539 Da as determined from the amino acid sequence predicted from the encoding sequence therefor, whereas the murine 2-5A-dependent RNase has a molecular weight of about 74 KDa as determined by gel electrophoresis migration and from prediction of the amino acid sequence from the encoding sequence. While an about 74 KDa molecular weight is reported herein for a murine 2-5A-dependent RNase, it should nevertheless be appreciated that the reported molecular weight is for an incomplete murine 2-5A-dependent RNase. It is nevertheless believed that once completely sequenced, i.e., when an about 84 amino acid end region is identified, the molecular weight of a complete murine 2-5A-dependent RNase will be similar to that of human, i.e., about 84 KDa.

It should also be readily apparent to those versed in this art, however, that since gel electro-phoresis migration has been employed to determine molecular weight of a murine 2-5A-dependent RNase, the 74 KDa molecular weight is only an estimate based upon relative migration.

The amino acid sequence for human 2-5A-dependent RNase protein is depicted in FIG. 3 and Table 1. The encoding sequence for the human 2-5A-dependent RNase protein is also set forth in Table 1. The mRNA for human 2-5A-dependent RNase is about 5.0 Kb in size. The virtually complete amino acid sequence for the murine 2-5A-dependent RNase protein and the encoding sequence therefore is depicted in Table 2. The mRNA for murine 2-5A-dependent RNase is about 5.7 Kb in size.

Analysis of the amino acid sequences of the 2-5A-dependent RNases of the present invention have revealed several characteristics unique to the 2-5A-dependent RNases. For example, it has been discovered that the novel 2-5A dependent RNases of the instant invention include the following unique domains which span between the amino terminus and the carboxy terminus. For instance, it has been discovered that there are at least four ankyrin repeats, of which three lie closest to the amino terminus. However, while four ankyrin repeats have been discovered, it is believed that there may be additional ankyrin repeats that may total, for instance, about eight or more when the amino acid sequences of the 2-5A-dependent RNases of the present invention are further analyzed. It is believed that these ankyrin repeats may possibly function in protein-protein interaction. Ankyrin repeat 1 generally lies between amino acids designated as 58–90 in Tables I and II. Ankyrin repeat 2 generally lies between amino acids designated as 91–123 in Tables I and II. Ankyrin repeat 3 generally lies between amino acids designated as 124–156 in Tables I and II. Ankyrin repeat 4 generally lies between amino acids designated as 238 and 270 in Tables I and II. See also FIGS. 10A and 10B.

It has also been discovered that the novel 2-5A dependent RNases include a cysteine rich region (which has homology to zinc fingers) that lies closer to the carboxy terminus than the amino terminus which may possibly function in RNA recognition or in formation of protein dimers. The cysteine rich region is believed to include about 5 or 6 cysteine residues which generally lie between amino acids designated as 395–444 in the human sequence as reported in Table I and FIG. 4, or between amino acids designated as 401–436 in the murine sequence as reported in Table II and FIG. 4.

Still further, it has been discovered that the novel 2-5A dependent RNases include a duplicated phosphate binding (2 P-loops) motif which lies generally between the three ankyrin repeats motif and the cysteine-rich region. Even though the phosphate binding P-loop motifs generally follow the three ankyrin repeats, the fourth ankyrin repeat is contained within the repeated P-loop motifs. It is believed that the two P-loops are in the same orientation and constitute the binding domain necessary for binding 2-5A. It is further believed that each P-loop motif includes a lysine residue which is essential for maximum 2-5A binding activity. The lysine residues are designated as 240 and 274 in Tables I and II.

It has been further discovered that the 2-5A-dependent RNase proteins contain an amino acid region which follows the cysteine rich region that is believed to be homologous to protein kinases. Within this region, there is believed to be separate domains designated as domains VI and VII which generally lie between amino acid residues designated as 470–504 in Tables I and II. More particularly, as to the human sequence of 2-5A-dependent RNase, domain VI generally lies between amino acid residues designated as 471–491 and domain VII generally lies between amino acid residures designated as 501–504, as reported in Table I and FIG. 4. As to the murine sequence of the 2-5A-dependent RNase, domain VI generally lies between amino acids designated as 470–489 and domain VII generally lies between amino acid residues designated as 499–502, as reported in Table II and FIG. 4.

It has also been discovered that there is limited homology between the amino acid sequences for the 2-5A-dependent RNases of the present invention and RNase E, encoded by the altered mRNA stability (ams)/rne gene of E. Coli. Uniquely, the limited homology is generally conserved between the murine and human amino acid sequences for 2-5A-dependent RNases and generally lies between a 200 amino acid region. More particularly, for the human sequence, the amino acid region spans amino acid residues designated as 160–349 in Table I and FIGS. 9A and 9B. With respect to the murine sequence, the amino acid region spans amino acid residues designated as 160–348 in Table II and FIGS. 9A and 9B.

It has been further discovered and is believed that almost the entire, if not complete, amino acid sequences of the novel 2-5A-dependent RNase proteins of the instant invention are necessary for ribonuclease function. For example, it is believed that, when an about 84 amino acid region at the carboxy terminus is present in the human 2-5A-dependent RNase, the human 2-5A-dependent RNase has ribonuclease function in the presence of 2-5A. In contrast, when the murine 2-5A-dependent RNase lacks the about 84 amino acid region at the carboxy terminus, it lacks ribonuclease function.

With respect to the binding activity of a murine 2-5A-dependent RNase protein to 2-5A, it has been discovered that, when one P-loop is deleted from the repeated P-loop motif of a murine 2-5A-dependent RNase protein, nearly all 2-5A binding activity is lost, and that when both P-loops are deleted, virtually complete activity is lost. However, it has been found that, even though the carboxy terminus portion of the amino acid sequence of a murine 2-5A-dependent RNase protein following the repeated P-loop motif has been deleted, partial 2-5A binding activity is maintained.

It has been further discovered that when lysine residues 240 and 274 are replaced with asparagine residues in both P-loop motifs, significant 2-5A binding activity of a murine 2-5A-dependent RNase protein is lost. It has been further discovered, however, that when either lysine residue 240 or 274 is replaced in either P-loop motif, only partial 2-5A binding activity is lost. It is therefore believed that the presence of both P-loop motifs in the amino acid sequences for the 2-5A dependent RNases of the present invention plays an important role in 2-5A binding activity. It is further believed that the presence of lysine residues 240 and 274 in each P-loop motif plays an important role for enhanced 2-5A binding activity. It is also believed that the presence of virtually the entire amino acid sequence of the 2-5A-dependent RNases of the present invention provides for even further enhanced 2-5A binding activity, as well as provides for ribonuclease function.

In addition, the present invention relates to the cloning of murine and human 2-5A-dependent RNases and novel murine and human clones. Recombinant and naturally occurring forms of 2-5A-dependent RNase displayed virtually identical 2-5A binding properties and ribonuclease specificities.

The present invention further contemplates the use of the novel isolated, 2-5A-dependent RNases and encoding sequences therefor, as well as analogs and active fragments thereof, for use, for instance, 1.) in gene therapy for human and animal diseases including viral disease and cancer, 2.) as genetic markers for human disease due to perhaps cancer or viral infection, 3.) to develop plants and animals resistant to certain viruses, and 4.) as enzymes in connection with research and development, such as for studying the structure of RNA. In one manner to accomplish the above, and as contemplated by the present invention, the encoding sequences of the instant invention may be utilized in ex vivo therapy, i.e., to develop recombinant cells using the encoding sequence of the present invention using techniques known to those versed in this art. In another manner which may be employed to accomplish the above, the encoding sequences of the present invention may be combined with an appropriate promoter to form a recombinant molecule and inserted into a suitable vector for introduction into an animal, plant, or other lower life forms also using techniques known to those skilled in this art. Of course, other suitable methods or means known to those versed in this art may be selected to accomplish the above-stated objectives or other objectives for which the novel 2-5A-dependent RNases and encoding sequences of the present invention are suited.

While the present invention is described herein with reference to the particular sequences disclosed, it should nevertheless be understood by those skilled in this art that the present invention contemplates variations to the amino acid and/or nucleotide sequences which do not destroy 2-5A binding activity and/or ribonuclease activity. Therefore, the present invention contemplates any analogs or fragments of the 2-5A-dependent RNases or the encoding sequences therefor which are active. In other words, the present invention includes any amino acid or nucleotide sequence which has the ability to accomplish the objectives of the instant invention, i.e., any amino acid sequence which has 2-5A binding activity and/or ribonuclease activity and any nucleotide sequence which encodes for an amino acid sequence having 2-5A binding activity and/or ribonuclease activity.

The above features and advantages of the present invention will be better understood with reference to the accompanying FIGS., Detailed Description and Example. It should also be understood that the particular methods, proteins, encoding sequences and compositions illustrating the invention are exemplary only and not to be regarded as limitations of the invention.

BRIEF DESCRIPTION OF THE FIGS.

Reference is now made to the accompanying FIGS. in which is shown illustrative embodiments of the present invention from which its novel features and advantages will be apparent.

Figure 2A:
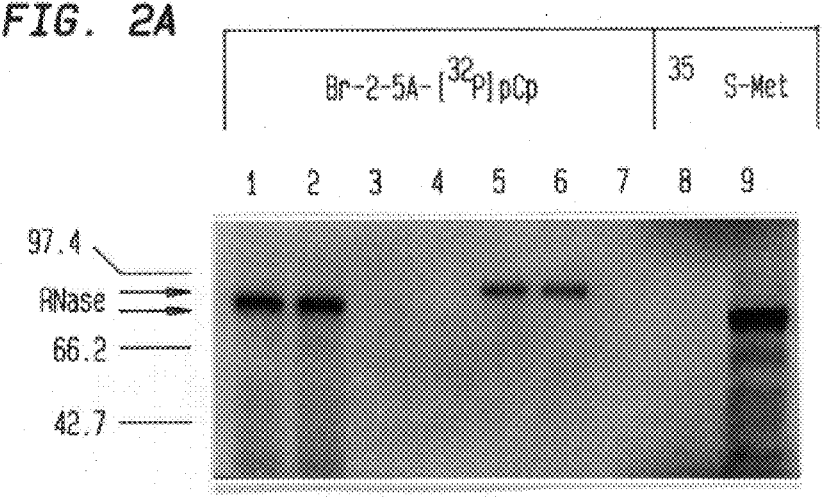
FIGS. 2A and 2B is a comparison of 2-5A binding activity of recombinant and naturally occurring forms of murine 2-5A-dependent RNase.

FIG. 2A is a specific affinity of truncated murine 2-5A-dependent RNase for 2-5A. UV covalent crosslinking of the $^{32}$P-2-5A probe (lanes 1–7) to protein is performed after translation reactions in wheat germ extract (5 $\mu$l) with murine 2-5A-dependent RNase mRNA (from clone ZB1) (lanes 1–3) or without added RNA (lane 4) or in extract of interferon treated mouse L cells (100 $\mu$g of protein) (lanes 5–7). Reactions are without added competitor (lanes 1, 4, and 5) or in the presence of either trimer core, (A2'p)$_2$A, (100 nM) (lanes 2 and 6) or trimer 2-5A, p$_3$(A2'p)$_2$A (100 nM) (lanes 3 and 7). Lanes 8 and 9 are produced by incubating the wheat germ extract with $^{35}$S-methionine in the absence or presence of 2-5A-dependent RNase mRNA, respectively.

Figure 2B:

FIG. 2B are identical chymotrypsin cleavage products and are obtained from recombinant and naturally occurring form of 2-5A-dependent RNase. Partial chymotrypsin digests (arrows) are performed on truncated 2-5A-dependent RNase (clone ZB1) produced in wheat germ extract ("Recombinant") and murine L cell 2-5A-dependent RNase ("Naturally Occurring") after crosslinking to the 2-5A probe and purification from gels.

Figure 3A:
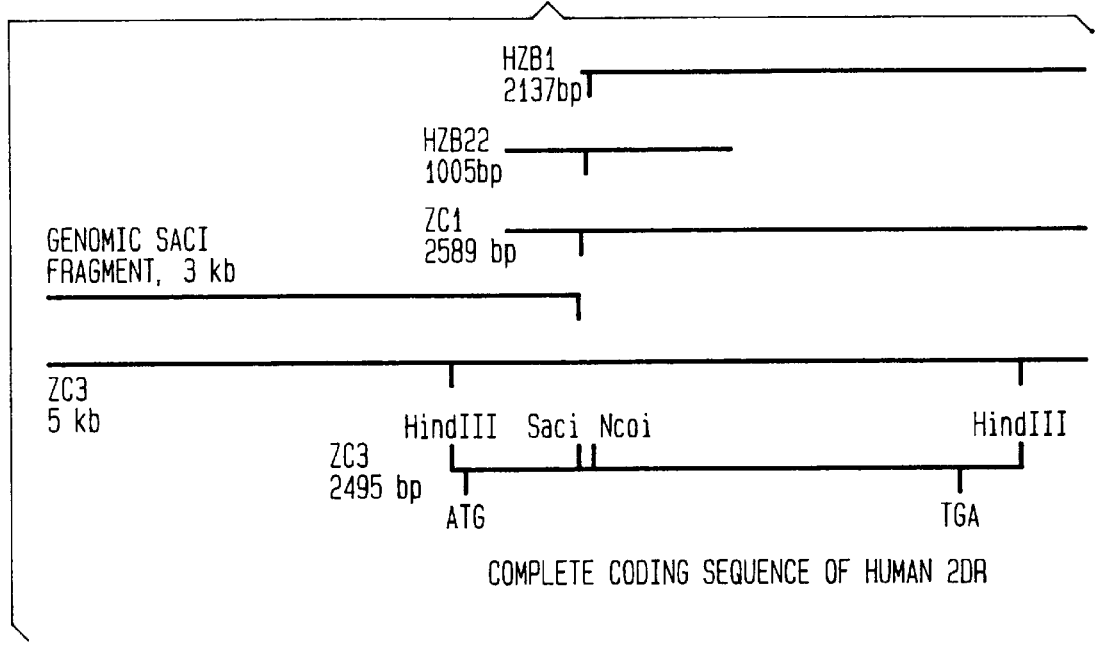
Figure 3B:
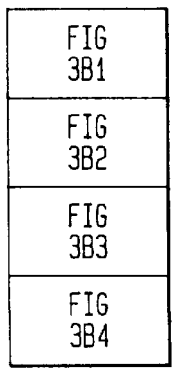

FIGS. 3A and 3B are clonings of the complete coding sequence for human 2-5A-dependent RNase.

FIG. 3A is the construction of a human 2-5A-dependent RNase clone. The initial human 2-5A-dependent RNase cDNA clone, HZB1, is isolated from an adult human kidney cDNA library in λgt10 using radiolabeled murine 2-5A-dependent RNase cDNA (clone ZB1) as probe. See Example. Radiolabeled HZB1 DNA is used to isolate a partially overlapping cDNA clone, HZB22, which is fused to HZB1 DNA at the NcoI site to form clone ZC1. The 5'-region of the coding sequence is obtained from a genomic SacI fragment isolated using a radiolabeled HZB22 DNA fragment as probe. Fusion of the genomic SACI fragment with ZC1 at the indicated SacI site produces clone ZC3. The coding sequence with some flanking sequences is then subcloned as a HindIII fragment into pBluescript KS(+) (Stratagene) resulting in clone ZC5. The restriction map for the composite clone, ZC5 , is shown. Clone HZB1 includes nucleotides designated as 658–2223 in Table I which encode for amino acids designated as 220–741 in Table I. Clone HZB22 includes a nucleotide sequence which encodes for amino acids designated as 62–397 in Table I. Clone ZC1 includes a nucleotide sequence which encodes for amino acids designated as 62–741 in Table I. Clones ZC3 and ZC5 both include nucleotide sequences which encode for amino acids designated as 1–741 in Table I.

FIGS. 3B1, 3B2, 3B3 and 3B4 are the nucleotide sequence and predicted amino acid sequence of human 2-5A-dependent RNase with flanking nucleotide sequences. The numbers to the right on each of FIGS. 3B1–3B4 indicate the positions of nucleotides and amino acid residues.

Figure 1:
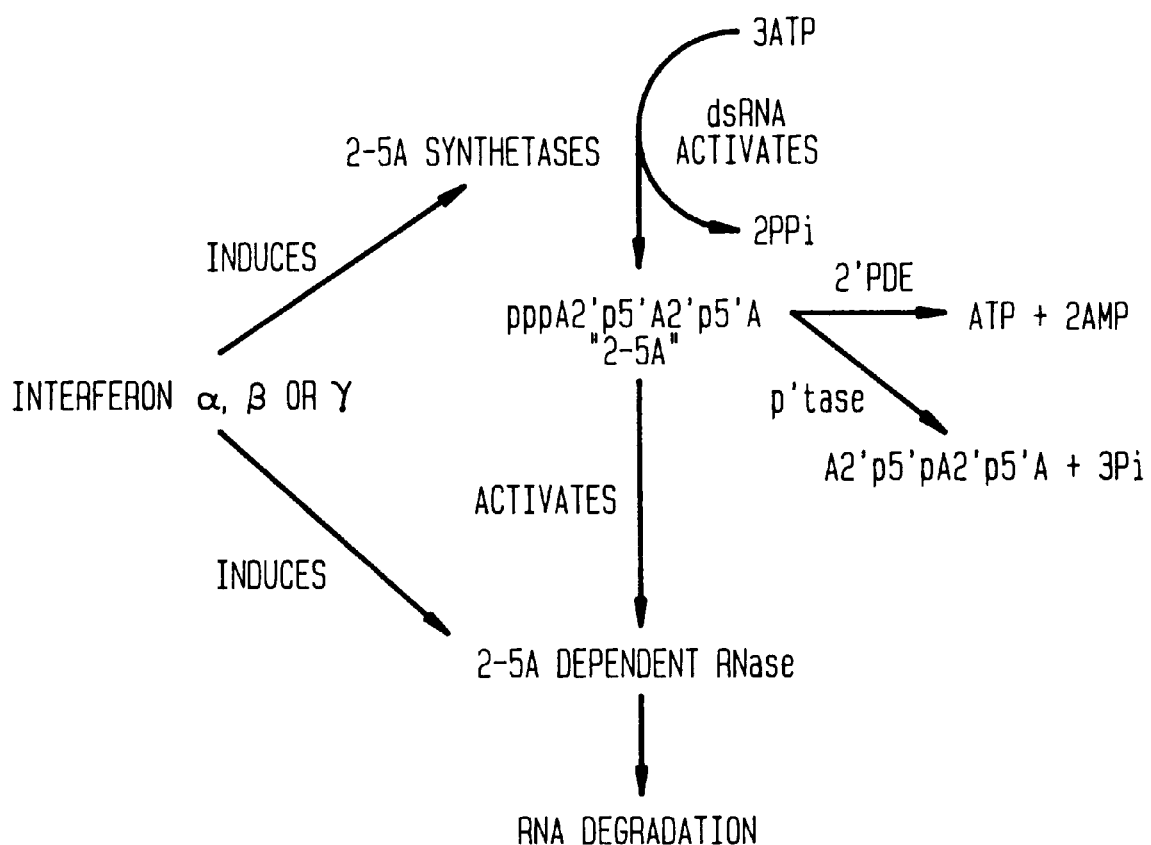
FIG. 1 is the 2-5A system: a ribonuclease pathway which is believed to function in the molecular mechanism of interferon action. 5'-phosphatase, p'tase; 2'-5'-phosphodiesterase, 2'-PDE.
Figure 4:
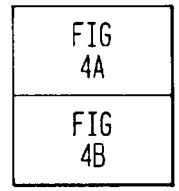

FIG. 3B shows the sequential order of FIGS. 3B1–3B4 for human 2-5A-dependent RNASE.

FIG. 4A and 4B are the alignment of the predicted amino acid sequences for murine and human forms of 2-5A-dependent RNase. The positions of the repeated P-loop motifs, the cysteine (Cys)-rich regions with homology to zinc fingers, and the regions of homology to protein kinase domains VI and VII are indicated. Amino acids residues which are important components of the indicated domains are represented in bold type and are italicized. Identical amino acid residues in murine and human 2-5A-dependent RNase are indicated with colon (:) symbols adjacent therebetween.

FIG. 4 shows the sequential order of FIGS. 4A and 4B for murime and human 2-5A-dependent RNASE.

Figure 5A:
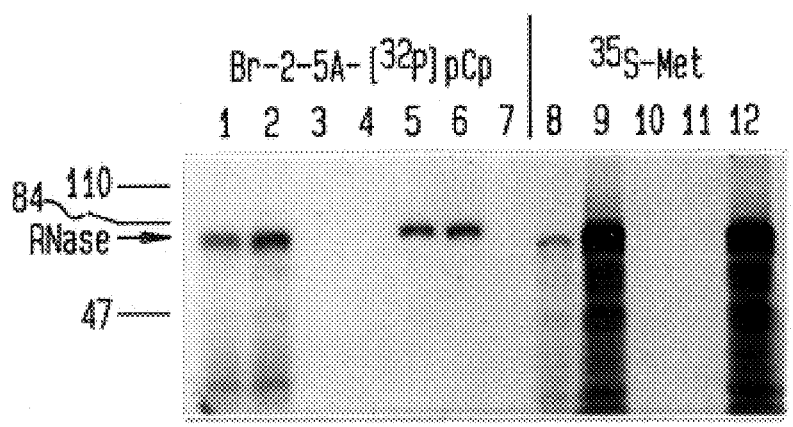
Figure 5B:
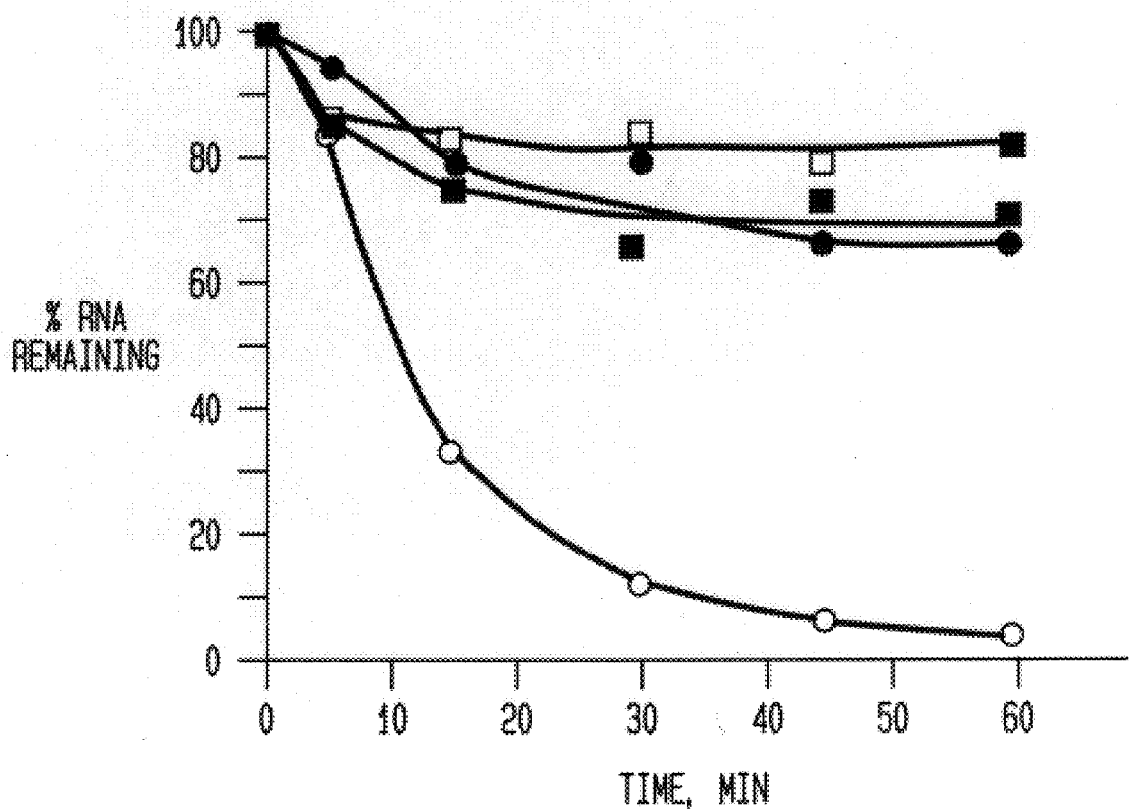

FIGS. 5A and 5B are 2-5A binding properties and ribonuclease activity of recombinant human 2-5A-dependent RNase produced in vitro.

FIG. 5A is specific affinity of recombinant human 2-5A-dependent RNase for 2-5A. Crosslinking of the 2-5A probe (lanes 1–7) to protein is performed after translation reactions in wheat germ extract (5 $\mu$l) with human 2-5A-dependent RNase mRNA (lanes 1–3) or without added RNA (lane 4) or in extract of human interferon a treated (1000 units per ml for 16 h) human HeLa cells (350 $\mu$g of protein) (lanes 5–7). Reactions were without added competitor (lanes 1, 4, and 5) or in the presence of either trimer core, $(A2'p)_2A$, (100 nM) (lanes 2 and 6) or trimer 2-5A, $p_3(A2'p)_2A$ (100 nM) (lanes 3 and 7). Incubations with $^{35}S$-methionine are shown in lanes 8 to 12. Lane 8 is with wheat germ extract and human 2-5A-dependent RNase mRNA. Reticulocyte lysate preadsorbed to 2-5A-cellulose is incubated with human 2-5A-dependent RNase MRNA in the absence (lane 9) or presence (lane 10) of cycloheximide, or in the absence of added mRNA (lane 11). Lane 12 shows human 2-5A-dependent RNase which is produced in the nonadsorbed, crude reticulocyte lysate. The positions and relative molecular masses (in kDa) of the marker proteins are indicated.

FIG. 5B is reticulocyte lysate pretreated to remove endogeous 2-5A-dependent RNase and is incubated in the absence of added mRNA (■), in the presence of human 2-5A-dependent RNase mRNA without inhibitor (○, □) or in the presence of both 2-5A-dependent RNase mRNA and cycloheximide (50 $\mu$g per ml (●). See Example. Subsequently, the recombinant 2-5A-dependent RNase (or controls) is adsorbed to 2-5A-cellulose and ribonuclease assays are performed after extensive washing of the matrix to reduce general nuclease activity. Radiolabeled substrate RNA was either poly(U) (○, ●, ■) or poly(C) (□).

Figure 6A:
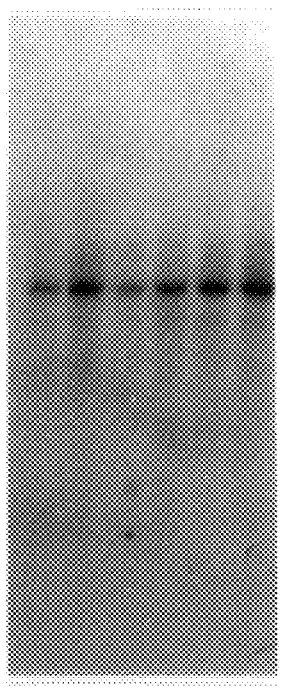
Figure 6B:
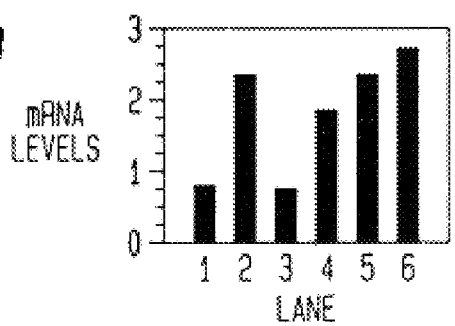
Figure 6C:

FIGS. 6A, 6B and 6C show levels of 2-5A-dependent RNase mRNA which are induced by interferon treatment of murine L929 cells even in the presence of cycloheximide.

FIG. 6A is a northern blot prepared with poly(A)⁺RNA (4 $\mu$g per lane) that is isolated from murine L929 cells treated with murine interferon (α+β) (1000 units per ml) and/or cycloheximide (50 $\mu$g per ml) for different durations (indicated) which is probed with radiolabeled murine 2-5A-dependent RNase cDNA. Interferon, IFN; cycloheximide, CHI.

FIG. 6B shows levels of 2-5A-dependent RNase which are estimated from the autoradiogram shown in panel (a) with a video camera and QuickCapture and Image computer programs.

FIG. 6C shows levels of glyceraldehyde-3-phosphate dehydrogenase (GAPDH) mRNA as determined in the same blot shown in panel (A).

Figure 7A:
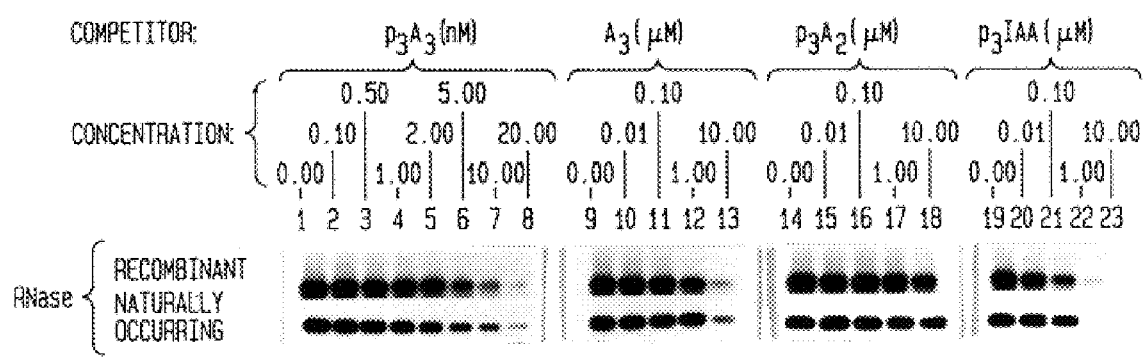
Figure 7B:
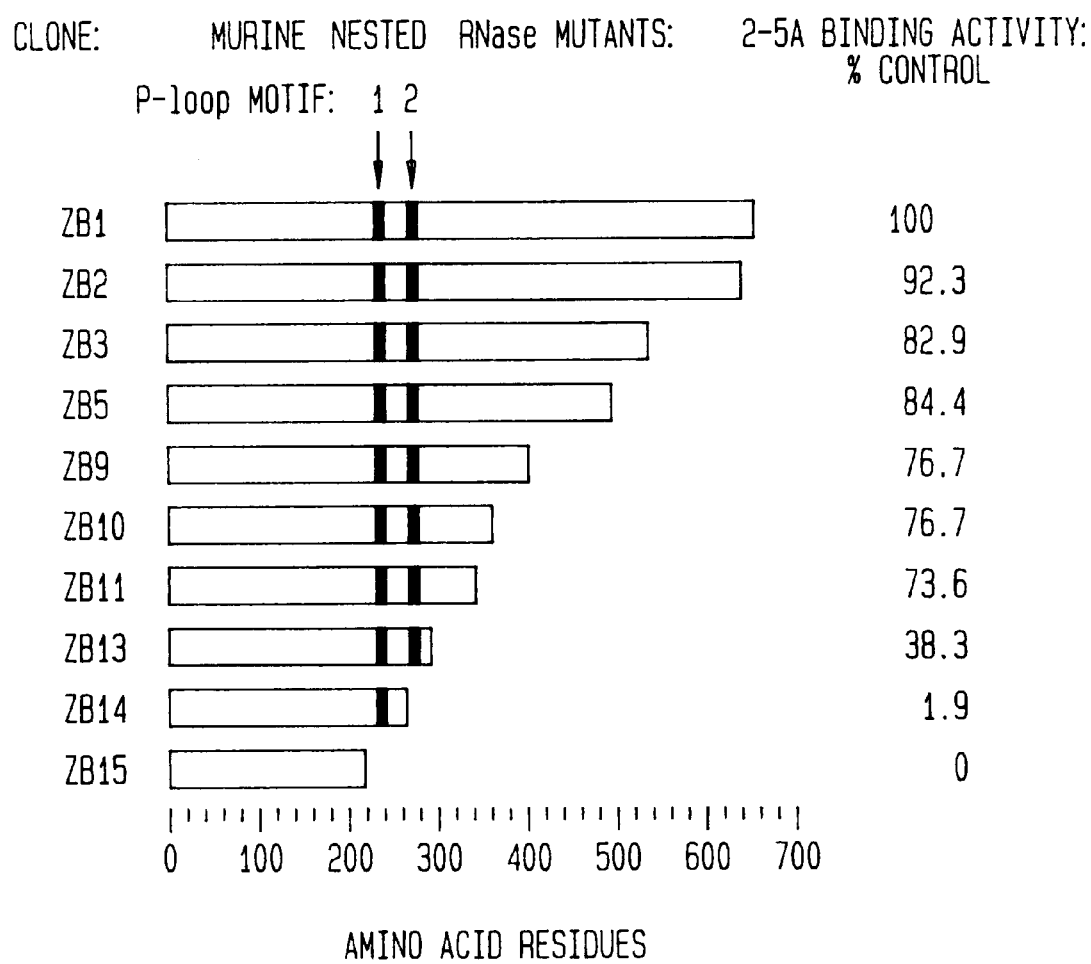

FIGS. 7A and 7B are the truncated, recombinant murine 2-5A-dependent RNase, clone ZB1, and murine L cell 2-5A-dependent RNase having identical 2-5A binding activities localized to a repeated P-loop motif.

FIG. 7A shows incubations of truncated 2-5A-dependent RNase, clone ZB1, ("Recombinant") which is produced in wheat germ extract (upper panel) or of murine L cell 2-5A-dependent RNase (labeled "Naturally Occurring," lower panel) with the $^{32}P$-2-5A probe, (2.4 nM), are in the absence of presence of unlabeled 2',5'-phosphodiester linked oligonucleotides (as indicated) followed by uv covalent crosslinking. Autoradiograms of the dried SDS/10% polyacrylamide gels are shown. Concentrations of the oligonucleotide competitors are indicated. I is inosine.

FIG. 7B shows a truncated series of murine 2-5A-dependent RNase mutants (ZB1 to ZB15) which is produced in wheat germ extract which are assayed for 2-5A binding activity by a filter binding method. See Example and Knight et al. 1980). The positions of the P-loop motifs and the lengths of the translation products are indicated. Clone ZB1 encodes for amino acids designated as 1–656 in Table II, except for the last 5 amino acid residues which are Lys, Pro, Leu, Ser, and Gly. Clone ZB2 encodes for amino acids designated as 1–619 in Table II. Clone ZB3 encodes for amino acids designated as 1–515 in Table II. Clone ZB5 encodes for amino acids designated as 1–474 in Table II. Clone ZB9 encodes for amino acids designated as 1–403 in Table II. Clone ZB10 encodes for amino acids designated as 1–365 in Table II. Clone ZB13 encodes for amino acids designated as 1–294 in Table II. Clone ZB14 encodes for amino acids designated as 1–265 in Table II. Clone ZB15 encodes for amino acids designated as 1–218 in Table II.

Figure 8A:
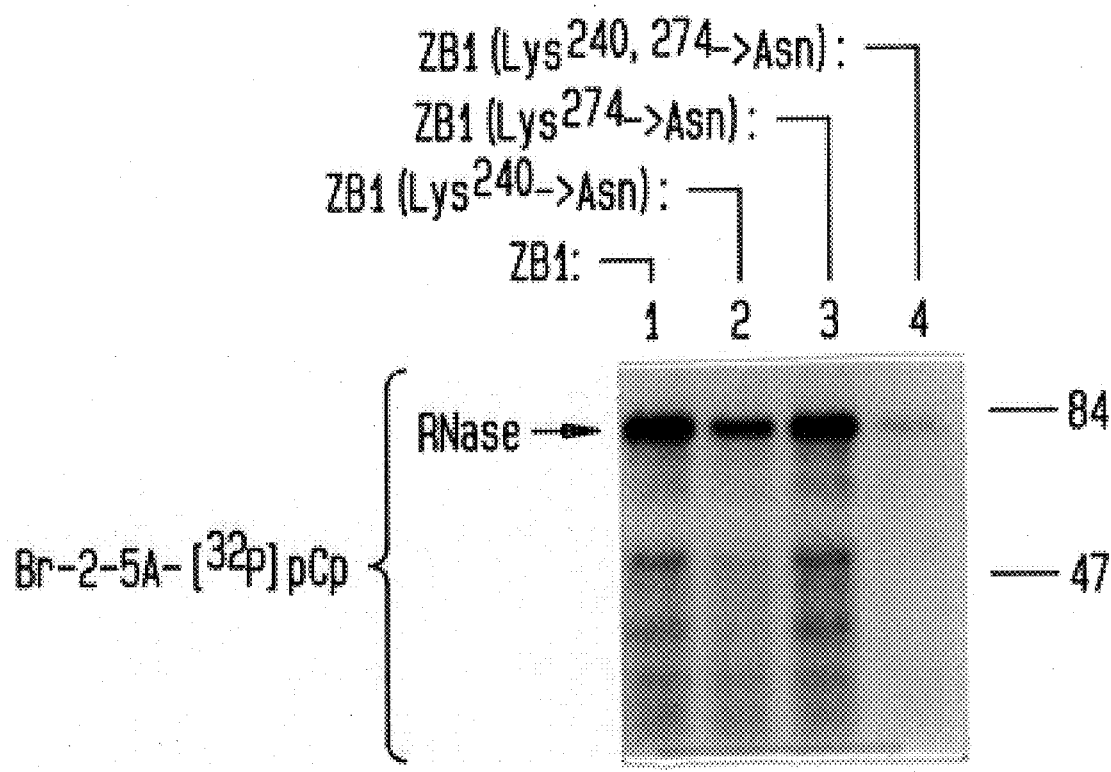
Figure 8B:
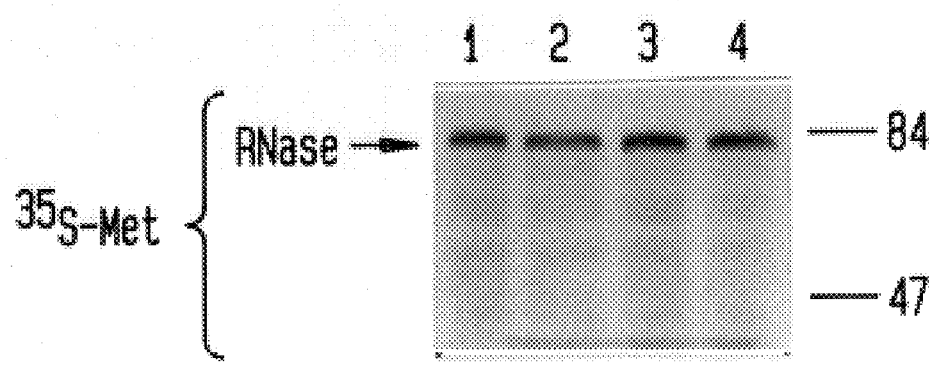

FIGS. 8A and 8B are substitution mutations of the lysine residues in the P-loop motifs of 2-5A-dependent RNase.

FIG. 8A shows the truncated murine 2-5A-dependent RNase, clone ZB1, and lysine to asparagine substitution mutants of clone ZB1, which are synthesized in wheat germ extract. In (A) unlabeled translation products are covalently crosslinked to the bromine-substituted, $^{32}P$-labeled 2-5A probe, Br-2-5A-[$^{32}P$]pCp. See Nolan-Sorden et al., 1990.

FIG. 8B shows the mRNA species which are translated in the presence of $^{35}$-S-methionine in separate reactions. Autoradiograms of the dried, SDS/polyacrylamide gels are shown. The order and positions of the translation products (labelled "RNase") and the relative molecular masses (in kDa) of the protein markers are indicated.

Figures 9A, 9B:
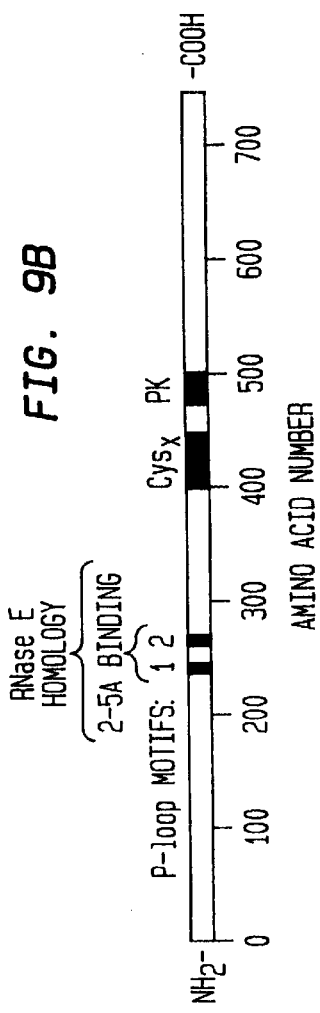

FIGS. 9A and 9B are a comparison of the amino acid sequences of RNase E and 2-5A-dependent RNase.

FIG. 9A shows identical and conservative matches which are shown between E. coli RNase E and the murine and human forms of 2DR.

FIG. 9B is a model for the structure and function of 2DR. Abbreviations: P-loop motifs, a repeated sequence with homology to P-loops; Cysx, a cysteine-rich region with homology to certain zinc fingers; PK, homology to protein kinase domains VI and VII.

FIGS. 10A and 10B are a comparison of the amino acid sequences of the ankyrin repeats in the human and murine 2-5A-dependent RNase proteins.

FIG. 10A shows murine and human forms of 2-5A-dependent RNases containing four ankyrin repeats. Homology between the ankyrin consensus sequence and the murine and human forms of 2-5A-dependent RNase are indicated. ψ, hydrophobic amino acids.

FIG. 10B is a model showing the relative positions of the four ankyrin repeats in 2-5A-dependent RNase in comparison to the position of the proposed 2-5A binding domain (○) (the repeated P-loop motif); $Cys_x$, the cysteine-rich region; PK, the protein kinase homology region, and the carboxy-terminal region required for RNase activity.

Figure 11:
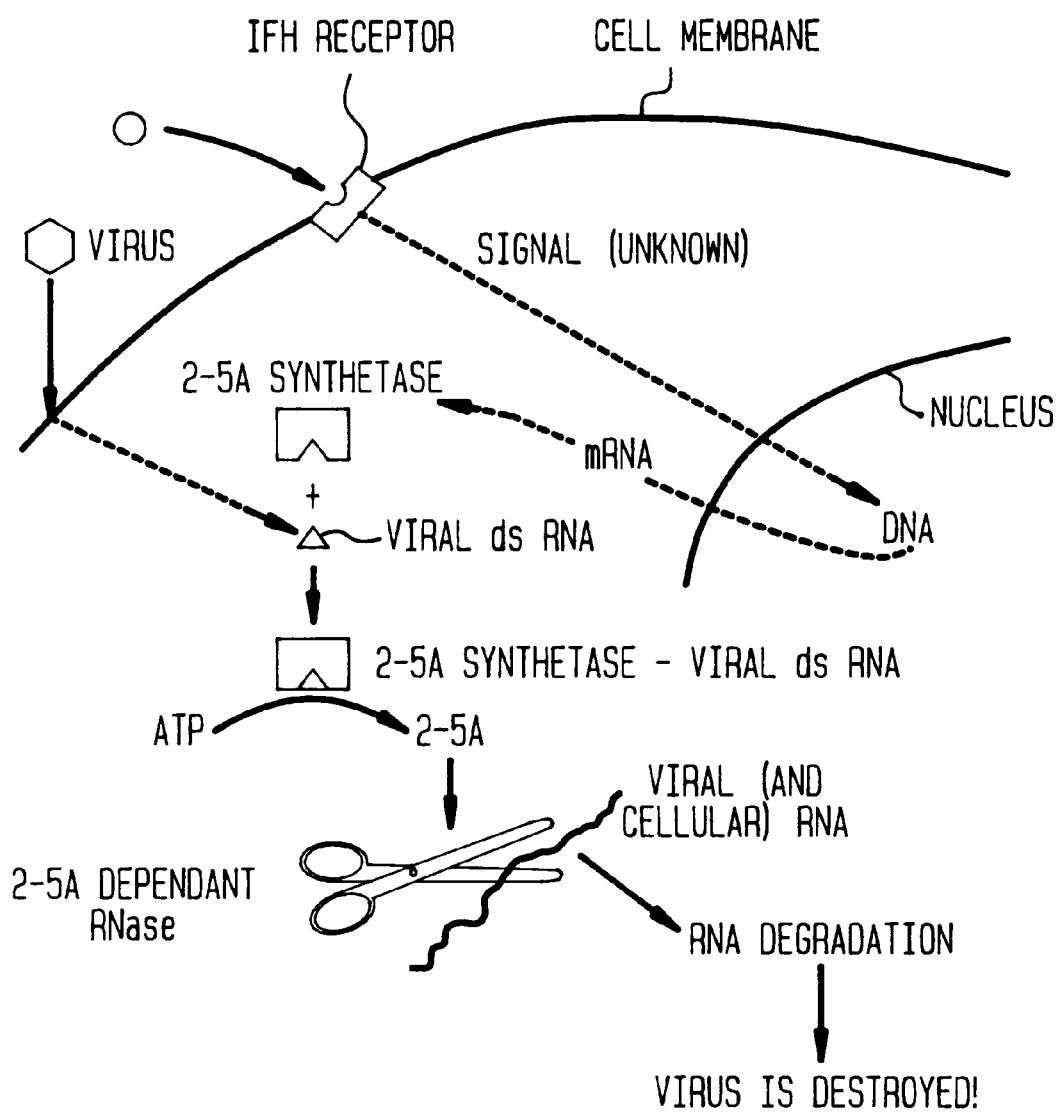

FIG. 11 shows the role of 2-5A-dependent RNase in the anti-viral response of cells to interferon treatment. Interferon binds to specific cell surface receptors resulting in the generation of a signal which activates a set of genes in the cell nucleus. The genes for 2-5A synthetase are thus activated producing inactive, native 2-5A synthetase. Interferon treatment of the cell also activates the 2-5A-dependent RNase gene (not shown in the figure). Subsequently, the interferon-treated cells is infected by a virus. The virus produces double stranded RNA (dsRNA) during its replicative cycle. The viral dsRNA then activates the 2-5A synthetase resulting in the production of 2-5A. The 2-5A then activates the 2-5A-dependent RNase to degrade the viral RNA thus destroying the virus itself.

DETAILED DESCRIPTION

By way of illustrating and providing a more complete appreciation of the present invention and many of the attendant advantages thereof, the following Detailed Description and Example is given concerning the novel 2-5A-dependent RNases, encoding sequences therefore, recombinant nucleotide molecules, vectors and cells.

Because 2-5A-dependent RNase is very low in abundance (one five-hundred-thousandth of the total protein in mouse liver, Silverman, R. H. et al.,*J. Biol. Chem.*, 263: 7336–7341 (1988)), its cloning requires the development of a sensitive screening method. Murine L929 cells are selected as the source of mRNA due to high basal levels of 2-5A-dependent RNase. A protocol to enhance 2-5A-dependent RNase mRNA levels is developed based on the observation that optimal induction of 2-5A-dependent RNase is obtained by treating cells with both interferon and cycloheximide, then with medium alone. See Example. The cDNA library is screened by an adaptation of techniques developed for cloning DNA binding proteins, Singh, H. et al., *Cell*, 52: 415–423 (1988); Singh H. et al., *BioTechniques,* 7: 252–261 (1989), in which a bromine-substituted $^{32}$P-labeled 2-5A analogue ("2-5A probe"), Example and Nolan-Sorden, N. L. et al., *Anal. Biochem.*, 184: 298–304 (1990), replaced a radiolabeled oligodeoxyribonucleotide. A single clone (ZB1) is thus isolated from about three million plaques. The protein expressed from the ZB1 clone, transferred from plaques to filter-lifts, shows reactivity to both the 2-5A probe and to a highly purified polyclonal antibody directed against 2-5A-dependent RNase.

To obtain recombinant protein for characterization, the cDNA is transcribed and translated in cell-free systems. See Example. 2-5A binding activity is then determined by covalently crosslinking the 2-5A probe to the protein with uv light, for example, Nolan-Sorden, N. L. et al., *Anal. Biochem.*, 184: 298–304 (1990). The recombinant 74 kDa protein produced in a wheat germ extract shows specific affinity for the 2-5A probe. See FIG. 2A, lanes 1 to 3. A core derivative of 2-5A lacking 5'-phosphoryl groups, $(A2'p)_2A$, fails to interfere with binding of the protein to the 2-5A probe whereas trimer 205A, $p_3(A2'p)_2A$, completely prevents probe binding. See FIG. 2A, lanes 2 and 3, respectively. There is no detectable 2-5A binding proteins in the wheat germ extract as shown in the incubation without added RNA, FIG. 2A, lane 4. For comparison, a similar profile of 2-5A binding activity is obtained for the 80 kDa 2-5A-dependent RNase from murine L929 cells, incubated without added oligonucleotide or with $(A2'p)_2A$ or $p_3(A2'p)_2A$ as competitors. See FIG. 2A, lanes 5 to 7. The $^{35}$S-labeled translation product is shown in FIG. 2A, lane 9. In a further comparison, covalent linkage of the 2-5A probe to the about 74 kDa protein and to murine L929 cell 2-5A-dependent RNase followed by partial digestion with chymotrypsin produces an identical pattern of six labeled peptides. See FIG. 2B. Similarly, partial digestion of the two labeled proteins with S. aureus V8 protease also produces identical patterns of labeled cleavage products. These results and the apparent molecular weight of about 74 kDa for the recombinant protein, as compared to about 80 kDa for 2-5A-dependent RNase, see FIG. 2A, suggests that the about 74 kDa protein is a truncated, or partial clone for 2-5A-dependent RNase.

To obtain the entire coding sequence for human 2-5A-dependent RNase, a composite DNA containing genomic and cDNA is constructed. See FIG. 3A. The initial cDNA portion of the human 2-5A-dependent RNase clone (HZB1) is obtained by screening a human kidney cDNA library with radiolabeled murine 2-5A-dependent RNase cDNA. See Example. A genomic clone, containing the 5'-part of the coding sequence, is isolated with radiolabeled human 2-5A-dependent RNase cDNA. The nucleotide and predicted amino acid sequences of human 2-5A-dependent RNase are determined, FIG. 3B, resulting an open reading frame encoding a protein of 83,539 Da.

A comparison is made between the predicted amino acid sequences of the human and murine forms of 2-5A-dependent RNase in order to identify and evaluate the conserved regions of the proteins. See FIG. 4. The murine cDNA, clone ZB1, contains about 88% of the coding sequence for 2-5A-dependent RNase to which an additional twenty-eight 3'-codons are added from a murine genomic clone. Alignment of the murine and human forms of 2-5A-dependent RNase indicates about 65% identity between the overlapping regions. See FIG. 4. In addition, there is 73% identity between the corresponding nucleotide sequences for murine and human 2-5A-dependent RNase. The apparent translation start codons for both the murine and human 2-5A-dependent RNases, are in an appropriate context for translational initiation, namely ACC<u>ATG</u>G and GTC<u>ATG</u>G, respectively. See FIG. 3B. See also, for example, Kozak, M., *Cell,* 44: 283–292 (1986). In addition, both the human and murine 2-5A-dependent RNase sequences contain in-frame stop codons upstream of the translation start sites. See FIG. 3B.

The 2-5A binding properties of the recombinant and naturally occurring forms of human 2-5A-dependent RNase are compared by uv covalent crosslinking to the 2-5A probe. The recombinant human 2-5A-dependent RNase produces in wheat germ extract shows specific affinity for 2-5A. See FIG. 5A, lanes 1 to 3. Radiolabeling of the cloned human 2-5A-dependent RNase with the 2-5A probe is not prevented by $(A2'p)_2A$. See FIG. 5A, lanes 1 and 2. In contrast, addition of trimer 2-5A, $p_3(A2'p)_2A$, effectively competes with the 2-5A probe for binding to the recombinant 2-5A- dependent RNase. See lane 3. The same pattern of 2-5A binding activity is obtained with 2-5A-dependent RNase in an extract of interferon-treated human HeLa cells. See FIG. 5A, lanes 5 to 7. The apparent molecular weights of HeLa cell 2-5A-dependent RNase and $^{35}$S-labeled recombinant human 2-5A-dependent RNase produced in reticulocyte lysate are believed to be exactly the same (about 80 kDa). See FIG. 5A, lanes 5 and 9. The recombinant human 2-5A-dependent RNase produced in wheat germ extract migrates slightly faster probably due to post-translational modifications. See FIG. 5A, lanes 1, 2 and 8.

To demonstrate and characterize the ribonuclease activity of the cloned 2-5A-dependent RNase, translation is performed in a reticulocyte lysate instead of a wheat germ extract due to the substantially greater efficiency of protein synthesis in the former system. See FIG. 5A, compare lanes 9 and 8. Prior to translation, endogenous reticulocyte 2-5A-dependent RNase is removed by adsorbing the lysate to the affinity matrix, 2-5A-cellulose. See Example. See also, Silverman, R. H., *Anal. Biochem.*, 144: 450–460 (1985). The treatment with 2-5A-cellulose effectively removes all measurable endogenous 2-5A-dependent RNase activity from the lysate, as determined by 2-5A-dependent ribonuclease assays, and FIG. 5B. In addition, the adsorption-depletion protocol did not reduce translational efficiency. FIG. 5A, lanes 9 and 12 show the $^{35}$S-translation products produced in the 2-5A-cellulose-pretreated and untreated lysates, respectively.

Ribonuclease assays with recombinant 2-5A-dependent RNase are performed after immobilizing and purifying the translation product on the activating affinity matrix, 2-5A-cellulose. It was previously shown that murine L cell 2-5A-dependent RNase bound to 2-5A-cellulose, resulting in ribonuclease activity against poly(U) but not poly(c). See Silverman, R. H., *Anal. Biochem.*, 144: 450–460 (1985). Furthermore, by washing 2-5A-dependent RNase: 2-5A-cellulose prior to adding the substrate the level of general, non-2-5A-dependent RNase, is greatly reduced. See Silverman, R. H., *Anal. Biochem.*, 144: 450–460 (1985). Incubations of lysate in the absence of added mRNA or in the presence of both human 2-5A-dependent RNase mRNA and cycloheximide resulted in only low levels of poly(U) breakdown. See FIG. 5B. In addition, it is shown that cycloheximide completely prevented 2-5A-dependent RNase synthesis. See FIG. 5A, lane 10. In contrast, translation of the human 2-5A-dependent RNase mRNA, in the absence of inhibitor, results in substantial ribonuclease activity against poly(U) but not against poly(C). See FIG. 5B. The poly(U) is degraded with a half-life of about 10 minutes whereas only 20% of the poly(C) is degraded after one hour of incubation. Binding of recombinant 2-5A-dependent RNase to the affinity matrix was also shown by monitoring the presence of the $^{35}$S-labeled translation product. These results are believed to demonstrate that the recombinant human 2-5A-dependent RNase produced in vitro is a functional and potent ribonuclease. Furthermore, both recombinant and naturally occurring forms of 2-5A-dependent RNase are capable of cleaving poly(U) but not poly(C). See FIG. 5B. See also Silverman, R. H., *Anal. Biochem.*, 144: 450–460 (1985) and Floyd-Smith, G. et al., *Science*, 212: 1020–1032 (1981).

To determine if 2-5A-dependent RNase mRNA levels are regulated by interferon, a northern blot from murine L929 cells treated with interferon and cycloheximide is probed with the radiolabeled murine 2-5A-dependent RNase cDNA. See FIG. 6. 2-5A-dependent RNase mRNA levels are enhanced three-fold by interferon (α+β) treatment even in the presence of cycloheximide. See FIGS. 6A and B, compare lanes 1 and 2). Regulation of 2-5A-dependent RNase mRNA levels by interferon as a function of time is demonstrated (FIGS. 6A and B, lanes 3 to 6. Maximum 2-5A-dependent RNase mRNA levels are observed after 14 hours of interferon treatment. See FIGS. 6A and B, lane 6. A similar increase in levels of 2-5A-dependent RNase per se is observed after interferon treatment of the cells. Relatively invariant levels of GAPDH mRNA indicates that equivalent levels of RNA are present in every lane of the blot. See FIG. 6C. These results are believed to show that the induction of 2-5A-dependent RNase expression is a primary response to interferon treatment. The murine and human 2-5A-dependent RNase mRNAs are determined from northern blots to be 5.7 kb and 5.0 kb in length, respectively. See FIG. 6A. The 2-5A-dependent RNase coding sequences, therefore, comprise only about 40% the nucleotide sequences contained in the mRNAs.

The 2-5A binding functions of the recombinant and naturally occurring forms of murine 2-5A-dependent RNase are characterized by covalent crosslinking to the 2-5A probe in the presence of unlabeled 2-5A or 2-5A analogues as competitors. See FIG. 7A. Interestingly, although the about 74 kDa truncated 2-5A-dependent RNase is missing about 84 amino acids from its carboxy-terminus, see FIG. 4, it nonetheless possesses a 2-5A binding activity indistinguishable from that of naturally occurring 2-5A-dependent RNase. See FIG. 7A. Trimer 2-5A[p$_3$(A2'p)$_2$A], at about 20 nM effectively prevents the 2-5A probe from binding to either protein. See FIG. 7A, lane 8. In comparison, a 500-fold higher concentration of (A2'p)$_2$A (10 μM) is required to prevent probe binding to both proteins. See lane 13. The dimer species, p$_3$A2'pA, is unable to prevent the 2-5A probe from binding to the proteins even at a concentration of 10 μM (lane 18). However, the inosine analogue, p$_3$I2'pA2'pA, Imai, J. et al., *J. Biol. Chem.*, 260: 1390–1393 (1985), is able to prevent probe binding to both proteins but only when added at a concentration of about 1.0 μM (lane 22).

To further define sequences involved in 2-5A binding, nested 3'-deletions of the murine 2-5A-dependent RNase cDNA, clone ZB1, are constructed, transcribed in vitro, and expressed in a wheat germ extract. See FIG. 7B. The different deletion clones produce comparable amounts of polypeptide as monitored by incorporation of $^{35}$S-methionine. The levels of 2-5A binding activity are determined with the 2-5A probe in both a filter binding assay, Knight, M. et al., *Nature*, 288: 189–192 (1980), and the uv crosslinking assay, Nolan-Sorden, N. L. et al., *Anal. Biochem.*, 184: 298–304 (1990), with similar results. See FIG. 7B. Expression of clone ZB11, encoding amino acid residues 1 to 342, results in a loss of only about 26% of the 2-5A binding activity as compared to clone ZB1 (amino acids 1 to 656). See FIG. 7B. Clones intermediate in length between ZB1 and ZB11 all result in significant levels of 2-5A binding activity. In contrast, protein produced from ZB13 (amino acids 1 to 294) results in only about 38.3% of the 2-5A binding activity of clone ZB1, suggesting that a region important for the 2-5A binding function is affected. Indeed, clone ZB14 produced a protein encoding amino acids 1 to 265 which is nearly inactive in the 2-5A binding assay (only 1.9% of th activity of clone ZB1). Interestingly, the significant decrease in 2-5A binding activity observed with ZB14 occurs with the deletion of one of two P-loop motifs; nucleotide binding domains in many proteins. See FIGS. 4 and 7B. See also Saraste, M. et al., *TIBS*, 14: 430–434 (1990). Deletion of both P-loop motifs in clone ZB15 results in protein (amino acids 1 to 218) which is completely lacking in 2-5A binding activity. See FIG. 7B.

To probe the involvement of the consensus lysine residues in the P-loop motifs in 2-5A binding activity, site-directed mutagenesis is performed on the truncated form of murine 2-5A-dependent RNase encoded by clone ZB1. Previously, it is reported that substitution mutations of the conserved lysine residues in P-loop motifs of eucaryotic initiation factor 4A and for Bacillus anthracis adenylyl cyclase results in a loss of ATP binding and catalytic activities, respectively. See Rozen et al., *Mol. Cell. Biol.,* 9: 4061–4063 (1989) and Xia, Z. and Storm, D. R., *J. Biol. Chem.,* 265: 6517–6520 (1990). In the former study the invariant lysine residue is mutated to asparagine. See Rozen et al., *Mol. Cell. Biol.,* 9: 4061–4063 (1989). We substituted, individually and together, the consensus lysines with asparagines at positions 240 and 274 in the two P-loop motifs of 2-5A-dependent RNase. See FIG. 8 and the Example. Analysis of the effects of these mutations on 2-5A binding activity is determined by covalently crosslinking the $^{32}$P-2-5A probe to the in vitro translation products under uv light. See FIG. 8A. See also Nolan-Sorden, N. L. et al., *Anal. Biochem.,* 184: 298–304 (1990). Similar levels of proteins are synthesized from the different mRNA species as shown in separate reactions containing $^{35}$S-methionine. See FIG. 8B. The three mutant forms of 2-5A-dependent RNase shows reduced binding to the 2-5A probe. See FIG. 8A, lanes 2 to 4. Clone ZB1 (Lys$^{240}$→Asn), FIG. 8A, lane 2, expresses a mutant 2-5A-dependent RNase with a substantially reduced affinity for 2-5A; about 48.4% of the activity of clone ZB1as determined by phosphorimager analysis (Molecular Dynamics) of the dried gel. A more modest reduction in 2-5A binding activity, to 79% of the control value, is obtained from clone ZB1 (Lys$^{274}$→Asn). See FIG. 8A, lane 3. In contrast, 2-5A binding activity from clone ZB1 (Lys$^{240,274}$→Asn), FIG. 8A, lane 4, in which both conserved lysine residues are replaced with asparagine residues, is reduced to only 12.2% of the activity of clone ZB1 (averaged from three separate experiments). These results suggest that the lysine residues at positions 240 and 274 function within the context of a repeated P-loop motif in the binding of 2-5A to 2-5A-dependent RNase.

The molecular cloning and expression of 2-5A-dependent RNase, the terminal factor in the 2-5A system and a key enzyme in the molecular mechanisms of interferon action is described. See FIG. 1. The recombinant proteins produced in vitro are demonstrated to possess 2-5A binding properties identical to naturally occurring forms of murine and human 2-5A-dependent RNase. See FIGS. 2, 5A, and 7. In addition, linkage of a $^{32}$P-2-5A analogue to a truncated murine 2-5A-dependent RNase and to murine L cell 2-5A-dependent RNase followed by partial proteolysis reveals identical patterns of labeled peptides. See FIG. 2B. Furthermore, the full-length recombinant human 2-5A-dependent RNase isolated on the activating, affinity matrix, 2-5A-cellulose, shows potent ribonuclease activity towards poly(U) but none against poly(C). See FIG. 5B. Similarly, it is previously demonstrated that murine L cell 2-5A-dependent RNase was activated by 2-5A-cellulose resulting in the cleavage of poly(U), but not of poly(C). See Silverman, R. H.,*Anal. Biochem.,* 144: 450–460 (1985). The full-length human 2-5A-dependent RNase, which is produced in reticulocyte lysate, had the same apparent molecular weight as did naturally occurring 2-5A-dependent RNase. See FIG. 5A. However, the actual molecular mass of human 2-5A-dependent RNase is determined from the predicted amino acid sequence, FIG. 3B, to be about 83,539 Da.

Previously, it was reported that interferon enhances levels of 2-5A-dependent RNase by between two- to twenty-fold depending on the cell type. See Silverman, R. H. et al., Eur. *J. Biochem.,* 126: 333–341 (1982b) and Jacobsen, H. et al., *Virology,* 125: 496–501 (1983a). Results presented herein suggest that the gene for 2-5A-dependent RNase may be an interferon-stimulated gene. See FIG. 6. Levels of 2-5A-dependent RNase mRNA in murine L929 cells are elevated as a function of time of interferon ($\alpha+\beta$) treatment by a factor of about three. Furthermore, the induction appeared to be a primary response to interferon treatment because it is observed in the presence of cycloheximide. Therefore, interferon is believed to regulate the 2-5A pathway by elevating levels of both 2-5A synthetases, Hovanessian, A. G. et al., *Nature,* 268: 537–539 (1977), and 2-5A-dependent RNase, Jacobsen, H. et al., *Virology,* 125: 496–501 (1983a). See FIGS. 1, 6 and 11.

The cloning of 2-5A-dependent RNase reveals several features of the protein. The 2-5A binding domain is of particular interest because it is the ability of 2-5A-dependent RNase to be activated by 2-5A that sets it apart from other nucleases. By expressing nested 3'-deletions of murine 2-5A-dependent RNase, a region between amino acids residues 218 and 294 which is believed to be critical for 2-5A binding activity is identified. See FIG. 7B. Interestingly, the identified region contains a repeated P-loop motif, one from residues 229 to 241 and another from residues 253 to 275. See FIG. 4 and Table II. When the latter P-loop motif (amino acids 253–275) is partially deleted, there is a precipitous decline in 2-5A binding activity. See clone ZB14 in FIG. 7B.

The homology with P-loops is believed to be highly conserved between the human and murine forms of 2-5A-dependent RNase; thus underscoring the belief of the importance of this region for 2-5A binding activity. See FIG. 4. The similarity to P-loops consists of the tripeptides, glycine-lysine-threonine, preceded by glycine-rich sequences. In this regard, the unusual feature of 2-5A-dependent RNase is that the P-loop motif is repeated and are in the same orientation. Adenylyl cyclase from Bacillus anthracis also contains a duplicated P-loop motif, however, the two sequences are in opposite orientation and are overlapping. See Xia, Z. and Storm, D. R., *J. Biol. Chem.,* 265: 6517–6520 (1990).

The relative importance of the conserved P-loop lysines (at positions 240 and 274) are evaluated by site-directed mutagenesis of the murine 2-5A-dependent RNase, clone ZB1. Although individual substitution mutations of the two lysines significantly reduced 2-5A binding activity, replacing both of the lysines with asparagine residues in the same mutant RNase severely represses 2-5A binding. See FIG. 8. Perhaps the trimer 2-5A requirement for activation of most forms of 2-5A-dependent RNase could be explained if the first and third adenylyl residues of 2-5A interact with the separate P-loop sequences inducing conformational changes in 2-5A-dependent RNase. In this regard, dimer 2-5A neither binds 2-5A-dependent RNase efficiently nor does it activate 2-5A-dependent RNase, FIG. 7A; Kerr, I. M. and Brown, R. E., *Prod. Natl. Acad. Sci. U.S.A.,* 75: 265–260 (1978) and Knight, M. et al., *Nature,* 288: 189–192 (1980), perhaps because it is too short to span the two P-loop motifs. Alternately, the residual 2-5A binding activity observed in the point mutants, ZB1(Lys$^{240}$→Asn) and ZB1 (Lys$^{274}$→Asn), and the very low affinity of the double mutant, ZB1(Lys$^{240, 274}$→Asn) for 2-5A, could indicate that the two P-loop motifs are parts of separate 2-5A binding domains.

Homology with protein kinase domains VI and VII is also identified in 2-5A-dependent RNase. See FIG. 4. See also Hanks, S. K. et al., *Science*, 241: 42–52 (1988). Although domain VI is believed to be involved in ATP binding, this region in 2-5A-dependent RNase is believed not to be important for 2-5A binding because its deletion caused only a minimal reduction in affinity for 2-5A. See FIG. 7B. However, a modest (two-fold) stimulatory effect of ATP on 2-5A-dependent RNase activity has been reported. See Wreschner, D. H. et al., *Eur. J. Biochem.*, 124: 261–268 (1982) and Krause, D. et al., *J. Biol. Chem.*, 261: 6836–6839 (1986). The latter report indicated that ATP was not required for 2-5A-dependent RNase activity but may act to stabilize the enzyme. Therefore, the region of homology with protein kinases could perhaps bind ATP resulting in stimulation of ribonuclease activity through stabilization of the enzyme.

A consensus zinc finger domain, reviewed in Evans, R. M. and Hollenberg, S. M., *Cell*, 52: 1–3 (1988), consisting of six cysteine residues with the structure $CX_4CX_3CX_{17}CX_3CX_3C$ (amino acid residues 401–436 in Table II) is identified in the murine form of 2-5A-dependent RNase. See FIG. 4. The homologous region in the human form of 2-5A-depenent RNase is $CX_{11}CX_{25}CX_3CX_6C$ (amino acid numbers 395 to 444 in Table I). Because zinc fingers are nucleic acid binding domains, the cysteine-rich region in 2-5A-dependent RNase could be involved in binding to the RNA substrate. Alternatively, the cysteine-rich domain in 2-5A-dependent RNase could mediate formation of 2-5A-dependent RNase dimers. Analysis of crude preparations of 2-5A-dependent RNase suggest that 2-5A-dependent RNase may form dimers in concentrated but not in dilute extracts. See Slattery, E. et al., *Proc. Natl. Acad. Sci. U.S.A.*, 76: 4778–4782 (1979) and Wreschner, D. H. et al., *Eur. J. Biochem.*, 124: 261–268 (1982).

Comparison between the amino acid sequences of other ribonucleases with 2-5A-dependent RNase identifies some limited homology with RNase E, an endoribonuclease from *E. coli*. See FIG. 9A. See also Apirion D. and Lassar, A. B., *J. Biol. Chem.*, 253: 1738–1742 (1978) and Claverie-Martin, F. et al., *J. Biol. Chem.* 266: 2843–2851 (1991). The homology with RNase E is relatively conserved between the human and murine forms of 2-5A-dependent RNase and spans a region of about 200 amino acid residues. Within these regions there are 24 and 32% identical plus conservative matches, with some gaps, between RNase E and the human and murine forms of 2-5A-dependent RNase, respectively. See FIG. 9A. The rne gene which encodes RNase E and the altered mRNA stability (ams) gene, Ono, M. and Kumano, M., *J. Mol. Biol.*, 129: 343–357 (1979), map to the same genetic locus. See Mudd E. A. et al., *Mol. Microbiol.*, 4: 2127–2135 (1990); Babitzke, P. and Kushner, S. R., *Proc. Natl. Acad. Sci. U.S.A.*, 88: 1–5 (1991) and Taraseviciene, L. et al., *Mol. Microbiol.*, 5: 85–855 (1991). RNase E is required for both efficient mRNA turnover and rRNA processing in *E. coli*. See Mudd E. A. et al., *Mol. Microbiol.*, 4: 2127–2135 (1990) and Babitzke, P. and Kushner, S. R., *Proc. Natl. Acad. Sci. U.S.A.*, 88: 1–5 (1991). The cleavage specificities of 2-5A-dependent RNase and RNase E are similar in that 2-5A-dependent RNase cleaves mainly after UU or UA, Wreschner, D. H. et al., *Nature*, 289: 414–417 (1981a) and Floyd-Smith, G. et al., *Science*, 212: 1020–1032 (1981), and RNase E usually cleaves within the central AUU sequence of (G or A)AUU(A or U), Ehretsmann, C. P. et al., *Genes & Development*, 6: 149–159 (1992). The location of the RNase E homology and other identified features in 2-5A-dependent RNase are shown. See FIG. 9B. These findings raise the possibility that RNase E may be the ancestral precursor of 2-5A-dependent RNase. In this regard, there are indications of 2',5'-oligoadenylates in *E. coli*. See Brown, R. E. and Kerr, I. M., *Process in Clinical and Biological Research*, 202: 3–10 (1985) and Trujillo, M. A. et al., *Eur. J. Biochem.*, 169: 167–173 (1987). However, the evolutionary distribution of a complete 2-5A system (i.e. 2-5A synthetase and 2-5A-dependent RNase) is reported to begin only with reptiles or possibly amphibia. See Cayley, P. J. et al., *Biochem. Biophys. Res. Commun.*, 108: 1243–1250 (1982).

Endoribonucleases play a controlling role in RNA metabolism by catalyzing the rate-limiting steps in RNA decay. See Brawerman, G., *Cell*, 57: 9–10 (1989). 2-5A-dependent RNase is a uniquely regulated endoribonuclease which mediates effects of interferon against picornaviruses. It functions by binding 2-5A and subsequently degrades both viral and cellular RNA. See Wreschner, D. H. et al., *Nucleic Acids Res.*, 9: 1571–1581 (1981b). In addition, the 2-5A system may be involved in the antiproliferative effects of interferon and in the fundamental control of RNA stability. Cellular levels of 2-5A-dependent RNase and/or 2-5A-synthetase are regulated during interferon-treatment, Hovanessian, A. G. et al., *Nature*, 268: 537–539 (1977) and Jacobsen, H. et al., *Virology*, 125: 496–501 (1983a), cell growth arrest, Stark, G. et al., *Nature*, 278: 471–473 (1979) and Jacobsen, H. et al., *Proc. Natl. Acad. Sci. U.S.A.*, 80: 4954–4958 (1983b), cell differentiation, Krause, D. et al., *Eur. J. Biochem.*, 146: 611–618 (1985), changing hormone status, e.g., Stark, G. et al., *Nature*, 278: 471–473 (1979), and liver regeneration, Etienne-Smekens, M. et al., *Proc. Natl. Acad. Sci. U.S.A.*, 80: 4609–4613 (1983). However, basal levels of 2-5A-dependent RNase and 2-5A synthetase are present in most if not all mammalian cells. The existence of multiple forms of 2-5A synthetase with different intracellular locations, Hovanessian, A. G. et al., *EMBO J.*, 6: 1273–1280 (1987), could indicate diverse functions for the 2-5A system. Similarly, the ubiquitous presence of the 2-5A system in higher animals suggests an important function for 2-5A-dependent RNase, Cayley, P. J. et al., *Biochem. Biophys. Res. Commun.*, 108: 1243–1250 (1982). For instance, 2-5A-dependent RNase cleaves rRNA at specific sites in intact ribosomes, Wreschner, D. H. et al., *Nucleic Acids Res.*, 9: 1571–1581 (1981b) and Silverman, R. H. et al., *J. Virol.*, 46: 1051–1055 (1983), possibly affecting translation rates. The transient nature of 2-5A, Williams, B. R. G. et al., *Eur. J. Biochem.*, 92: 455–562 (1978), and its growth inhibitory effect after introduction into cells, Hovanessian, A. G. and Wood, J. N., *Virology*, 101: 81–89 (1980), indicate that the 2-5A system is a tightly regulated pathway.

EXAMPLE

The source of mRNA for preparing the cDNA library is murine L929 cells grown in EMEM (Whittaker, Inc.) and supplemented with about 10% FBS (Gibco-BRL), and antibiotics. The cells are treated with about 50 µg per ml of cycloheximide and 1000 units per ml of murine interferon $(\alpha+\beta)$ $(1.3\times10^7$ units per mg protein: Lee Biomolecular) for about 2.5 hours to increase levels of 2-5A-dependent RNase mRNA. Total RNA was then isolated, e.g. Chomczynski, P. and Sacchi, N., *Anal. Biochem.*, 162: 156–159 (1987), from which poly(A)$^+$ RNA is prepared by oligo(dT)-cellulose chromatography as described. See Sambrook, J. et al., *Cold Spring Harbor Laboratory Press* (1989). Synthesis of the first strand of cDNA is done by using reverse transcriptase as described (Superscript; BRL) except that 5-methyl-dCTP is substituted for dCTP and an XhoI-oligo-dT adapter-primer (Stratagene) is used. Synthesis of the second strand of cDNA and ligation of EcoRI linker was as described (Stratagene). The cDNA is digested with EcoRI and XhoI and unidirectionally cloned into predigested λZAPII vector (Stratagene). The library is packaged by using Gigapack Gold extract and titered on PLK-F bacteria.

The cDNA library is screened directly without prior amplification at a density of about 25,000 phage per 150 mm plate. Phage are grown for 3.5 hours at about 42° C. until plaques are visible. Nitrocellulose filters saturated in IPTG (10 mM) and then dried, are overlaid on the plates and growth was continued for an additional 4 to 6 hours at 37° C. The filters are processed by a modification of the methods of Singh, H. et al., Cell, 52: 415–423 (1988) and Singh, H. et al., BioTechniques, 7: 252–261 (1989). Filters are washed in ice-cold binding buffer (about 20 mM Tris-HCl, about pH 7.5, about 20 mM magnesium acetate, about 50 mM potassium chloride, about 1 mM EDTA, about 50 mM β-mercaptoethanol, about 0.1 mM PMSF, about 5% glycerol) containing about 6M guanidine-HCl for about 20 min. The solution containing the filters is then diluted two-fold with binding buffer and washing on ice is continued for about an additional 5 minutes; serial two-fold dilutions were continued until the guanidine concentration was about 187 mM. The filters are then washed twice with binding buffer, and incubated with binding buffer containing about 5% nonfat milk for one hour at about room temperature. The filters are then washed twice with binding buffer and incubated in binding buffer (supplemented with about 0.25% nonfat dry milk and about 0.02% sodium azide) containing $p(A2'p)_2(br^8A2'p)_2A3'$-[32P]Cp (the "2-5A probe"), Nolan-Sorden, N. L. et al., Anal. Biochem., 184: 298–304 (1990), at about $2 \times 10^5$ counts per minute per ml (about 3,000 Ci per mmole) at about 4° C. with shaking for about 24 hours. The filters are washed twice with binding buffer and then twice with water before air drying and exposing to film.

Murine L929 cells are treated with about 1000 units per ml interferon (α+β) with or without about 50 μg per ml of cycloheximide and the total RNA is then isolated as described. See Chomczynski, P. and Sacchi, N., Anal. Biochem., 162: 156–159 (1987). Poly(A)$^+$ RNA is prepared by oligo(dT)-cellulose chromatography, as described in Sambrook, J. et al., Cold Spring Harbor Laboratory Press (1989), and is separated on glyoxal agarose gels and transferred to Nytran membranes. RNA is immobilized on the membrane by uv crosslinking (Stratalinker, Stratagene). The murine 2-5A-dependent RNase cDNA is $^{32}$P-labeled by random priming and then hybridized to the filter [about 50% formamide, about 10% dextran sulphate, Denhardt's solution about 1% SDS, 6× SSPE, Sambrook, J. et al., Cold Spring Harbor Laboratory Press (1989), about 250 μg per ml salmon sperm DNA] at about 42° C.

The Human 2-5A-dependent RNase cDNA clone, HZB1, is isolated from an adult human kidney cDNA library in λgt10 with radiolabeled (random primed) murine 2-5A-dependent RNase cDNA (clone ZB1) as probe, Sambrook, J. et al., Cold Spring Harbor Laboratory Press (1989). Clone HBZ22 is isolated using radiolabeled HZB1 DNA as probe. The genomic human 2-5A-dependent RNase clone is isolated from a human placenta cosmid library in vector pVE15 (Stratagene) with a radiolabeled fragment of HZB22 DNA as probe. The murine genomic 2-5A-dependent RNase clone is isolated from a mouse 129SV genomic library in vector λFIXII (Stratagene) with a radiolabeled fragment of 2-5A-BP cDNA (clone ZB1) as probe. Subcloning of DNA is in Bluescript vectors (Stratagene).

Transcription of plasmids with phage RNA polymerases is in the presence of mGppppG as described (Promega) except that reaction mixtures are supplemented with 15% dimethyl sulfoxide and incubations are at about 37° C. for about 90 minutes. RNA is purified through Sephadex G50 spun-columns and ethanol precipitated prior to translation. Protein synthesis was performed, as described (Promega), at about 30° C. for about one hour in micrococcal nuclease-pretreated rabbit reticulocyte lysate or in an extract of wheat germ at about room temperature for about one hour and then at about 40° C. for about 12 hours. Translation reactions contain about 50 μM zinc sulfate. Endogenous 2-5A-dependent RNase in the reticulocyte lysated is removed by adsorption to about 30 μM of $p_2(A2'p)_3A$ covalently attached to cellulose (2-5A-cellulose), prepared as described in Wells, J. A. et al., J. Biol. Chem., 259: 1363–1370 (1984) and Silverman, R. H. and Krause, D., Lymphokines and Interferons: A Practical Approach, I.R.L. Press. Oxford, England, pp. 149–193 (1987), for about one hour on ice as described. See Silverman, R. H., Anal. Biochem., 144: 450–460 (1985). The 2-5A-dependent RNase: 2-5A-cellulose complex is removed by twice centrifuging at about 400×g for about 5 minutes at about 2° C. The supernatant completely lacking in measurable levels of 2-5A-dependent RNase. See FIG. 5.

The set of nested 3'-deletions of the truncated murine 2-5A-dependent RNase cDNA, ZB1, is generated with exonuclease III/S1 nuclease digestion followed by filling-in with Klenow DNA Polymerase using the "Erase-A-Base" system (Promega).

The synthesis of the 2-5A probe, $p(A2'p)_2(br^8A2'p)_2A$ [32P]Cp, and its crosslinking to 2-5A-dependent RNase is performed exactly as described. See Nolan-Sorden, N. L. et al., Anal. Biochem., 184: 298–304 (1990). Briefly, the 2-5A probe, about 0.7 to 2.5 nM at 3,0009 Ci/mmole, is incubated for about one hour on ice with cell extract prepared as described, Silverman, R. H. and Krause, D., Lymphokines and Interferons: A Practical Approach, I.R.L. Press, Oxford. England, pp. 149–193 (1987), in the absence or presence of unlabeled oligonucleotide competitors. Covalent crosslinking is done under a uv lamp (308 nm) for one hour on ice and the proteins are separated on SDS/10% polyacrylamide gels. Filter assays for 2-5A binding activity using the 2-5A probe for about one hour on ice, as described in Knight, M. et al., Nature, 288: 189–192 (1980).

Protease digestions are performed on gel-purified proteins in a gel, as described by Cleveland, D. W. et al., J. Biol. Chem., 252: 1102–1106 (1977).

The ribonuclease assay with 2-5A-cellulose is performed, as described by Silverman, R. H., Anal. Biochem., 144: 450–460 (1985). Briefly, lysates are adsorbed to about 30 μM of 2-5A-cellulose on ice for about two hours. The matrix is then washed three times by centrifuging and resuspending in buffer A. See Silverman, R. H., Anal. Biochem., 144: 450–460 (1985). The matrix is then incubated with poly(U)-[$^{32}$P]Cp or poly(C)-[$^{32}$P]Cp (both at about 16 μM in nucleotide equivalents) at about 30° C. and the levels of acid-precipitable radioactive RNA are determined by filtration on glass-fiber filters.

The Sanger dideoxy sequencing method is used to determine the DNA sequences (Sequenase, United States Biomedical).

The lysines in the truncated murine 2-5A-dependent RNase, clone ZB1, at positions 240 and 274 are mutated, individually and together, to asparagine residues. Mutants ZB1 ($Lys^{274} \rightarrow Asn$) and the double mutant, ZB1($Lys^{240, 274} \rightarrow Asn$), are obtained with mutant oligonucleotides after subcloning ZB1 cDNA into pALTER-1 as described (Promega). Mutant ZB1 ($Lys^{240} \rightarrow Asn$) is obtained after polymerase chain reaction amplification of a segment of ZB1 with an upstream primer containing a unique HincII site attached to the mutant sequence and a second primer downstream of a unique BglII site. The HincII- and BGIII-digested polymerase chain reaction product and similarly-digested clone ZB1are then ligated. The specific mutations are: for codon 240, AAA→AAC and for codon 274, AAG→AAC. Mutants are confirmed by DNA sequencing.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced herein.

TABLE 1

Human 2-5A-depedent RNase
SEQ ID NO:1: and SEQ ID NO:2:

```
                   -103 aatcccaacttacactcaaagct tctttgattaagtgctaggagataaatttgcattttctca aggaaaaggctaaaagtggtagcaggtggcatttaccgtc ATG GAG AGC AGG GAT CAT AAC AAC CCC CAG       30
Met Glu Ser Arg Asp His Asn Asn Pro Gln       10

GAG GGA CCC ACG TCC TCC AGC GGT AGA AGG       60
Glu Gly Pro Thr Ser Ser Ser Gly Arg Arg       20

GCT GCA GTG GAA GAC AAT CAC TTG CTG ATT       90
Ala Ala Val Glu Asp Asn His Leu Leu Ile       30

AAA GCT GTT CAA AAC GAA GAT GTT GAC CTG      120
Lys Ala Val Gln Asn Glu Asp Val Asp Leu       40

GTC CAG CAA TTG CTG GAA GGT GGA GCC AAT      150
Val Gln Gln Leu Leu Glu Gly Gly Ala Asn       50

GTT AAT TTC CAG GAA GAG GAA GGG GGC TGG      180
Val Asn Phe Gln Glu Glu Glu Gly Gly Trp       60

ACA CCT CTG CAT AAC GCA GTA CAA ATG AGC      210
Thr Pro Leu His Asn Ala Val Gln Met Ser       70

AGG GAG GAC ATT GTG GAA CTT CTG CTT CGT      240
Arg Glu Asp Ile Val Glu Leu Leu Leu Arg       80

CAT GGT GCT GAC CCT GTT CTG AGG AAG AAG      270
His Gly Ala Asp Pro Val Leu Arg Lys Lys       90

AAT GGG GCC ACG CTT TTT ATC CTC GCA GCG      300
Asn Gly Ala Thr Leu Phe Ile Leu Ala Ala      100

ATT GCG GGG AGC GTG AAG CTG CTG AAA CTT      330
Ile Ala Gly Ser Val Lys Leu Leu Lys Leu      110

TTC CTT TCT AAA GGA GCA GAT GTC AAT GAG      360
Phe Leu Ser Lys Gly Ala Asp Val Asn Glu      120

TGT GAT TTT TAT GGC TTC ACA GCC TTC ATG      390
Cys Asp Phe Tyr Gly Phe Thr Ala Phe Met      130

GAA GCC GCT GTG TAT GGT AAG GTC AAA GCC      420
Glu Ala Ala Val Tyr Gly Lys Val Lys Ala      140

CTA AAA TTC CTT TAT AAG AGA GGA GCA AAT      450
Leu Lys Phe Leu Tyr Lys Arg Gly Ala Asn      150

GTG AAT TTG AGG CGA AAG ACA AAG GAG GAT      480
Val Asn Leu Arg Arg Lys Thr Lys Glu Asp      160

CAA GAG CGG CTG AGG AAA GGA GGG GCC ACA      510
```

TABLE 1-continued

Human 2-5A-depedent RNase
SEQ ID NO:1: and SEQ ID NO:2:

```
Gln Glu Arg Leu Arg Lys Gly Gly Ala Thr      170

GCT CTC ATG GAC GCT GCT GAA AAA GGA CAC      540
Ala Leu Met Asp Ala Ala Glu Lys Gly His      180

GTA GAG GTC TTG AAG ATT CTC CTT GAT GAG      570
Val Glu Val Leu Lys Ile Leu Leu Asp Glu      190

ATG GGG GCA GAT GTA AAC GCC TGT GAC AAT      600
Met Gly Ala Asp Val Asn Ala Cys Asp Asn      200

ATG GGC AGA AAT GCC TTG ATC CAT GCT CTC      630
Met Gly Arg Asn Ala Leu Ile His Ala Leu      210

CTG AGC TCT GAC GAT AGT GAT GTG GAG GCT      660
Leu Ser Ser Asp Asp Ser Asp Val Glu Ala      220

ATT ACG CAT CTG CTG CTG GAC CAT GGG GCT      690
Ile Thr His Leu Leu Leu Asp His Gly Ala      230

GAT GTC AAT GTG AGG GGA GAA AGA GGG AAG      720
Asp Val Asn Val Arg Gly Glu Arg Gly Lys      240

ACT CCC CTG ATC CTG GCA GTG GAG AAG AAG      750
Thr Pro Leu Ile Leu Ala Val Glu Lys Lys      250

CAC TTG GGT TTG GTG CAG AGG CTT CTG GAG      780
His Leu Gly Leu Val Gln Arg Leu Leu Glu      260

CAA GAG CAC ATA GAG ATT AAT GAC ACA GAC      810
Gln Glu His Ile Glu Ile Asn Asp Thr Asp      270

AGT GAT GGC AAA ACA GCA CTG CTG CTT GCT      840
Ser Asp Gly Lys Thr Ala Leu Leu Leu Ala      280

GTT GAA CTC AAA CTG AAG AAA ATC GCC GAG      870
Val Glu Leu Lys Leu Lys Lys Ile Ala Glu      290

TTG CTG TGC AAA CGT GGA GCC AGT ACA GAT      900
Leu Leu Cys Lys Arg Gly Ala Ser Thr Asp      300

TGT GGG GAT CTT GTT ATG ACA GCG AGG CGG      930
Cys Gly Asp Leu Val Met Thr Ala Arg Arg      310

AAT TAT GAC CAT TCC CTT GTG AAG GTT CTT      960
Asn Tyr Asp His Ser Leu Val Lys Val Leu      320

CTC TCT CAT GGA GCC AAA GAA GAT TTT CAC      990
Leu Ser His Gly Ala Lys Glu Asp Phe His      330

CCT CCT GCT GAA GAC TGG AAG CCT CAG AGC     1020
Pro Pro Ala Glu Asp Trp Lys Pro Gln Ser      340

TCA CAC TGG GGG GCA GCC CTG AAG GAT CTC     1050
Ser His Trp Gly Ala Ala Leu Lys Asp Leu      350

CAC AGA ATA TAC CGC CCT ATG ATT GGC AAA     1080
His Arg Ile Tyr Arg Pro Met Ile Gly Lys      360

CTC AAG TTC TTT ATT GAT GAA AAA TAC AAA     1110
Leu Lys Phe Phe Ile Asp Glu Lys Tyr Lys      370

ATT GCT GAT ACT TCA GAA GGA GGC ATC TAC     1140
Ile Ala Asp Thr Ser Glu Gly Gly Ile Tyr      380

CTG GGG TTC TAT GAG AAG CAA GAA GTA GCT     1170
Leu Gly Phe Tyr Glu Lys Gln Glu Val Ala      390

GTG AAG ACG TTC TGT GAG GGC AGC CCA CGT     1200
Val Lys Thr Phe Cys Glu Gly Ser Pro Arg      400

GCA CAG CGG GAA GTC TCT TGT CTG CAA AGC     1230
Ala Gln Arg Glu Val Ser Cys Leu Gln Ser      410

AGC CGA GAG AAC AGT CAC TTG GTG ACA TTC     1260
Ser Arg Glu Asn Ser His Leu Val Thr Phe      420
```

TABLE 1-continued

Human 2-5A-depedent RNase
SEQ ID NO:1: and SEQ ID NO:2:

| | | | | | | | | |
|---|---|---|---|---|---|---|---|---|
| TAT | GGG | AGT | GAG | AGC | CAC | AGG | GGC | CAC | TTG | 1290 |
| Tyr | Gly | Ser | Glu | Ser | His | Arg | Gly | His | Leu | 430 |

```
TAT GGG AGT GAG AGC CAC AGG GGC CAC TTG    1290
Tyr Gly Ser Glu Ser His Arg Gly His Leu     430

TTT GTG TGT GTC ACC CTC TGT GAG CAG ACT    1320
Phe Val Cys Val Thr Leu Cys Glu Gln Thr     440

CTG GAA GCG TGT TTG GAT GTG CAC AGA GGG    1350
Leu Glu Ala Cys Leu Asp Val His Arg Gly     450

GAA GAT GTG GAA AAT GAG GAA GAT GAA TTT    1380
Glu Asp Val Glu Asn Glu Glu Asp Glu Phe     460

GCC CGA AAT GTC CTG TCA TCT ATA TTT AAG    1410
Ala Arg Asn Val Leu Ser Ser Ile Phe Lys     470

GCT GTT CAA GAA CTA CAC TTG TCC TGT GGA    1440
Ala Val Gln Glu Leu His Leu Ser Cys Gly     480

TAC ACC CAC CAG GAT CTG CAA CCA CAA AAC    1470
Tyr Thr His Gln Asp Leu Gln Pro Gln Asn     490

ATC TTA ATA GAT TCT AAG AAA GCT GCT CAC    1500
Ile Leu Ile Asp Ser Lys Lys Ala Ala His     500

CTG GCA GAT TTT GAT AAG AGC ATC AAG TGG    1530
Leu Ala Asp Phe Asp Lys Ser Ile Lys Trp     510

GCT GGA GAT CCA CAG GAA GTC AAG AGA GAT    1560
Ala Gly Asp Pro Gln Glu Val Lys Arg Asp     520

CTA GAG GAC CTT GGA CGG CTG GTC CTC TAT    1590
Leu Glu Asp Leu Gly Arg Leu Val Leu Tyr     530

GTG GTA AAG AAG GGA AGC ATC TCA TTT GAG    1620
Val Val Lys Lys Gly Ser Ile Ser Phe Glu     540

GAT CTG AAA GCT CAA AGT AAT GAA GAG GTG    1650
Asp Leu Lys Ala Gln Ser Asn Glu Glu Val     550

GTT CAA CTT TCT CCA GAT GAG GAA ACT AAG    1680
Val Gln Leu Ser Pro Asp Glu Glu Thr Lys     560

GAC CTC ATT CAT CGT CTC TTC CAT CCT GGG    1710
Asp Leu Ile His Arg Leu Phe His Pro Gly     570

GAA CAT GTG AGG GAC TGT CTG AGT GAC CTG    1740
Glu His Val Arg Asp Cys Leu Ser Asp Leu     580

CTG GGT CAT CCC TTC TTT TGG ACT TGG GAG    1770
Leu Gly His Pro Phe Phe Trp Thr Trp Glu     590

AGC CGC TAT AGG ACG CTT CGG AAT GTG GGA    1800
Ser Arg Tyr Arg Thr Leu Arg Asn Val Gly     600

AAT GAA TCC GAC ATC AAA ACA CGA AAA TCT    1830
Asn Glu Ser Asp Ile Lys Thr Arg Lys Ser     610

GAA AGT GAG ATC CTC AGA CTA CTG CAA CCT    1860
Glu Ser Glu Ile Leu Arg Leu Leu Gln Pro     620

GGG CCT TCT GAA CAT TCC AAA AGT TTT GAC    1890
Gly Pro Ser Glu His Ser Lys Ser Phe Asp     630

AAG TGG ACG ACT AAG ATT AAT GAA TGT GTT    1920
Lys Trp Thr Thr Lys Ile Asn Glu Cys Val     640

ATG AAA AAA ATG AAT AAG TTT TAT GAA AAA    1950
Met Lys Lys Met Asn Lys Phe Tyr Glu Lys     650

AGA GGC AAT TTC TAC CAG AAC ACT GTG GGT    1980
Arg Gly Asn Phe Tyr Gln Asn Thr Val Gly     660

GAT CTG CTA AAG TTC ATC CGG AAT TTG GGA    1210
Asp Leu Leu Lys Phe Ile Arg Asn Leu Gly     670

GAA CAC ATT GAT GAA GAA AAG CAT AAA AAG    2040
Glu His Ile Asp Glu Glu Lys His Lys Lys     680

ATG AAA TTA AAA ATT GGA GAC CCT TCC CTG    2070
Met Lys Leu Lys Ile Gly Asp Pro Ser Leu     690

TAT TTT CAG AAG ACA TTT CCA GAT CTG GTG    2100
Tyr Phe Gln Lys Thr Phe Pro Asp Leu Val     700

ATC TAT GTC TAC ACA AAA CTA CAG AAC ACA    2130
Ile Tyr Val Tyr Thr Lys Leu Gln Asn Thr     710

GAA TAT AGA AAG CAT TTC CCC CAA ACC CAC    2160
Glu Tyr Arg Lys His Phe Pro Gln Thr His     720

AGT CCA AAC AAA CCT CAG TGT GAT GGA GCT    2190
Ser Pro Asn Lys Pro Gln Cys Asp Gly Ala     730

GGT GGG GCC AGT GGG TTG GCC AGC CCT GGG    2220
Gly Gly Ala Ser Gly Leu Ala Ser Pro Gly     740

TGC                                          2223
Cys                                           741 tgatggactgatttgctggagttcagggaactact          2258 tattagctgtagagtccttggcaaatcacaacat           2292 tctgggccttttaactcaccaggttgcttgtgagggat       2330 gagttgcatagctgatatgtcagtccctggcatcgtg        2367 tattccatatgtctataacaaaagcaatatatacccag       2405 actacactagtccataagctttacccactaactggga        2442 ggacattctgctaagattcctttttgtcaattgcaccaa      2480 aagaatgagtgccttgacccctaatgctgcatatgtt        2517 acaattctctcacttaattttcccaatgatcttgcaaa       2555 acagggattatcatccccatttaagaactgaggaacc        2592 tgagactcagagagtgtgagctactgcccaagattat        2630 tcaatttatacctagcactttataaatttatgtggtg        2667 ttattggtacctctcatttgggcaccttaaaacttaac       2705 tatcttccagggctcttccagatgaggcccaaaacat        2742 atatagggggttccaggaatctcattcattcattcagta      2780 tttattgagcatctagtataagtctgggcactggatg        2817 catgaatt                                     2825
```

TABLE 2

Murine 2-5A-dependent RNase (partial)
SEQ ID NO:3: and SEQ ID NO:4:

```
-163
attcggcacgaggaaggtgccaattactagctcccttctttattcgtgta ctgatgagatgtcagaagacagaacataatcagcccaatccctactccaa gactctcattgtgtcccaaagaaacacacgtgtgcatttcccaaggaaaa ggcattgaggacc   ATG GAG ACC CCG GAT TAT    18
                Met Glu Thr Pro Asp Tyr     6
```

TABLE 2-continued

Murine 2-5A-dependent RNase (partial)
SEQ ID NO:3: and SEQ ID NO:4:

| | |
|---|---|
| AAC ACA CCT CAG GGT GGA ACC CCA TCA GCG<br>Asn Thr Pro Gln Gly Gly Thr Pro Ser Ala | 48<br>16 |
| GGA AGT CAG AGG ACC GTT GTC GAA GAT GAT<br>Gly Ser Gln Arg Thr Val Val Glu Asp Asp | 78<br>26 |
| TCT TCG TTG ATC AAA GCT GTT CAG AAG GGA<br>Ser Ser Leu Ile Lys Ala Val Gln Lys Gly | 108<br>36 |
| GAT GTT GTC AGG GTC CAG CAA TTG TTA GAA<br>Asp Val Val Arg Val Gln Gln Leu Leu Glu | 138<br>46 |
| AAA GGG GCT GAT GCC AAT GCC TGT GAA GAC<br>Lys Gly Ala Asp Ala Asn Ala Cys Glu Asp | 168<br>56 |
| ACC TGG GGC TGG ACA CCT TTG CAC AAC GCA<br>Thr Trp Gly Trp Thr Pro Leu His Asn Ala | 198<br>66 |
| GTG CAA GCT GGC AGG GTA GAC ATT GTG AAC<br>Val Gln Ala Gly Arg Val Asp Ile Val Asn | 228<br>76 |
| CTC CTG CTT AGT CAT GGT GCT GAC CCT CAT<br>Leu Leu Leu Ser His Gly Ala Asp Pro His | 258<br>86 |
| CGG AGG AAG AAG AAT GGG GCC ACC CCC TTC<br>Arg Arg Lys Lys Asn Gly Ala Thr Pro Phe | 288<br>96 |
| ATC ATT GCT GGG ATC CAG GGA GAT GTG AAA<br>Ile Ile Ala Gly Ile Gln Gly Asp Val Lys | 318<br>106 |
| CTG CTC GAG ATT CTC CTC TCT TGT GGT GCA<br>Leu Leu Glu Ile Leu Leu Ser Cys Gly Ala | 384<br>116 |
| GAC GTC AAT GAG TGT GAC GAG AAC GGA TTC<br>Asp Val Asn Glu Cys Asp Glu Asn Gly Phe | 378<br>126 |
| ACG GCT TTC ATG GAA GCT GCT GAG CGT GGT<br>Thr Ala Phe Met Glu Ala Ala Glu Arg Gly | 408<br>136 |
| AAC GCT GAA GCC TTA AGA TTC CTT TTT GCT<br>Asn Ala Glu Ala Leu Arg Phe Leu Phe Ala | 438<br>146 |
| AAG GGA GCC AAT GTG AAT TTG CGA CGA CAG<br>Lys Gly Ala Asn Val Asn Leu Arg Arg Gln | 468<br>156 |
| ACA ACG AAG GAC AAA AGG CGA TTG AAG CAA<br>Thr Thr Lys Asp Lys Arg Arg Leu Lys Gln | 498<br>166 |
| GGA GGC GCC ACA GCT CTC ATG AGC GCT GCT<br>Gly Gly Ala Thr Ala Leu Met Ser Ala Ala | 528<br>176 |
| GAG AAG GGC CAC CTG GAA GTC CTG AGA ATT<br>Glu Lys Gly His Leu Glu Val Leu Arg Ile | 558<br>186 |
| CTC CTC AAT GAC ATG AAG GCA GAA GTC GAT<br>Leu Leu Asn Asp Met Lys Ala Glu Val Asp | 588<br>196 |
| GCT CGG GAC AAC ATG GGC AGA AAT GCC CTG<br>Ala Arg Asp Asn Met Gly Arg Asn Ala Leu | 618<br>206 |
| ATC CGT ACT CTG CTG AAC TGG GAT TGT GAA<br>Ile Arg Thr Leu Leu Asn Trp Asp Cys Glu | 648<br>216 |
| AAT GTG GAG GAG ATT ACT TCA ATC CTG ATT<br>Asn Val Glu Glu Ile Thr Ser Ile Leu Ile | 678<br>226 |
| CAG CAC GGG GCT GAT GTT AAC GTG AGA GGA<br>Gln His Gly Ala Asp Val Asn Val Arg Gly | 708<br>236 |
| GAA AGA GGG AAA ACA CCC CTC ATC GCA GCA<br>Glu Arg Gly Lys Thr Pro Leu Ile Ala Ala | 738<br>246 |
| GTG GAG AGG AAG CAC ACA GGC TTG GTG CAG<br>Val Glu Arg Lys His Thr Gly Leu Val Gln | 768<br>256 |
| ATG CTC CTG AGT CGG GAA GGC ATA AAC ATA<br>Met Leu Leu Ser Arg Glu Gly Ile Asn Ile | 798<br>266 |
| GAT GCC AGG GAT AAC GAG GGC AAG ACA GCT<br>Asp Ala Arg Asp Asn Glu Gly Lys Thr Ala | 828<br>276 |
| CTG CTA ATT GCT GTT GAT AAA CAA CTG AAG<br>Leu Leu Ile Ala Val Asp Lys Gln Leu Lys | 858<br>286 |
| GAA ATT GTC CAG TTG CTT CTT GAA AAG GGA<br>Glu Ile Val Gln Leu Leu Leu Glu Lys Gly | 888<br>296 |
| GCT GAT AAG TGT GAC GAT CTT GTT TGG ATA<br>Ala Asp Lys Cys Asp Asp Leu Val Trp Ile | 918<br>306 |
| GCC AGG AGG AAT CAT GAC TAT CAC CTT GTA<br>Ala Arg Arg Asn His Asp Tyr His Leu Val | 948<br>316 |
| AAG CTT CTC CTC CCT TAT GTA GCT AAT CCT<br>Lys Leu Leu Leu Pro Tyr Val Ala Asn Pro | 978<br>326 |
| GAC ACC GAC CCT CCT GCT GGA GAC TGG TCG<br>Asp Thr Asp Pro Pro Ala Gly Asp Trp Ser | 1008<br>336 |
| CCT CAC AGT TCA CGT TGG GGG ACA GCC TTG<br>Pro His Ser Ser Arg Trp Gly Thr Ala Leu | 1038<br>346 |
| AAA AGC CTC CAC AGT ATG ACT CGA CCC ATG<br>Lys Ser Leu His Ser Met Thr Arg Pro Met | 1068<br>356 |
| ATT GGC AAA CTC AAG ATC TTC ATT CAT GAT<br>Ile Gly Lys Leu Lys Ile Phe Ile His Asp | 1098<br>366 |
| GAC TAT AAA ATT GCT GGC ACT TCC GAA GGG<br>Asp Tyr Lys Ile Ala Gly Thr Ser Glu Gly | 1128<br>376 |
| GCT GTC TAC CTA GGG ATC TAT GAC AAT CGA<br>Ala Val Tyr Leu Gly Ile Tyr Asp Asn Arg | 1158<br>386 |
| GAA GTG GCT GTG AAG GTC TTC CGT GAG AAT<br>Glu Val Ala Val Lys Val Phe Arg Glu Asn | 1188<br>396 |
| AGC CCA CGT GGA TGT AAG GAA GTC TCT TGT<br>Ser Pro Arg Gly Cys Lys Glu Val Ser Cys | 1218<br>406 |
| CTG CGG GAC TGC GGT GAC CAC AGT AAC TTA<br>Leu Arg Asp Cys Gly Asp His Ser Asn Leu | 1248<br>416 |
| GTG GCT TTC TAT GGA AGA GAG GAC GAT AAG<br>Val Ala Phe Tyr Gly Arg Glu Asp Asp Lys | 1278<br>426 |
| GGC TGT TTA TAT GTG TGT GTG TCC CTG TGT<br>Gly Cys Leu Tyr Val Cys Val Ser Leu Cys | 1308<br>436 |
| GAG TGG ACA CTG GAA GAG TTC CTG AGG TTG<br>Glu Trp Thr Leu Glu Glu Phe Leu Arg Leu | 1338<br>446 |
| CCC AGA GAG GAA CCT GTG GAG AAC GGG GAA<br>Pro Arg Glu Glu Pro Val Glu Asn Gly Glu | 1368<br>456 |
| GAT AAG TTT GCC CAC AGC ATC CTA TTA TCT<br>Asp Lys Phe Ala His Ser Ile Leu Leu Ser | 1398<br>466 |
| ATA TTT GAG GGT GTT CAA AAA CTA CAC TTG<br>Ile Phe Glu Gly Val Gln Lys Leu His Leu | 1428<br>476 |
| CAT GGA TAT TCC CAT CAG GAC CTG CAA CCA<br>His Gly Tyr Ser His Gln Asp Leu Gln Pro | 1458<br>486 |
| CAA AAC ATC TTA ATA GAT TCC AAG AAA GCT<br>Gln Asn Ile Leu Ile Asp Ser Lys Lys Ala | 1488<br>496 |
| GTC CGG CTG GCA GAT TTT GAT GAG AGC ATC<br>Val Arg Leu Ala Asp Phe Asp Glu Ser Ile | 1518<br>506 |
| CGA TGG ATG GGA GAG TCA CAG ATG GTC AGG<br>Arg Trp Met Gly Glu Ser Gln Met Val Arg | 1548<br>516 |

TABLE 2-continued

Murine 2-5A-dependent RNase (partial)
SEQ ID NO:3: and SEQ ID NO:4:

| | | |
|---|---|---|
| AGA GAC TTG GAG GAT CTT GGA CGG CTG GTT | 1578 | |
| Arg Asp Leu Glu Asp Leu Gly Arg Leu Val | 526 | |
| CTC TAC GTG GTA ATG AAA GGT GAG ATC CCC | 1608 | |
| Leu Tyr Val Val Met Lys Gly Glu Ile Pro | 536 | |
| TTT GAG ACA CTA AAG ACT CAG AAT GAT GAA | 1638 | |
| Phe Glu Thr Leu Lys Thr Gln Asn Asp Glu | 546 | |
| GTG CTG CTT ACA ATG TCT CCA GAT GAG GAG | 1668 | |
| Val Leu Leu Thr Met Ser Pro Asp Glu Glu | 556 | |
| ACT AAG GAC CTC ATT CAT TGC CTG TTT TCT | 1698 | |
| Thr Lys Asp Leu Ile His Cyc Leu Phe Ser | 566 | |
| CCT GGA GAA AAT GTC AAG AAC TGC CTG GTA | 1728 | |
| Pro Gly Glu Asn Val Lys Asn Cys Leu Val | 576 | |
| GAC CTG CTT GGC CAT CCT TTC TTT TGG ACT | 1758 | |
| Asp Leu Leu Gly His Pro Phe Phe Trp Thr | 586 | |
| TGG GAG AAC CGC TAT AGA ACA CTC CGG AAT | 1788 | |
| Trp Glu Asn Arg Tyr Arg Thr Leu Arg Asn | 596 | |
| GTG GGA AAT GAA TCT GAC ATC AAA GTA CGG | 1818 | |
| Val Gly Asn Glu Ser Asp Ile Lys Val Arg | 606 | |
| AAA TGT AAA AGT GAT CTT CTC AGA CTA CTG | 1848 | |
| Lys Cys Lys Ser Asp Leu Leu Arg Leu Leu | 616 | |
| CAG CAT CAG ACA CTT GAG CCT CCC AGA AGC | 1878 | |
| Gln His Gln Thr Leu Glu Pro Pro Arg Ser | 626 | |
| TTT GAC CAG TGG ACA TCT AAG ATC GAC AAA | 1908 | |
| Phe Asp Gln Trp Thr Ser Lys Ile Asp Lys | 636 | |
| AAT GTT ATG GAT GAA ATG AAT CAT TTC TAC | 1938 | |
| Asn Val Met Asp Glu Met Asn His Phe Tyr | 646 | |

TABLE 2-continued

Murine 2-5A-dependent RNase (partial)
SEQ ID NO:3: and SEQ ID NO:4:

| | | |
|---|---|---|
| GAA AAG AGA AAA AAA AAC CCT TAT CAG GAT | 1968 | |
| Glu Lys Arg Lys Lys Asn Pro Tyr Gln Asp | 656 | |
| ACT GTA GGT GAT CTG CTG AAG TTT ATT CGG | 1998 | |
| Thr Val Gly Asp Leu Leu Lys Phe Ile Arg | 666 | |
| AAT ATA GGC GAA CAC ATC AAT GAG GAA AAA | 2028 | |
| Asn Ile Gly Glu His Ile Asn Glu Glu Lys | 676 | |
| AAG CGG GGG | 2047 | |
| Lys Arg Gly | 679 | |

---

Having described our inventions, we claim:

1. An isolated, homogeneous, active 5'-phosphorylated, 2',5'-linked oligoadenylate (2-5A) dependent RNase, or an active fragment thereof, wherein said active RNase or active fragment thereof has a 2-5A binding domain and cleaves single stranded RNA when bound to 2-5A and wherein said active RNase or active fragment thereof is human.

2. The active RNase or active fragment thereof of claim 1, wherein said binding domain comprises an amino acid sequence designated as amino acid residue 229–275 of SEQ ID NO: 2.

3. The active RNase or active fragment thereof of claim 1, wherein said binding domain comprises a duplicated phosphate binding P-loop motif.

4. The active RNase or active fragment thereof of claim 3, wherein a first P-loop motif comprises an amino acid sequence designated as amino acids residues 229–241 of SEQ ID NO: 2 and a second P-loop motif comprises an amino acid sequence designated as amino acid residues 253–275 of SEQ ID NO: 2.

5. The active RNase or active fragment thereof of claim 1, wherein said active RNase or active fragment thereof has a cysteine-rich region containing 5 or 6 cysteine amino acid residues and wherein said cysteine-rich region comprises an amino acid sequence designated as amino acid residues 395–444 of SEQ ID NO:2.

6. A human isolated, homogeneous, active 5'-phosphorylated, 2',5'-linked oligoadenylate (2-5A) dependent RNase comprising an amino acid sequence designated as amino acid residues 1–741 of SEQ ID NO: 2.

7. An isolated, homogeneous, active 5'-phosphorylated, 2',5'-linked oligoadenylate (2-5A) dependent RNase, or an active fragment thereof, wherein said active RNase or active fragment thereof has a 2-5A binding domain and cleaves single stranded RNA when bound to 2-5A and wherein said active RNase or active fragment thereof is encoded by the nucleic acid sequence of SEQ ID NO: 1.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2928 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 104..2326

(xi) SEQUENCE DESCRIPTION: SEQ ID NO:1:

```
AATCCCAACT TACACTCAAA GCTTCTTTGA TTAAGTGCTA GGAGATAAAT TTGCATTTTC      60

TCAAGGAAAA GGCTAAAAGT GGTAGCAGGT GGCATTTACC GTC ATG GAG AGC AGG      115
                                                 Met Glu Ser Arg
                                                  1

GAT CAT AAC AAC CCC CAG GAG GGA CCC ACG TCC TCC AGC GGT AGA AGG      163
Asp His Asn Asn Pro Gln Glu Gly Pro Thr Ser Ser Ser Gly Arg Arg
```

|   |   |   |   |   |   |   |   |   |   |   |   |   |   |   |     |
|---|---|---|---|---|---|---|---|---|---|---|---|---|---|---|-----|
| GCT | GCA | GTG | GAA | GAC | AAT | CAC | TTG | CTG | ATT | AAA | GCT | GTT | CAA | AAC | GAA | 211 |
| Ala | Ala | Val | Glu | Asp | Asn | His | Leu | Leu | Ile | Lys | Ala | Val | Gln | Asn | Glu |
|  |  |  |  | 25 |  |  |  | 30 |  |  |  |  | 35 |  |  |

| GAT | GTT | GAC | CTG | GTC | CAG | CAA | TTG | CTG | GAA | GGT | GGA | GCC | AAT | GTT | AAT | 259 |
|---|---|---|---|---|---|---|---|---|---|---|---|---|---|---|---|---|
| Asp | Val | Asp | Leu | Val | Gln | Gln | Leu | Leu | Glu | Gly | Gly | Ala | Asn | Val | Asn |
|  |  |  | 40 |  |  |  |  | 45 |  |  |  | 50 |  |  |  |

| TTC | CAG | GAA | GAG | GAA | GGG | GGC | TGG | ACA | CCT | CTG | CAT | AAC | GCA | GTA | CAA | 307 |
|---|---|---|---|---|---|---|---|---|---|---|---|---|---|---|---|---|
| Phe | Gln | Glu | Glu | Glu | Gly | Gly | Trp | Thr | Pro | Leu | His | Asn | Ala | Val | Gln |
|  |  | 55 |  |  |  |  | 60 |  |  |  | 65 |  |  |  |  |

| ATG | AGC | AGG | GAG | GAC | ATT | GTG | GAA | CTT | CTG | CTT | CGT | CAT | GGT | GCT | GAC | 355 |
|---|---|---|---|---|---|---|---|---|---|---|---|---|---|---|---|---|
| Met | Ser | Arg | Glu | Asp | Ile | Val | Glu | Leu | Leu | Leu | Arg | His | Gly | Ala | Asp |
|  | 70 |  |  |  |  | 75 |  |  |  |  | 80 |  |  |  |  |

| CCT | GTT | CTG | AGG | AAG | AAG | AAT | GGG | GCC | ACG | CTT | TTT | ATC | CTC | GCA | GCG | 403 |
|---|---|---|---|---|---|---|---|---|---|---|---|---|---|---|---|---|
| Pro | Val | Leu | Arg | Lys | Lys | Asn | Gly | Ala | Thr | Leu | Phe | Ile | Leu | Ala | Ala |
| 85 |  |  |  |  | 90 |  |  |  |  | 95 |  |  |  |  | 100 |

| ATT | GCG | GGG | AGC | GTG | AAG | CTG | CTG | AAA | CTT | TTC | CTT | TCT | AAA | GGA | GCA | 451 |
|---|---|---|---|---|---|---|---|---|---|---|---|---|---|---|---|---|
| Ile | Ala | Gly | Ser | Val | Lys | Leu | Leu | Lys | Leu | Phe | Leu | Ser | Lys | Gly | Ala |
|  |  |  |  | 105 |  |  |  |  | 110 |  |  |  |  | 115 |  |

| GAT | GTC | AAT | GAG | TGT | GAT | TTT | TAT | GGC | TTC | ACA | GCC | TTC | ATG | GAA | GCC | 499 |
|---|---|---|---|---|---|---|---|---|---|---|---|---|---|---|---|---|
| Asp | Val | Asn | Glu | Cys | Asp | Phe | Tyr | Gly | Phe | Thr | Ala | Phe | Met | Glu | Ala |
|  |  |  | 120 |  |  |  |  | 125 |  |  |  |  | 130 |  |  |

| GCT | GTG | TAT | GGT | AAG | GTC | AAA | GCC | CTA | AAA | TTC | CTT | TAT | AAG | AGA | GGA | 547 |
|---|---|---|---|---|---|---|---|---|---|---|---|---|---|---|---|---|
| Ala | Val | Tyr | Gly | Lys | Val | Lys | Ala | Leu | Lys | Phe | Leu | Tyr | Lys | Arg | Gly |
|  |  | 135 |  |  |  |  | 140 |  |  |  |  | 145 |  |  |  |

| GCA | AAT | GTG | AAT | TTG | AGG | CGA | AAG | ACA | AAG | GAG | GAT | CAA | GAG | CGG | CTG | 595 |
|---|---|---|---|---|---|---|---|---|---|---|---|---|---|---|---|---|
| Ala | Asn | Val | Asn | Leu | Arg | Arg | Lys | Thr | Lys | Glu | Asp | Gln | Glu | Arg | Leu |
|  | 150 |  |  |  |  | 155 |  |  |  |  | 160 |  |  |  |  |

| AGG | AAA | GGA | GGG | GCC | ACA | GCT | CTC | ATG | GAC | GCT | GCT | GAA | AAA | GGA | CAC | 643 |
|---|---|---|---|---|---|---|---|---|---|---|---|---|---|---|---|---|
| Arg | Lys | Gly | Gly | Ala | Thr | Ala | Leu | Met | Asp | Ala | Ala | Glu | Lys | Gly | His |
| 165 |  |  |  |  | 170 |  |  |  |  | 175 |  |  |  |  | 180 |

| GTA | GAG | GTC | TTG | AAG | ATT | CTC | CTT | GAT | GAG | ATG | GGG | GCA | GAT | GTA | AAC | 691 |
|---|---|---|---|---|---|---|---|---|---|---|---|---|---|---|---|---|
| Val | Glu | Val | Leu | Lys | Ile | Leu | Leu | Asp | Glu | Met | Gly | Ala | Asp | Val | Asn |
|  |  |  |  | 185 |  |  |  |  | 190 |  |  |  |  | 195 |  |

| GCC | TGT | GAC | AAT | ATG | GGC | AGA | AAT | GCC | TTG | ATC | CAT | GCT | CTC | CTG | AGC | 739 |
|---|---|---|---|---|---|---|---|---|---|---|---|---|---|---|---|---|
| Ala | Cys | Asp | Asn | Met | Gly | Arg | Asn | Ala | Leu | Ile | His | Ala | Leu | Leu | Ser |
|  |  |  | 200 |  |  |  |  | 205 |  |  |  |  | 210 |  |  |

| TCT | GAC | GAT | AGT | GAT | GTG | GAG | GCT | ATT | ACG | CAT | CTG | CTG | CTG | GAC | CAT | 787 |
|---|---|---|---|---|---|---|---|---|---|---|---|---|---|---|---|---|
| Ser | Asp | Asp | Ser | Asp | Val | Glu | Ala | Ile | Thr | His | Leu | Leu | Leu | Asp | His |
|  |  | 215 |  |  |  |  | 220 |  |  |  |  | 225 |  |  |  |

| GGG | GCT | GAT | GTC | AAT | GTG | AGG | GGA | GAA | AGA | GGG | AAG | ACT | CCC | CTG | ATC | 835 |
|---|---|---|---|---|---|---|---|---|---|---|---|---|---|---|---|---|
| Gly | Ala | Asp | Val | Asn | Val | Arg | Gly | Glu | Arg | Gly | Lys | Thr | Pro | Leu | Ile |
|  |  | 230 |  |  |  |  | 235 |  |  |  |  | 240 |  |  |  |

| CTG | GCA | GTG | GAG | AAG | AAG | CAC | TTG | GGT | TTG | GTG | CAG | AGG | CTT | CTG | GAG | 883 |
|---|---|---|---|---|---|---|---|---|---|---|---|---|---|---|---|---|
| Leu | Ala | Val | Glu | Lys | Lys | His | Leu | Gly | Leu | Val | Gln | Arg | Leu | Leu | Glu |
| 245 |  |  |  |  | 250 |  |  |  |  | 255 |  |  |  |  | 260 |

| CAA | GAG | CAC | ATA | GAG | ATT | AAT | GAC | ACA | GAC | AGT | GAT | GGC | AAA | ACA | GCA | 931 |
|---|---|---|---|---|---|---|---|---|---|---|---|---|---|---|---|---|
| Gln | Glu | His | Ile | Glu | Ile | Asn | Asp | Thr | Asp | Ser | Asp | Gly | Lys | Thr | Ala |
|  |  |  |  | 265 |  |  |  |  | 270 |  |  |  |  | 275 |  |

| CTG | CTG | CTT | GCT | GTT | GAA | CTC | AAA | CTG | AAG | AAA | ATC | GCC | GAG | TTG | CTG | 979 |
|---|---|---|---|---|---|---|---|---|---|---|---|---|---|---|---|---|
| Leu | Leu | Leu | Ala | Val | Glu | Leu | Lys | Leu | Lys | Lys | Ile | Ala | Glu | Leu | Leu |
|  |  |  | 280 |  |  |  |  | 285 |  |  |  |  | 290 |  |  |

| TGC | AAA | CGT | GGA | GCC | AGT | ACA | GAT | TGT | GGG | GAT | CTT | GTT | ATG | ACA | GCG | 1027 |
|---|---|---|---|---|---|---|---|---|---|---|---|---|---|---|---|---|
| Cys | Lys | Arg | Gly | Ala | Ser | Thr | Asp | Cys | Gly | Asp | Leu | Val | Met | Thr | Ala |
|  |  | 295 |  |  |  |  | 300 |  |  |  |  | 305 |  |  |  |

| AGG | CGG | AAT | TAT | GAC | CAT | TCC | CTT | GTG | AAG | GTT | CTT | CTC | TCT | CAT | GGA | 1075 |
|---|---|---|---|---|---|---|---|---|---|---|---|---|---|---|---|---|
| Arg | Arg | Asn | Tyr | Asp | His | Ser | Leu | Val | Lys | Val | Leu | Leu | Ser | His | Gly |
|  | 310 |  |  |  |  | 315 |  |  |  |  | 320 |  |  |  |  |

| GCC | AAA | GAA | GAT | TTT | CAC | CCT | CCT | GCT | GAA | GAC | TGG | AAG | CCT | CAG | AGC | 1123 |
|---|---|---|---|---|---|---|---|---|---|---|---|---|---|---|---|---|
| Ala | Lys | Glu | Asp | Phe | His | Pro | Pro | Ala | Glu | Asp | Trp | Lys | Pro | Gln | Ser |

-continued

| | | | | | | | | | | | | | | |
|---|---|---|---|---|---|---|---|---|---|---|---|---|---|---|
| | 325 | | | | 330 | | | | 335 | | | | 340 | |
| TCA | CAC | TGG | GGG | GCA | GCC | CTG | AAG | GAT | CTC | CAC | AGA | ATA | TAC | CGC | CCT | 1171
| Ser | His | Trp | Gly | Ala | Ala | Leu | Lys | Asp | Leu | His | Arg | Ile | Tyr | Arg | Pro |
| | | | 345 | | | | | 350 | | | | 355 | | |

```
                 325                 330                 335                 340
TCA CAC TGG GGG GCA GCC CTG AAG GAT CTC CAC AGA ATA TAC CGC CCT           1171
Ser His Trp Gly Ala Ala Leu Lys Asp Leu His Arg Ile Tyr Arg Pro
             345                 350                 355

ATG ATT GGC AAA CTC AAG TTC TTT ATT GAT GAA AAA TAC AAA ATT GCT           1219
Met Ile Gly Lys Leu Lys Phe Phe Ile Asp Glu Lys Tyr Lys Ile Ala
             360                 365                 370

GAT ACT TCA GAA GGA GGC ATC TAC CTG GGG TTC TAT GAG AAG CAA GAA           1267
Asp Thr Ser Glu Gly Gly Ile Tyr Leu Gly Phe Tyr Glu Lys Gln Glu
             375                 380                 385

GTA GCT GTG AAG ACG TTC TGT GAG GGC AGC CCA CGT GCA CAG CGG GAA           1315
Val Ala Val Lys Thr Phe Cys Glu Gly Ser Pro Arg Ala Gln Arg Glu
             390                 395                 400

GTC TCT TGT CTG CAA AGC AGC CGA GAG AAC AGT CAC TTG GTG ACA TTC           1363
Val Ser Cys Leu Gln Ser Ser Arg Glu Asn Ser His Leu Val Thr Phe
405              410                 415                 420

TAT GGG AGT GAG AGC CAC AGG GGC CAC TTG TTT GTG TGT GTC ACC CTC           1411
Tyr Gly Ser Glu Ser His Arg Gly His Leu Phe Val Cys Val Thr Leu
             425                 430                 435

TGT GAG CAG ACT CTG GAA GCG TGT TTT GAT GTG CAC AGA GGG GAA GAT           1459
Cys Glu Gln Thr Leu Glu Ala Cys Leu Asp Val His Arg Gly Glu Asp
             440                 445                 450

GTG GAA AAT GAG GAA GAT GAA TTT GCC CGA AAT GTC CTG TCA TCT ATA           1507
Val Glu Asn Glu Glu Asp Glu Phe Ala Arg Asn Val Leu Ser Ser Ile
             455                 460                 465

TTT AAG GCT GTT CAA GAA CTA CAC TTG TCC TGT GGA TAC ACC CAC CAG           1555
Phe Lys Ala Val Gln Glu Leu His Leu Ser Cys Gly Tyr Thr His Gln
             470                 475                 480

GAT CTG CAA CCA CAA AAC ATC TTA ATA GAT TCT AAG AAA GCT GCT CAC           1603
Asp Leu Gln Pro Gln Asn Ile Leu Ile Asp Ser Lys Lys Ala Ala His
485              490                 495                 500

CTG GCA GAT TTT GAT AAG AGC ATC AAG TGG GCT GGA GAT CCA CAG GAA           1651
Leu Ala Asp Phe Asp Lys Ser Ile Lys Trp Ala Gly Asp Pro Gln Glu
             505                 510                 515

GTC AAG AGA GAT CTA GAG GAC CTT GGA CGG CTG GTC CTC TAT GTG GTA           1699
Val Lys Arg Asp Leu Glu Asp Leu Gly Arg Leu Val Leu Tyr Val Val
             520                 525                 530

AAG AAG GGA AGC ATC TCA TTT GAG GAT CTG AAA GCT CAA AGT AAT GAA           1747
Lys Lys Gly Ser Ile Ser Phe Glu Asp Leu Lys Ala Gln Ser Asn Glu
             535                 540                 545

GAG GTG GTT CAA CTT TCT CCA GAT GAG GAA ACT AAG GAC CTC ATT CAT           1795
Glu Val Val Gln Leu Ser Pro Asp Glu Glu Thr Lys Asp Leu Ile His
             550                 555                 560

CGT CTC TTC CAT CCT GGG GAA CAT GTG AGG GAC TGT CTG AGT GAC CTG           1843
Arg Leu Phe His Pro Gly Glu His Val Arg Asp Cys Leu Ser Asp Leu
565              570                 575                 580

CTG GGT CAT CCC TTC TTT TGG ACT TGG GAG AGC CGC TAT AGG ACG CTT           1891
Leu Gly His Pro Phe Phe Trp Thr Trp Glu Ser Arg Tyr Arg Thr Leu
             585                 590                 595

CGG AAT GTG GGA AAT GAA TCC GAC ATC AAA ACA CGA AAA TCT GAA AGT           1939
Arg Asn Val Gly Asn Glu Ser Asp Ile Lys Thr Arg Lys Ser Glu Ser
             600                 605                 610

GAG ATC CTC AGA CTA CTG CAA CCT GGG CCT TCT GAA CAT TCC AAA AGT           1987
Glu Ile Leu Arg Leu Leu Gln Pro Gly Pro Ser Glu His Ser Lys Ser
             615                 620                 625

TTT GAC AAG TGG ACG ACT AAG ATT AAT GAA TGT GTT ATG AAA AAA ATG           2035
Phe Asp Lys Trp Thr Thr Lys Ile Asn Glu Cys Val Met Lys Lys Met
             630                 635                 640

AAT AAG TTT TAT GAA AAA AGA GGC AAT TTC TAC CAG AAC ACT GTG GGT           2083
Asn Lys Phe Tyr Glu Lys Arg Gly Asn Phe Tyr Gln Asn Thr Val Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 645 |     |     |     |     | 650 |     |     |     |     | 655 |     |     |     |     | 660 |      |
| GAT | CTG | CTA | AAG | TTC | ATC | CGG | AAT | TTG | GGA | GAA | CAC | ATT | GAT | GAA | GAA | 2131 |
| Asp | Leu | Leu | Lys | Phe | Ile | Arg | Asn | Leu | Gly | Glu | His | Ile | Asp | Glu | Glu |      |
|     |     |     | 665 |     |     |     |     | 670 |     |     |     |     | 675 |     |     |      |
| AAG | CAT | AAA | AAG | ATG | AAA | TTA | AAA | ATT | GGA | GAC | CCT | TCC | CTG | TAT | TTT | 2179 |
| Lys | His | Lys | Lys | Met | Lys | Leu | Lys | Ile | Gly | Asp | Pro | Ser | Leu | Tyr | Phe |      |
|     |     |     | 680 |     |     |     |     | 685 |     |     |     |     | 690 |     |     |      |
| CAG | AAG | ACA | TTT | CCA | GAT | CTG | GTG | ATC | TAT | GTC | TAC | ACA | AAA | CTA | CAG | 2227 |
| Gln | Lys | Thr | Phe | Pro | Asp | Leu | Val | Ile | Tyr | Val | Tyr | Thr | Lys | Leu | Gln |      |
|     |     |     | 695 |     |     |     |     | 700 |     |     |     |     | 705 |     |     |      |
| AAC | ACA | GAA | TAT | AGA | AAG | CAT | TTC | CCC | CAA | ACC | CAC | AGT | CCA | AAC | AAA | 2275 |
| Asn | Thr | Glu | Tyr | Arg | Lys | His | Phe | Pro | Gln | Thr | His | Ser | Pro | Asn | Lys |      |
|     |     |     | 710 |     |     |     |     | 715 |     |     |     |     | 720 |     |     |      |
| CCT | CAG | TGT | GAT | GGA | GCT | GGT | GGG | GCC | AGT | GGG | TTG | GCC | AGC | CCT | GGG | 2323 |
| Pro | Gln | Cys | Asp | Gly | Ala | Gly | Gly | Ala | Ser | Gly | Leu | Ala | Ser | Pro | Gly |      |
| 725 |     |     |     |     | 730 |     |     |     |     | 735 |     |     |     |     | 740 |      |

TGC TGATGGACTG ATTTGCTGGA GTTCAGGGAA CTACTTATTA GCTGTAGAGT       2376
Cys

CCTTGGCAAA TCACAACATT CTGGGCCTTT TAACTCACCA GGTTGCTTGT GAGGGATGAG 2436

TTGCATAGCT GATATGTCAG TCCCTGGCAT CGTGTATTCC ATATGTCTAT AACAAAAGCA 2496

ATATATACCC AGACTACACT AGTCCATAAG CTTTACCCAC TAACTGGGAG ACATTCTGC  2556

TAAGATTCCT TTTGTCAATT GCACCAAAAG AATGAGTGCC TTGACCCCTA ATGCTGCATA 2616

TGTTACAATT CTCTCACTTA ATTTTCCCAA TGATCTTGCA AAACAGGGAT TATCATCCCC 2676

ATTTAAGAAC TGAGGAACCT GAGACTCAGA GAGTGTGAGC TACTGGCCCA AGATTATTCA 2736

ATTTATACCT AGCACTTTAT AAATTTATGT GGTGTTATTG GTACCTCTCA TTTGGGCACC 2796

TTAAAACTTA ACTATCTTCC AGGGCTCTTC CAGATGAGGC CCAAAACATA TATAGGGGTT 2856

CCAGGAATCT CATTCATTCA TTCAGTATTT ATTGAGCATC TAGTATAAGT CTGGGCACTG 2916

GATGCATGAA TT                                                    2928

(2) INFORMATION FOR SEQ ID NO:2:

(i) SEQUENCE CHARACTERISTICS:
        (A) LENGTH: 741 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Ser Arg Asp His Asn Pro Gln Glu Gly Pro Thr Ser Ser
 1               5                  10                  15

Ser Gly Arg Arg Ala Ala Val Glu Asp Asn His Leu Leu Ile Lys Ala
                20                  25                  30

Val Gln Asn Glu Asp Val Asp Leu Val Gln Gln Leu Leu Glu Gly Gly
            35                  40                  45

Ala Asn Val Asn Phe Gln Glu Glu Gly Gly Trp Thr Pro Leu His
        50                  55                  60

Asn Ala Val Gln Met Ser Arg Glu Asp Ile Val Glu Leu Leu Leu Arg
65                  70                  75                  80

His Gly Ala Asp Pro Val Leu Arg Lys Lys Asn Gly Ala Thr Leu Phe
                85                  90                  95

Ile Leu Ala Ala Ile Ala Gly Ser Val Lys Leu Leu Lys Leu Phe Leu
            100                 105                 110

Ser Lys Gly Ala Asp Val Asn Glu Cys Asp Phe Tyr Gly Phe Thr Ala
        115                 120                 125

-continued

```
Phe Met Glu Ala Ala Val Tyr Gly Lys Val Lys Ala Leu Lys Phe Leu
    130                 135                 140
Tyr Lys Arg Gly Ala Asn Val Asn Leu Arg Arg Lys Thr Lys Glu Asp
145                 150                 155                 160
Gln Glu Arg Leu Arg Lys Gly Ala Thr Ala Leu Met Asp Ala Ala
            165                 170                 175
Glu Lys Gly His Val Glu Val Leu Lys Ile Leu Leu Asp Glu Met Gly
            180                 185                 190
Ala Asp Val Asn Ala Cys Asp Asn Met Gly Arg Asn Ala Leu Ile His
        195                 200                 205
Ala Leu Leu Ser Ser Asp Asp Ser Asp Val Glu Ala Ile Thr His Leu
    210                 215                 220
Leu Leu Asp His Gly Ala Asp Val Asn Val Arg Gly Glu Arg Gly Lys
225                 230                 235                 240
Thr Pro Leu Ile Leu Ala Val Glu Lys Lys His Leu Gly Leu Val Gln
                245                 250                 255
Arg Leu Leu Glu Gln Glu His Ile Glu Ile Asn Asp Thr Asp Ser Asp
            260                 265                 270
Gly Lys Thr Ala Leu Leu Leu Ala Val Glu Leu Lys Leu Lys Lys Ile
        275                 280                 285
Ala Glu Leu Leu Cys Lys Arg Gly Ala Ser Thr Asp Cys Gly Asp Leu
    290                 295                 300
Val Met Thr Ala Arg Arg Asn Tyr Asp His Ser Leu Val Lys Val Leu
305                 310                 315                 320
Leu Ser His Gly Ala Lys Glu Asp Phe His Pro Pro Ala Glu Asp Trp
                325                 330                 335
Lys Pro Gln Ser Ser His Trp Gly Ala Ala Leu Lys Asp Leu His Arg
            340                 345                 350
Ile Tyr Arg Pro Met Ile Gly Lys Leu Lys Phe Phe Ile Asp Glu Lys
        355                 360                 365
Tyr Lys Ile Ala Asp Thr Ser Glu Gly Ile Tyr Leu Gly Phe Tyr
    370                 375                 380
Glu Lys Gln Glu Val Ala Val Lys Thr Phe Cys Glu Gly Ser Pro Arg
385                 390                 395                 400
Ala Gln Arg Glu Val Ser Cys Leu Gln Ser Ser Arg Glu Asn Ser His
                405                 410                 415
Leu Val Thr Phe Tyr Gly Ser Ser His Arg Gly His Leu Phe Val
            420                 425                 430
Cys Val Thr Leu Cys Glu Gln Thr Leu Glu Ala Cys Leu Asp Val His
        435                 440                 445
Arg Gly Glu Asp Val Glu Asn Glu Glu Asp Glu Phe Ala Arg Asn Val
    450                 455                 460
Leu Ser Ser Ile Phe Lys Ala Val Gln Glu Leu His Leu Ser Cys Gly
465                 470                 475                 480
Tyr Thr His Gln Asp Leu Gln Pro Gln Asn Ile Leu Ile Asp Ser Lys
                485                 490                 495
Lys Ala Ala His Leu Ala Asp Phe Asp Lys Ser Ile Lys Trp Ala Gly
            500                 505                 510
Asp Pro Gln Glu Val Lys Arg Asp Leu Glu Asp Leu Gly Arg Leu Val
        515                 520                 525
Leu Tyr Val Val Lys Lys Gly Ser Ile Ser Phe Glu Asp Leu Lys Ala
    530                 535                 540
Gln Ser Asn Glu Glu Val Val Gln Leu Ser Pro Asp Glu Glu Thr Lys
```

```
                    545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655

Asn Thr Val Gly Asp Leu Leu Lys Phe Ile Arg Asn Leu Gly Glu His
            660                 665                 670

Ile Asp Glu Glu Lys His Lys Lys Met Lys Leu Lys Ile Gly Asp Pro
        675                 680                 685

Ser Leu Tyr Phe Gln Lys Thr Phe Pro Asp Leu Val Ile Tyr Val Tyr
    690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Ser Gly Leu
                725                 730                 735

Ala Ser Pro Gly Cys
            740

(2) INFORMATION FOR SEQ ID NO:3:

(i) SEQUENCE CHARACTERISTICS:
        (A) LENGTH: 2200 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 164..2200

(xi) SEQUENCE DESCRIPTION: SEQ ID NO:3:

ATTCGGCACG AGGAAGGTGC CAATTACTAG CTCCCTTCTT TATTCGTGTA CTGATGAGAT      60

GTCAGAAGAC AGAACATAAT CAGCCCAATC CCTACTCCAA GACTCTCATT GTGTCCCAAA     120

GAAACACACG TGTGCATTTC CCAAGGAAAA GGCATTGAGG ACC ATG GAG ACC CCG       175
                                               Met Glu Thr Pro
                                                 1

GAT TAT AAC ACA CCT CAG GGT GGA ACC CCA TCA GCG GGA AGT CAG AGG       223
Asp Tyr Asn Thr Pro Gln Gly Gly Thr Pro Ser Ala Gly Ser Gln Arg
  5                  10                  15                  20

ACC GTT GTC GAA GAT GAT TCT TCG TTG ATC AAA GCT GTT CAG AAG GGA       271
Thr Val Val Glu Asp Asp Ser Ser Leu Ile Lys Ala Val Gln Lys Gly
                 25                  30                  35

GAT GTT GTC AGG GTC CAG CAA TTG TTA GAA AAA GGG GCT GAT GCC AAT       319
Asp Val Val Arg Val Gln Gln Leu Leu Glu Lys Gly Ala Asp Ala Asn
             40                  45                  50

GCC TGT GAA GAC ACC TGG GGC TGG ACA CCT TTG CAC AAC GCA GTG CAA       367
Ala Cys Glu Asp Thr Trp Gly Trp Thr Pro Leu His Asn Ala Val Gln
         55                  60                  65

GCT GGC AGG GTA GAC ATT GTG AAC CTC CTG CTT AGT CAT GGT GCT GAC       415
```

```
Ala Gly Arg Val Asp Ile Val Asn Leu Leu Leu Ser His Gly Ala Asp
         70                  75                  80

CCT CAT CGG AGG AAG AAG AAT GGG GCC ACC CCC TTC ATC ATT GCT GGG    463
Pro His Arg Arg Lys Lys Asn Gly Ala Thr Pro Phe Ile Ile Ala Gly
 85                  90                  95                 100

ATC CAG GGA GAT GTG AAA CTG CTC GAG ATT CTC CTC TCT TGT GGT GCA    511
Ile Gln Gly Asp Val Lys Leu Leu Glu Ile Leu Leu Ser Cys Gly Ala
                    105                 110                 115

GAC GTC AAT GAG TGT GAC GAG AAC GGA TTC ACG GCT TTC ATG GAA GCT    559
Asp Val Asn Glu Cys Asp Glu Asn Gly Phe Thr Ala Phe Met Glu Ala
                120                 125                 130

GCT GAG CGT GGT AAC GCT GAA GCC TTA AGA TTC CTT TTT GCT AAG GGA    607
Ala Glu Arg Gly Asn Ala Glu Ala Leu Arg Phe Leu Phe Ala Lys Gly
            135                 140                 145

GCC AAT GTG AAT TTG CGA CGA CAG ACA ACG AAG GAC AAA AGG CGA TTG    655
Ala Asn Val Asn Leu Arg Arg Gln Thr Thr Lys Asp Lys Arg Arg Leu
        150                 155                 160

AAG CAA GGA GGC GCC ACA GCT CTC ATG AGC GCT GCT GAG AAG GGC CAC    703
Lys Gln Gly Gly Ala Thr Ala Leu Met Ser Ala Ala Glu Lys Gly His
165                 170                 175                 180

CTG GAA GTC CTG AGA ATT CTC CTC AAT GAC ATG AAG GCA GAA GTC GAT    751
Leu Glu Val Leu Arg Ile Leu Leu Asn Asp Met Lys Ala Glu Val Asp
                185                 190                 195

GCT CGG GAC AAC ATG GGC AGA AAT GCC CTG ATC CGT ACT CTG CTG AAC    799
Ala Arg Asp Asn Met Gly Arg Asn Ala Leu Ile Arg Thr Leu Leu Asn
                200                 205                 210

TGG GAT TGT GAA AAT GTG GAG GAG ATT ACT TCA ATC CTG ATT CAG CAC    847
Trp Asp Cys Glu Asn Val Glu Glu Ile Thr Ser Ile Leu Ile Gln His
            215                 220                 225

GGG GCT GAT GTT AAC GTG AGA GGA GAA AGA GGG AAA ACA CCC CTC ATC    895
Gly Ala Asp Val Asn Val Arg Gly Glu Arg Gly Lys Thr Pro Leu Ile
        230                 235                 240

GCA GCA GTG GAG AGG AAG CAC ACA GGC TTG GTG CAG ATG CTC CTG AGT    943
Ala Ala Val Glu Arg Lys His Thr Gly Leu Val Gln Met Leu Leu Ser
245                 250                 255                 260

CGG GAA GGC ATA AAC ATA GAT GCC AGG GAT AAC GAG GGC AAG ACA GCT    991
Arg Glu Gly Ile Asn Ile Asp Ala Arg Asp Asn Glu Gly Lys Thr Ala
                265                 270                 275

CTG CTA ATT GCT GTT GAT AAA CAA CTG AAG GAA ATT GTC CAG TTG CTT   1039
Leu Leu Ile Ala Val Asp Lys Gln Leu Lys Glu Ile Val Gln Leu Leu
                280                 285                 290

CTT GAA AAG GGA GCT GAT AAG TGT GAC GAT CTT GTT TGG ATA GCC AGG   1087
Leu Glu Lys Gly Ala Asp Lys Cys Asp Asp Leu Val Trp Ile Ala Arg
            295                 300                 305

AGG AAT CAT GAC TAT CAC CTT GTA AAG CTT CTC CTC CCT TAT GTA GCT   1135
Arg Asn His Asp Tyr His Leu Val Lys Leu Leu Leu Pro Tyr Val Ala
        310                 315                 320

AAT CCT GAC ACC GAC CCT CCT GCT GGA GAC TGG TCG CCT CAC AGT TCA   1183
Asn Pro Asp Thr Asp Pro Pro Ala Gly Asp Trp Ser Pro His Ser Ser
325                 330                 335                 340

CGT TGG GGG ACA GCC TTG AAA AGC CTC CAC AGT ATG ACT CGA CCC ATG   1231
Arg Trp Gly Thr Ala Leu Lys Ser Leu His Ser Met Thr Arg Pro Met
                345                 350                 355

ATT GGC AAA CTC AAG ATC TTC ATT CAT GAT GAC TAT AAA ATT GCT GGC   1279
Ile Gly Lys Leu Lys Ile Phe Ile His Asp Asp Tyr Lys Ile Ala Gly
                360                 365                 370

ACT TCC GAA GGG GCT GTC TAC CTA GGG ATC TAT GAC AAT CGA GAA GTG   1327
Thr Ser Glu Gly Ala Val Tyr Leu Gly Ile Tyr Asp Asn Arg Glu Val
            375                 380                 385

GCT GTG AAG GTC TTC CGT GAG AAT AGC CCA CGT GGA TGT AAG GAA GTC   1375
```

```
Ala Val Lys Val Phe Arg Glu Asn Ser Pro Arg Gly Cys Lys Glu Val
            390                 395                 400

TCT TGT CTG CGG GAC TGC GGT GAC CAC AGT AAC TTA GTG GCT TTC TAT      1423
Ser Cys Leu Arg Asp Cys Gly Asp His Ser Asn Leu Val Ala Phe Tyr
405                 410                 415                 420

GGA AGA GAG GAC GAT AAG GGC TGT TTA TAT GTG TGT GTG TCC CTG TGT      1471
Gly Arg Glu Asp Asp Lys Gly Cys Leu Tyr Val Cys Val Ser Leu Cys
                    425                 430                 435

GAG TGG ACA CTG GAA GAG TTC CTG AGG TTG CCC AGA GAG GAA CCT GTG      1519
Glu Trp Thr Leu Glu Glu Phe Leu Arg Leu Pro Arg Glu Glu Pro Val
                440                 445                 450

GAG AAC GGG GAA GAT AAG TTT GCC CAC AGC ATC CTA TTA TCT ATA TTT      1567
Glu Asn Gly Glu Asp Lys Phe Ala His Ser Ile Leu Leu Ser Ile Phe
            455                 460                 465

GAG GGT GTT CAA AAA CTA CAC TTG CAT GGA TAT TCC CAT CAG GAC CTG      1615
Glu Gly Val Gln Lys Leu His Leu His Gly Tyr Ser His Gln Asp Leu
470                 475                 480

CAA CCA CAA AAC ATC TTA ATA GAT TCC AAG AAA GCT GTC CGG CTG GCA      1663
Gln Pro Gln Asn Ile Leu Ile Asp Ser Lys Lys Ala Val Arg Leu Ala
485                 490                 495                 500

GAT TTT GAT CAG AGC ATC CGA TGG ATG GGA GAG TCA CAG ATG GTC AGG      1711
Asp Phe Asp Gln Ser Ile Arg Trp Met Gly Glu Ser Gln Met Val Arg
                    505                 510                 515

AGA GAC TTG GAG GAT CTT GGA CGG CTG GTT CTC TAC GTG GTA ATG AAA      1759
Arg Asp Leu Glu Asp Leu Gly Arg Leu Val Leu Tyr Val Val Met Lys
                520                 525                 530

GGT GAG ATC CCC TTT GAG ACA CTA AAG ACT CAG AAT GAT GAA GTG CTG      1807
Gly Glu Ile Pro Phe Glu Thr Leu Lys Thr Gln Asn Asp Glu Val Leu
            535                 540                 545

CTT ACA ATG TCT CCA GAT GAG GAG ACT AAG GAC CTC ATT CAT TGC CTG      1855
Leu Thr Met Ser Pro Asp Glu Glu Thr Lys Asp Leu Ile His Cys Leu
550                 555                 560

TTT TCT CCT GGA GAA AAT GTC AAG AAC TGC CTG GTA GAC CTG CTT GGC      1903
Phe Ser Pro Gly Glu Asn Val Lys Asn Cys Leu Val Asp Leu Leu Gly
565                 570                 575                 580

CAT CCT TTC TTT TGG ACT TGG GAG AAC CGC TAT AGA ACA CTC CGG AAT      1951
His Pro Phe Phe Trp Thr Trp Glu Asn Arg Tyr Arg Thr Leu Arg Asn
                    585                 590                 595

GTG GGA AAT GAA TCT GAC ATC AAA GTA CGG AAA TGT AAA AGT GAT CTT      1999
Val Gly Asn Glu Ser Asp Ile Lys Val Arg Lys Cys Lys Ser Asp Leu
                600                 605                 610

CTC AGA CTA CTG CAG CAT CAG ACA CTT GAG CCT CCC AGA AGC TTT GAC      2047
Leu Arg Leu Leu Gln His Gln Thr Leu Glu Pro Pro Arg Ser Phe Asp
            615                 620                 625

CAG TGG ACA TCT AAG ATC GAC AAA AAT GTT ATG GAT GAA ATG AAT CAT      2095
Gln Trp Thr Ser Lys Ile Asp Lys Asn Val Met Asp Glu Met Asn His
630                 635                 640

TTC TAC GAA AAG AGA AAA AAA AAC CCT TAT CAG GAT ACT GTA GGT GAT      2143
Phe Tyr Glu Lys Arg Lys Lys Asn Pro Tyr Gln Asp Thr Val Gly Asp
645                 650                 655                 660

CTG CTG AAG TTT ATT CGG AAT ATA GGC GAA CAC ATC AAT GAG GAA AAA      2191
Leu Leu Lys Phe Ile Arg Asn Ile Gly Glu His Ile Asn Glu Glu Lys
                    665                 670                 675

AAG CGG GGG                                                           2200
Lys Arg Gly
```

(2) INFORMATION FOR SEQ ID NO:4:

(i) SEQUENCE CHARACTERISTICS:
        (A) LENGTH: 679 amino acids
        (B) TYPE: amino acid (D) TOPOLOGY: linear (ii) MOLECULE TYPE: protein (xi) SEQUENCE DESCRIPTION: SEQ ID NO:4:

```
Met Glu Thr Pro Asp Tyr Asn Thr Pro Gln Gly Thr Pro Ser Ala
 1               5                  10                  15

Gly Ser Gln Arg Thr Val Val Glu Asp Asp Ser Ser Leu Ile Lys Ala
                20                  25                  30

Val Gln Lys Gly Asp Val Val Arg Val Gln Gln Leu Leu Glu Lys Gly
            35                  40                  45

Ala Asp Ala Asn Ala Cys Glu Asp Thr Trp Gly Trp Thr Pro Leu His
        50                  55                  60

Asn Ala Val Gln Ala Gly Arg Val Asp Ile Val Asn Leu Leu Leu Ser
65                  70                  75                  80

His Gly Ala Asp Pro His Arg Arg Lys Lys Asn Gly Ala Thr Pro Phe
                85                  90                  95

Ile Ile Ala Gly Ile Gln Gly Asp Val Lys Leu Leu Glu Ile Leu Leu
                100                 105                 110

Ser Cys Gly Ala Asp Val Asn Glu Cys Asp Glu Asn Gly Phe Thr Ala
            115                 120                 125

Phe Met Glu Ala Ala Glu Arg Gly Asn Ala Glu Ala Leu Arg Phe Leu
    130                 135                 140

Phe Ala Lys Gly Ala Asn Val Asn Leu Arg Arg Gln Thr Thr Lys Asp
145                 150                 155                 160

Lys Arg Arg Leu Lys Gln Gly Gly Ala Thr Ala Leu Met Ser Ala Ala
                165                 170                 175

Glu Lys Gly His Leu Glu Val Leu Arg Ile Leu Leu Asn Asp Met Lys
                180                 185                 190

Ala Glu Val Asp Ala Arg Asp Asn Met Gly Arg Asn Ala Leu Ile Arg
            195                 200                 205

Thr Leu Leu Asn Trp Asp Cys Glu Asn Val Glu Glu Ile Thr Ser Ile
        210                 215                 220

Leu Ile Gln His Gly Ala Asp Val Asn Val Arg Gly Glu Arg Gly Lys
225                 230                 235                 240

Thr Pro Leu Ile Ala Ala Val Glu Arg Lys His Thr Gly Leu Val Gln
                245                 250                 255

Met Leu Leu Ser Arg Glu Gly Ile Asn Ile Asp Ala Arg Asp Asn Glu
                260                 265                 270

Gly Lys Thr Ala Leu Leu Ile Ala Val Asp Lys Gln Leu Lys Glu Ile
            275                 280                 285

Val Gln Leu Leu Leu Glu Lys Gly Ala Asp Lys Cys Asp Asp Leu Val
    290                 295                 300

Trp Ile Ala Arg Arg Asn His Asp Tyr His Leu Val Lys Leu Leu Leu
305                 310                 315                 320

Pro Tyr Val Ala Asn Pro Asp Thr Asp Pro Pro Ala Gly Asp Trp Ser
                325                 330                 335

Pro His Ser Ser Arg Trp Gly Thr Ala Leu Lys Ser Leu His Ser Met
                340                 345                 350

Thr Arg Pro Met Ile Gly Lys Leu Lys Ile Phe Ile His Asp Asp Tyr
            355                 360                 365

Lys Ile Ala Gly Thr Ser Glu Gly Ala Val Tyr Leu Gly Ile Tyr Asp
        370                 375                 380

Asn Arg Glu Val Ala Val Lys Val Phe Arg Glu Asn Ser Pro Arg Gly
385                 390                 395                 400
```

```
Cys Lys Glu Val Ser Cys Leu Arg Asp Cys Gly Asp His Ser Asn Leu
                405                 410                 415
Val Ala Phe Tyr Gly Arg Glu Asp Lys Gly Cys Leu Tyr Val Cys
            420                 425                 430
Val Ser Leu Cys Glu Trp Thr Leu Glu Glu Phe Leu Arg Leu Pro Arg
            435                 440                 445
Glu Glu Pro Val Glu Asn Gly Asp Lys Phe Ala His Ser Ile Leu
450                 455                 460
Leu Ser Ile Phe Glu Gly Val Gln Lys Leu His Leu His Gly Tyr Ser
465                 470                 475                 480
His Gln Asp Leu Gln Pro Gln Asn Ile Leu Ile Asp Ser Lys Lys Ala
                485                 490                 495
Val Arg Leu Ala Asp Phe Asp Gln Ser Ile Arg Trp Met Gly Glu Ser
                500                 505                 510
Gln Met Val Arg Arg Asp Leu Glu Asp Leu Gly Arg Leu Val Leu Tyr
            515                 520                 525
Val Val Met Lys Gly Glu Ile Pro Phe Glu Thr Leu Lys Thr Gln Asn
            530                 535                 540
Asp Glu Val Leu Leu Thr Met Ser Pro Asp Glu Thr Lys Asp Leu
545                 550                 555                 560
Ile His Cys Leu Phe Ser Pro Gly Glu Asn Val Lys Asn Cys Leu Val
                565                 570                 575
Asp Leu Leu Gly His Pro Phe Phe Trp Thr Trp Glu Asn Arg Tyr Arg
                580                 585                 590
Thr Leu Arg Asn Val Gly Asn Glu Ser Asp Ile Lys Val Arg Lys Cys
                595                 600                 605
Lys Ser Asp Leu Leu Arg Leu Leu Gln His Gln Thr Leu Glu Pro Pro
610                 615                 620
Arg Ser Phe Asp Gln Trp Thr Ser Lys Ile Asp Lys Asn Val Met Asp
625                 630                 635                 640
Glu Met Asn His Phe Tyr Glu Lys Arg Lys Asn Pro Tyr Gln Asp
                645                 650                 655
Thr Val Gly Asp Leu Leu Lys Phe Ile Arg Asn Ile Gly Glu His Ile
                660                 665                 670
Asn Glu Glu Lys Lys Arg Gly
                675

(2) INFORMATION FOR SEQ ID NO:5:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Asp Arg Arg Lys Pro Arg Gln Asn Asn Arg Asp Arg Asn Glu Arg
1                5                 10                  15
Arg Asp Thr Arg Ser Glu Arg Thr Glu Gly Ser Asp Asn Arg Glu Glu
            20                  25                  30
Asn Arg Arg Asn Arg Arg Gln Ala Gln Gln Thr Ala Glu Thr Arg
                35                  40                  45
Glu Ser Arg Gln Gln Ala Glu Val Thr Glu Lys Ala Arg Thr Ala Asp
50                  55                  60
```

```
Glu Gln Gln Ala Pro Arg Arg Glu Arg Ser Arg Arg Arg Asn Asp Asp
 65              70              75              80

Lys Arg Gln Ala Gln Gln Glu Ala Lys Ala Leu Asn Val Glu Glu Gln
             85              90              95

Ser Val Gln Glu Thr Glu Gln Glu Glu Arg Val Arg Pro Val Gln Pro
            100             105             110

Arg Arg Lys Gln Arg Gln Leu Asn Gln Lys Val Arg Tyr Glu Gln Ser
            115             120             125

Val Ala Glu Glu Ala Val Val Ala Pro Val Val Glu Glu Thr Val Ala
        130             135             140

Ala Glu Pro Ile Val Gln Glu Ala Pro Ala Pro Arg Thr Glu Leu Val
145             150             155             160

Lys Val Pro Leu Pro Val Val Ala Gln Thr Ala Pro Glu Gln Gln Glu
            165             170             175

Glu Asn Asn Ala Asp Asn Arg Asp Asn Gly Gly Met Pro Ser
            180             185             190
```